(12) United States Patent
Chein et al.

(10) Patent No.: US 12,109,207 B2
(45) Date of Patent: Oct. 8, 2024

(54) METHODS OF USING 4(1H)-QUINOLONE DERIVATIVES

(71) Applicant: Academia Sinica, Taipei (TW)

(72) Inventors: Rong-Jie Chein, Taipei (TW); Pan-Chyr Yang, Taipei (TW); Chi-Huey Wong, Taipei (TW); Ming-Shiu Lin, Taipei (TW); Ting-Jen Cheng, Taipei (TW); Ting-Hung Rachel Chou, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 18/184,364

(22) Filed: Mar. 15, 2023

(65) Prior Publication Data

US 2023/0233549 A1 Jul. 27, 2023

Related U.S. Application Data

(62) Division of application No. 16/831,346, filed on Mar. 26, 2020, now Pat. No. 11,638,705.

(Continued)

(51) Int. Cl.
*A61K 31/47* (2006.01)
*A61K 45/06* (2006.01)
(Continued)

(52) U.S. Cl.
CPC .............. *A61K 31/47* (2013.01); *A61K 45/06* (2013.01); *A61P 35/00* (2018.01); *C07D 215/233* (2013.01)

(58) Field of Classification Search
CPC .... A61K 31/47; A61K 45/06; A61K 2300/00; A61P 35/00; A61P 35/02; C07D 215/233; C07D 215/48

(Continued)

(56) References Cited

U.S. PATENT DOCUMENTS

| 4,711,898 A | 12/1987 | Enomoto et al. |
| 2005/0032832 A1* | 2/2005 | Kuo .................... A61P 35/00 546/156 |

FOREIGN PATENT DOCUMENTS

| CN | 108610286 A | 2/2018 |
| CN | 109516973 A | 3/2019 |

(Continued)

OTHER PUBLICATIONS

Sato et al., Convenient Synthesis of 1,6,7,8-Substituted 2-(3',4'-Substituted-phenyl)-4-quinolones via a 4-Ethoxyflavyhum Salt, J. Heterocyclic Chem . . . 36, Sep.-Oct. 1999, 1189-1193). (Year: 1999).*

(Continued)

*Primary Examiner* — Taylor V Oh
(74) *Attorney, Agent, or Firm* — Muncy, Geissler, Olds & Lowe, P.C.

(57) ABSTRACT

Provided herein are compounds of Formula (I). The disclosure provides new compounds, compositions, and methods for treating, delaying, and/or preventing the adverse effects of proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression)). Provided are methods of inhibiting polymerization of a cancer cell microtubule in a subject in need thereof or a cell, tissue, or biological sample, binding β-tubulin, inhibiting microtubule assembly and, inducing apoptosis in a cancer cell resistant to multiple drugs in a tissue, biological sample, or subject. Also provided in the present disclosure are pharmaceutical compositions, kits, and methods of using the compounds for treating any of the target diseases described herein.

(Continued)

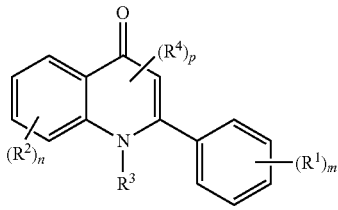

(I)

34 Claims, 24 Drawing Sheets
(4 of 24 Drawing Sheet(s) Filed in Color)

Related U.S. Application Data

(60) Provisional application No. 62/836,533, filed on Apr. 19, 2019.

(51) Int. Cl.
*A61P 35/00* (2006.01)
*C07D 215/233* (2006.01)

(58) Field of Classification Search
USPC .................................................. 514/312
See application file for complete search history.

(56) References Cited

FOREIGN PATENT DOCUMENTS

| EP | 0104959 | A1 | 4/1984 |
| EP | 0811613 | A1 | 12/1997 |
| EP | 1380575 | A1 | 1/2004 |
| JP | S604170 | A | 1/1985 |
| WO | WO-2009/087684 | A2 | 7/2009 |

OTHER PUBLICATIONS

Åkerbladh, L. et al., "Synthesis of 4-Quinolones via A Carbonylative Sonogashira cross-coupling Using Molybdenum Hexacarbonyl as a CO Source," *The Journal of Organic Chemistry*, (2015), 80(3), 1464-1471.

Soural, M et al., "2-Phenylsubstituted-3-Hydroxyquinolin-4(1*H*)-one-Carboxamides: Structure-Cytotoxic Activity Relationship Study," *ACS Combinatorial Science*, (2010), 13(1), 39-44.

Chou, L.-C. et al., "Design, Synthesis, and Preclinical Evaluation of New 5,6- (or 6,7-) Disubstituted-2-(fluorophenyl)quinolin-4-one derivatives as Potent Antitumor Agents," *Journal of Medicinal Chemistry*, (2010), 53(22), 8047-8058.

Soural, M. et al.,. "Synthesis and cytotoxic activity of substituted 2-phenyl-3-hydroxy-4(1*H*)-quinolinones-7-carboxylic acids and their phenacyl esters," *European Journal of Medicinal Chemistry*, (2006), 41(4), 467-474.

Lin, Ming-Shiu et al. "4(1H)-quinolone derivatives overcome acquired resistance to anti-microtubule agents by targeting the colchicine site of β-tubulin," European Journal of Medicinal Chemistry, vol. 181, Nov. 1, 2019, pp. 1-15 (111584).

Jiwei Wu; "From Ketones, Amines, and Carbon Monoxide to 4-Quinolones:Palladium-Catalyzed Oxidative Carbonylation" American Chemical Society; Org. Lett. 2017, 19, pp. 6432-6435.

Ting-Chia Ko et al.; "Synthesis of 4-Alkoxy-2-phenylquinoline Derivatives as Potent Antiplatelet Agents";Bioorganic & Medicinal Chemistry Letters 11 (2001) pp. 279-282.

Shingo Sato; "Convenient Synthesis of 1,6,7,8-Substituted 2-(3',4'-Substitutedphenyl)-4-quinolones via a 4-Ethoxyflavylium Salt"; *J. Heterocyclic Chem.*, 36, Sep.-Oct. 1999; pp. 1189-1191.

\* cited by examiner

METHODS OF USING 4(1H)-QUINOLONE DERIVATIVES

CROSS REFERENCE TO RELATED APPLICATION

This application is a division of pending U.S. patent application Ser. No. 16/831,346 filed Mar. 26, 2020, which claims the benefit of filing date of U.S. Provisional Application Ser. No. 62/836,533 filed Apr. 19, 2019. The entirety of each of said Provisional applications is incorporated herein by reference.

BACKGROUND OF THE INVENTION

1. Field of the Invention

The present invention relates to 4(1H)-quinolone derivatives and use thereof in treating, delaying, and/or preventing the adverse effects of proliferative diseases.

2. Description of Related Art

Cancer is the second most common cause of death worldwide, and lung cancer is the leading cause of cancer-related deaths. Despite advances in treatment during the past 20 years, the prognosis for lung cancer patients remains poor. Drug resistance limits the efficacy of anticancer agents and is responsible for treatment failure in most cases. Consequently, the development of new drugs to overcome drug resistance and improve survival of cancer patients is urgently needed.

Microtubules are long, hollow cylinders composed of heterodimeric α/β-tubulin units. They are an important component of the cell cytoskeleton and are involved in mitosis, motility, and organelle transport. Cancer cells depend on microtubules for mitosis and rapid division, which makes microtubules a suitable target for anticancer agents. Nucleation of microtubules occurs at the centrosome, and, as they are highly dynamic structures that continuously assemble and disassemble, microtubule-targeting agents (MTAs) can regulate their dynamics and, consequently, cause mitotic arrest and subsequently cell apoptosis. MTAs, i.e., taxanes, vinca alkaloids, colchicine, and laulimalide, are classified according to their mode of action and tubulin-binding site. The taxanes (e.g., paclitaxel and ixabepilone) and the vinca alkaloids (e.g., vincristine and vinblastine) are the two major types of MTAs that are widely used clinically to treat many different types of malignant cancers, including those of the lung, breast, ovary, prostate, and head and neck and leukemia. However, cancers in most patients who have been treated for prolonged periods with MTA become acquired resistant to the treatment protocol.

The two major mechanisms of MTA-induced resistance involve mutations in β-tubulin and ATP-binding cassette efflux transporters. A structurally altering mutation at a β-tubulin drug-binding site or expression of a β-tubulin isotype with an altered conformation may interfere with the interaction between an MTA and its binding site on β-tubulin, thereby causing treatment failure. Efflux transporters embedded in cell membranes may pump different types of anti-cancer drug from the intracellular to the extracellular space, which decreases intracellular drug accumulation, resulting in multidrug resistance (MDR) and making it more difficult to treat patients with cancer. P-glycoprotein (P-gp) was the first identified ATP-binding cassette efflux pump and has been well characterized. MDR caused by P-gp overexpression is the most common resistance mechanism known involving clinical cancer therapies, and, therefore, finding new agents that will improve patient outcomes and circumvent drug resistance remains a major and unmet need.

SUMMARY OF THE INVENTION

Developing new therapeutic strategies to overcome drug resistance of cancer cells is an ongoing endeavor. From among 2 million chemicals, ethyl 4-oxo-2-phenyl-1,4-dihydroquinoline-6-carboxylate (AS1712) was identified as a low-toxicity inhibitor of lung cancer cell proliferation and xenograft tumor growth. Shown herein is exemplary compound AS1712 which is active against broad cancer cell lines and able to bind in the colchicine-binding pocket of β-tubulin, thereby inhibiting microtubule assembly and, consequently, inducing mitotic arrest and apoptosis. The cell-based structure-activity relationship study described herein identified a new exemplary compound, ethyl 2-(3-fluorophenyl)-4-oxo-1,4-dihydro quinoline-6-carboxylate (RJ-LC-15-8), which had a greater anti-proliferative potency ($IC_{50}$=24 nM) for H1975 cells, while maintaining a similar mechanism of action as AS1712. Notably, both exemplary compounds AS1712 and RJ-LC-15-8 overcame P-glycoprotein efflux pump and β-tubulin alterations that lead to acquired resistance against microtubule-targeting drugs of cancer cells. AS1712 and RJ-LC-15-8 may be exemplary compounds for developing drugs that overcome acquired resistance to microtubule-targeting agents of cancer cells. Further identifying additional compounds that can treat proliferative diseases (e.g., cancer), by overcoming acquired resistance to microtubule-targeting agents of cancer cells is of interest.

Accordingly, the present disclosure provides compounds, such as compounds of below Formula (I). The compounds described herein may be useful in treating proliferative diseases (e.g., cancer resistant to treatment by one or more microtubule-targeting agents (e.g., cancer resistant to multiple drugs associated with P-glycoprotein (P-gp) overexpression)) in a subject in need thereof. The disclosure therefore provides new compounds, compositions, and methods for the treatment of various diseases (e.g., proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression)). The cancers described herein may be resistant to treatment by one or more microtubule-targeting agents (e.g., taxanes or vinca alkaloids). The compounds described herein may inhibit polymerization of a cancer cell microtubule in a subject in need thereof or a cell, tissue, or biological sample, bind β-tubulin, inhibit microtubule assembly and, consequently, induce apoptosis in a cancer cell resistant to multiple drugs in a tissue, biological sample, or subject. Described herein are compounds of below Formula (I). Also provided are pharmaceutical compositions, kits, methods, and uses of any of the compounds described herein.

In one aspect, the present disclosure provides compounds of Formula (I):

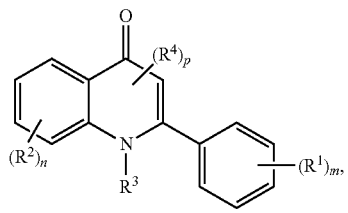

or a pharmaceutically acceptable salt, co-crystal, tautomer, stereoisomer, solvate, hydrate, polymorph, isotopically enriched derivative, or prodrug thereof, wherein:

each instance of $R^1$ is independently halogen, —C(=O)(optionally substituted alkyl); optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{D1}$, —N(R$^{D1a}$)$_2$, or —SR$^{D1}$;

each instance of $R^2$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{D1}$, —N(R$^{D1a}$)$_2$, or —SR$^{D1}$;

$R^3$ is hydrogen, optionally substituted alkyl, or a nitrogen protecting group;

each instance of $R^4$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —OR$^{D1}$, —N(R$^{D1a}$)$_2$, or —SR$^{D1}$;

$R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring;

m is 0, 1, 2, 3, 4, or 5;
n is 0, 1, 2, 3, or 4; and
p is 0 or 1.

In one aspect, the present disclosure provides compounds of Formula (I):

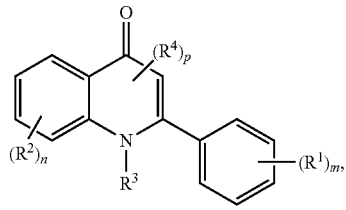

or a pharmaceutically acceptable salt thereof, wherein:
$R^1$, $R^2$, $R^3$, $R^4$, m, n, and p are as described herein In certain embodiments, at least one of m and n is not 0.

In certain embodiments, a compound of Formula (I) is of Formulae (IA), (IB), or (IC):

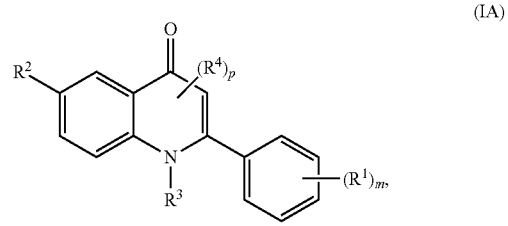

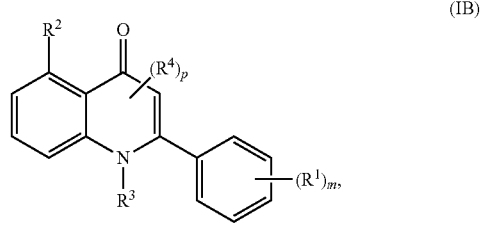

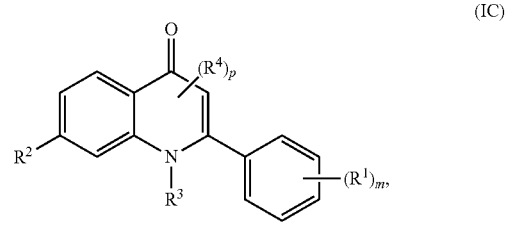

or a pharmaceutically acceptable salt, co-crystal, tautomer, stereoisomer, solvate, hydrate, polymorph, isotopically enriched derivative, or prodrug thereof, wherein $R^1$, $R^2$, $R^3$, $R^4$, m, and p are as described herein.

In certain embodiments, a compound of Formula (I) is of the formula:

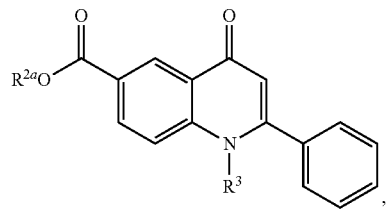

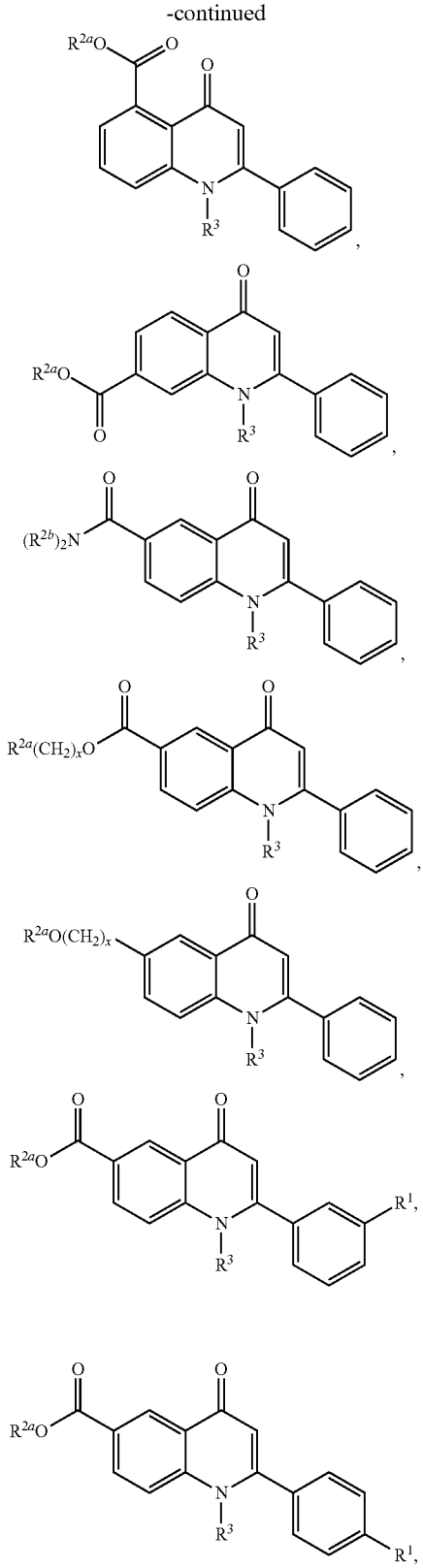
or a pharmaceutically acceptable salt, co-crystal, tautomer, stereoisomer, solvate, hydrate, polymorph, isotopically enriched derivative, or prodrug thereof, wherein $R^1$, $R^{2a}$, $R^{2b}$, $R^3$ are as described herein.
Exemplary compounds of Formula (I) include, but are not limited to:
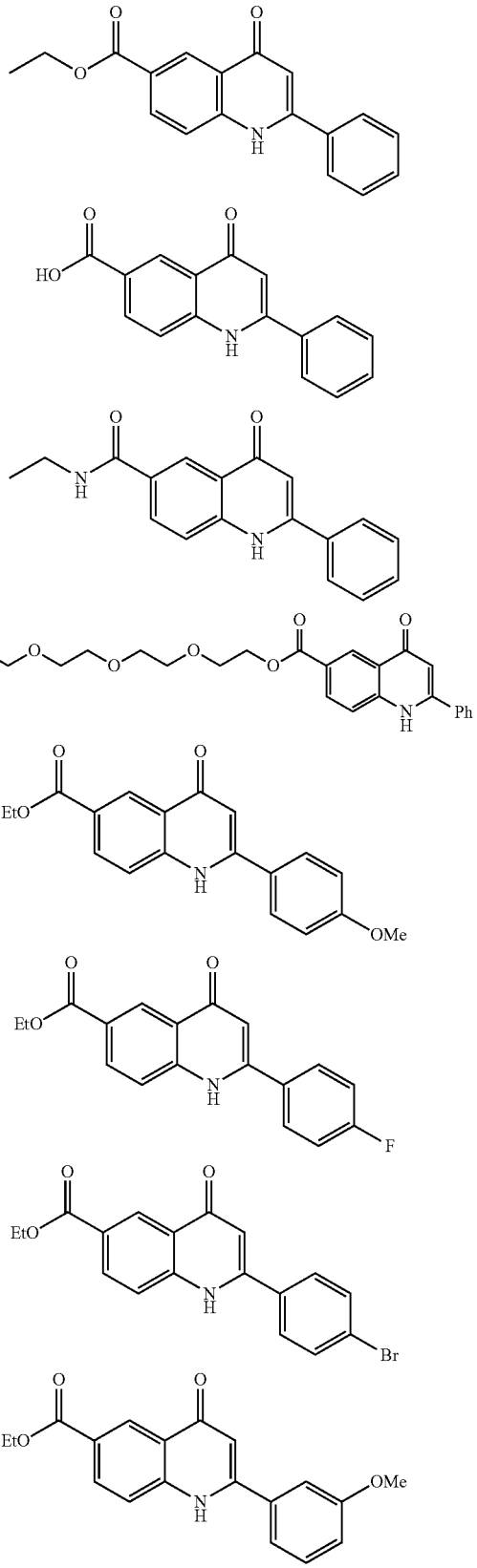

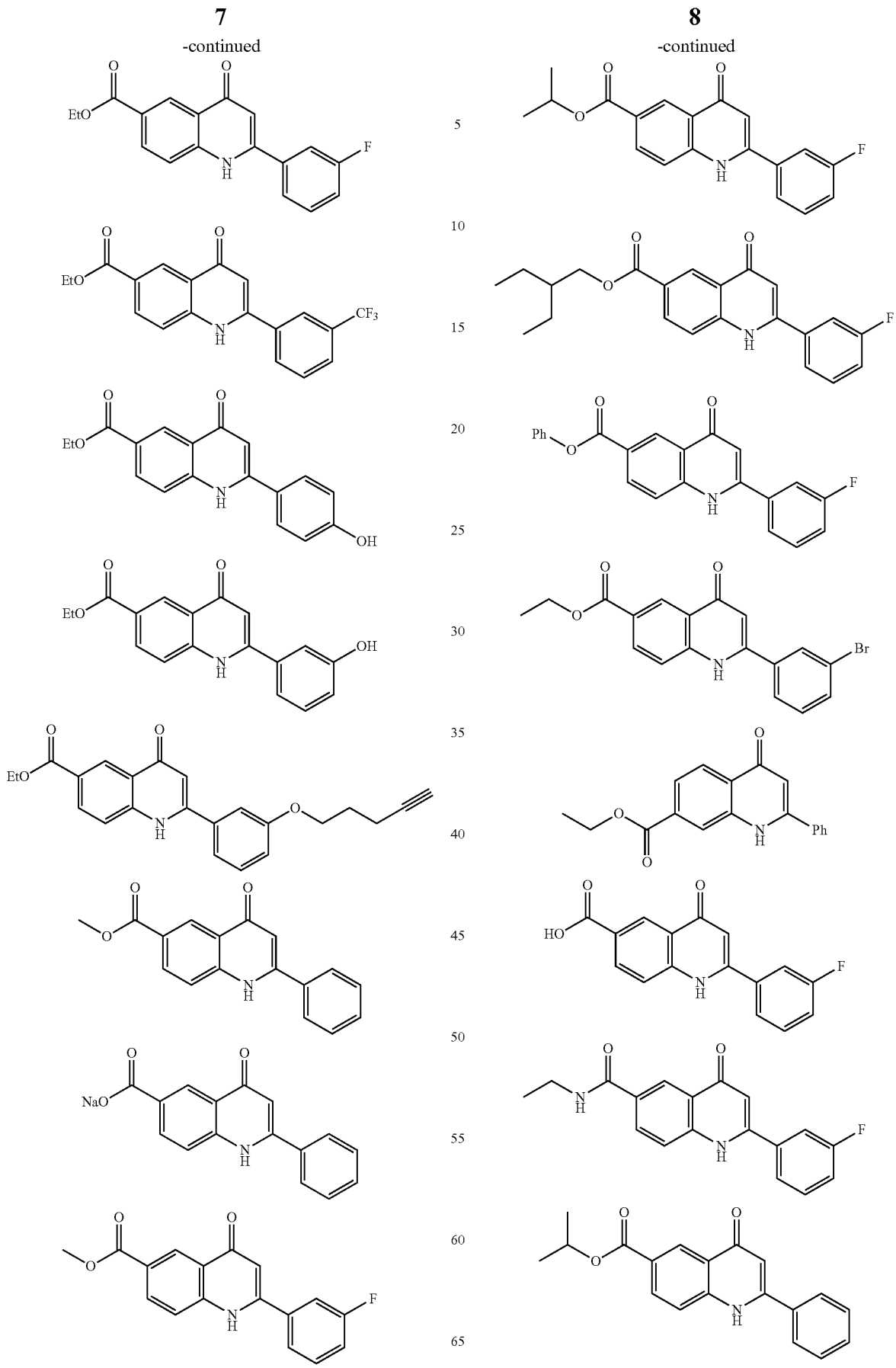

-continued

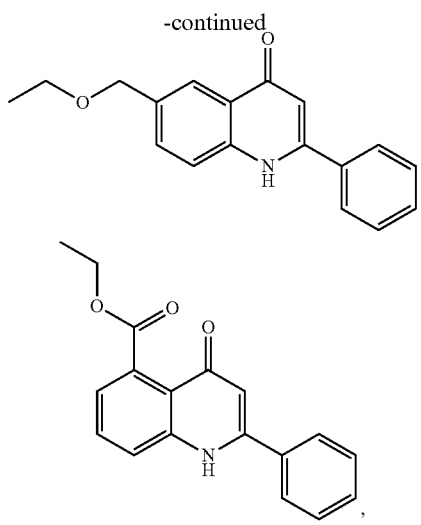

or a pharmaceutically acceptable salt, co-crystal, tautomer, stereoisomer, solvate, hydrate, polymorph, isotopically enriched derivative, or prodrug thereof.

In another aspect, the present disclosure provides pharmaceutical compositions including one or more of the compounds described herein, and a pharmaceutically acceptable excipient. In certain embodiments, a pharmaceutical composition described herein includes a therapeutically or prophylactically effective amount of a compound described herein. The pharmaceutical compositions may be useful in inhibiting polymerization of a cancer cell microtubule in a subject in need thereof or a cell, tissue, or biological sample, binding β-tubulin, inhibiting microtubule assembly, and inducing apoptosis in a cancer cell resistant to multiple drugs in a tissue, biological sample, or subject, in treating proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression)) in a subject in need thereof. The cancers described herein may be resistant to treatment by one or more microtubule-targeting agents (e.g., taxanes or vinca alkaloids). In certain embodiments, the compound being administered or used inhibits polymerization of a cancer cell microtubule in a subject in need thereof or a cell, tissue, or biological sample, binds β-tubulin, inhibits microtubule assembly, induces apoptosis in a cancer cell resistant to multiple drugs in a tissue, biological sample, or subject, treats proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression) (e.g., cancer resistant to treatment by one or more microtubule-targeting agents (e.g., taxanes or vinca alkaloids))) in a subject in need thereof, or prevents a proliferative disease in a subject in need thereof. In certain embodiments, the subject being treated is a mammal (e.g., human or non-human mammal). All types of biological samples described herein or known in the art are contemplated as being within the scope of the invention.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. The kit may also optionally include a device for administration of the compound or composition (e.g., a syringe such as a pre-filled syringe for parenteral administration).

In certain embodiments, the compound being administered or used inhibits polymerization of a cancer cell microtubule in a subject in need thereof or a cell, tissue, or biological sample, binds β-tubulin, inhibits microtubule assembly, and/or induces apoptosis in a cancer cell resistant to multiple drugs in a tissue, biological sample, or subject.

Another aspect of the present disclosure relates to methods of treating a proliferative disease in a subject in need thereof, the methods comprising administering to the subject a therapeutically effective amount of a compound or pharmaceutical composition described herein. In another aspect, the present disclosure provides methods of preventing a proliferative disease in a subject in need thereof, the methods comprises administering to the subject a prophylactically effective amount of a compound or pharmaceutical composition described herein.

In yet another aspect, the present disclosure provides compounds and pharmaceutical compositions described herein for use in a method of the disclosure (e.g., a method of inhibiting polymerization of a cancer cell microtubule in a subject in need thereof or a cell, tissue, or biological sample, binding β-tubulin, inhibiting microtubule assembly, and/or inducing apoptosis in a cancer cell resistant to multiple drugs in a tissue, biological sample, or subject, a method of inducing apoptosis in a cell of a subject, a method of treating and/or preventing a proliferative disease, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression) (e.g., cancer resistant to treatment by one or more microtubule-targeting agents (e.g., taxanes or vinca alkaloids))).

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms.

Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl, e.g., —CF$_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl").

The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$$^{ee}$R", —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$ N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N (R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC (=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, —C(=S)NH(C$_{1-6}$ alkyl), —C(=S)NH$_2$, —C(=O)S (C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoyl phenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy)propanamide, 4-chloro butanamide, 3-methyl-3-nitrobutanamide, o-nitrocinnamide, N-acetyl methionine derivative, o-nitrobenzamide, and o-(benzoyloxy methyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydro thioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butyl phenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonyl methyl carbamate (Tcroc), m-nitrophenyl carbamate, 3,5-dimethoxy benzyl carbamate, o-nitrobenzyl carbamate, 3,4-dimethoxy-6-nitro benzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropyl methyl carbamate, p-decyloxybenzyl carbamate, 2,2-dimethoxyacylvinyl carbamate, o-(N,N-dimethylcarboxamido)benzyl carbamate, 1,1-dimethyl-3-(N, N-dimethylcarboxamido)propyl carbamate, 1,1-dimethylpropynyl carbamate, di(2-pyridyl)methyl carbamate, 2-furanyl methyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxy phenyl) ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6, -trimethyl-4-methoxybenzene sulfonamide (Mtr), 2,4,6-trimethoxybenzenesulfonamide (Mtb), 2,6-dimethyl-4-methoxybenzenesulfonamide (Pme), 2,3,5,6-tetra methyl-4-methoxybenzenesulfonamide (Mte), 4-methoxybenzene sulfonamide (Mbs), 2,4,6-trimethylbenzenesulfonamide (Mts), 2,6-dimethoxy-4-methylbenzenesulfonamide (iMds), 2,2,5,7,8-penta methylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacyl sulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropyl amine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenyl amine (PhF), N-2,7-dichloro-9-fluorenylmethyleneamine, N-ferrocenyl methylamino (Fcm), N-2-picolylamino N-oxide, N-1,1-dimethyl thiomethyleneamine, N-benzylideneamine, N-p-methoxybenzylidene amine, N-diphenylmethyleneamine, N-[(2-pyridyl) mesityl]methylene amine, N—(N',N'-dimethylaminomethylene)amine, N,N'-isopropylidene diamine, N-p-nitrobenzylideneamine, N-salicylideneamine, N-5-chloro salicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-phenyl (pentaacylchromium- or tungsten)acyl]amine, N-copper chelate, N-zinc chelate, N-nitroamine, N-nitrosoamine, amine N-oxide, diphenylphosphin amide (Dpp), dimethylthiophosphinamide (Mpt), diphenylthiophosphin amide (Ppt), dialkyl phosphoramidates, dibenzyl phosphoramidate, diphenyl phosphoramidate, benzenesulfenamide, o-nitrobenzenesulfen amide (Nps), 2,4-dinitrobenzenesulfenamide, pentachloro benzene sulfenamide, 2-nitro-4-methoxybenzenesulfenamide, triphenyl methyl sulfenamide, and 3-nitropyridinesulfenamide (Npys).

Exemplary oxygen atom substituents include, but are not limited to, $-R^{aa}$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetra hydropyranyl, tetrahydrothiopyranyl, 1-methoxycyclohexyl, 4-methoxy tetrahydropyranyl (MTHP), 4-methoxytetrahydrothiopyranyl, 4-methoxy tetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenyl methyl, di(p-methoxyphenyl)phenylmethyl, tri(p-methoxyphenyl)methyl, 4-(4'-bromophenacyloxyphenyl)diphenylmethyl, 4,4',4''-tris(4,5-dichloro phthalimidophenyl)methyl, 4,4',4''-tris(levulinoyloxyphenyl)methyl, 4,4',4''-tris(benzoyloxyphenyl)methyl, 3-(imidazol-1-yl)bis(4',4''dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzo disulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chloro phenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenyl phosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthio methoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis (1,1-dimethylpropyl)phenoxy acetate, chloro diphenylacetate, isobutyrate, monosuccinoate, (E)-2-methyl-2-butenoate, o-(methoxyacyl)benzoate, α-naphthoate, nitrate, alkyl N,N,N',N'-tetra methylphosphorodiamidate, alkyl N-phenylcarbamate, borate, dimethyl phosphinothioyl, alkyl 2,4-dinitrophenylsulfenate, sulfate, methane sulfonate (mesylate), benzylsulfonate, and tosylate (Ts).

Exemplary sulfur atom substituents include, but are not limited to, $-R^{aa}$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain $-C^AH(C^BH_2C^CH_3)-$ includes one chain atom $C^A$, one hydrogen atom on $C^A$, and non-chain substituent $-(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, $-CH(C_2H_5)-$ is a $C_1$ hydrocarbon chain, and

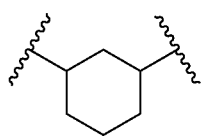 [SMILES: *C1CCCC(*)C1]

is a C₃ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH₂)₄—). A hydrocarbon chain may also be unsaturated and include one or more C=C and/or C≡C bonds anywhere in the hydrocarbon chain. For instance, —CH=CH—(CH₂)₂—, —CH₂—C≡C—CH₂—, and —C≡C—CH=CH— are all examples of a unsubstituted and unsaturated hydrocarbon chain. In certain embodiments, the hydrocarbon chain is unsubstituted (e.g., —C≡C— or —(CH₂)₄—). In certain embodiments, the hydrocarbon chain is substituted (e.g., —CH(C₂H₅)— and —CF₂—). Any two substituents on the hydrocarbon chain may be joined to form an optionally substituted carbocyclyl, optionally substituted heterocyclyl, optionally substituted aryl, or optionally substituted heteroaryl ring. For instance,

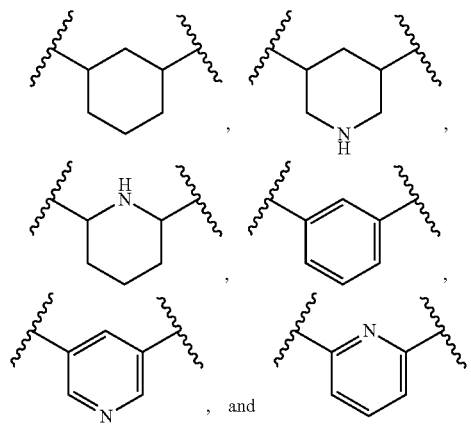

are all examples of a hydrocarbon chain. In contrast, in certain embodiments,

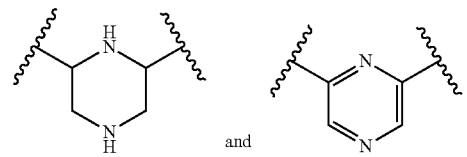 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

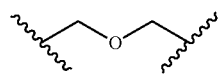 [SMILES: *COC*]

is a C₃ hydrocarbon chain wherein one chain atom is replaced with an oxygen atom. The term "leaving group" is given its ordinary meaning in the art of synthetic organic chemistry and refers to an atom or a group capable of being displaced by a nucleophile. See, for example, Smith, March *Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —OC(=O)SR$^{aa}$, —OC(=O)R$^{aa}$, —OCO₂R$^{aa}$, —OC(=O)N(R$^{bb}$)₂, —OC(=NR$^{bb}$)R$^{aa}$, —OC(=NR$^{bb}$)OR$^{aa}$, —OC(=NR$^{bb}$)N(R$^{bb}$)₂, —OS(=O)R$^{aa}$, —OSO₂R$^{aa}$, —OP(R$^{cc}$)₂, —OP(R$^{cc}$)₃, —OP(=O)₂R$^{aa}$, —OP(=O)(R$^{aa}$)₂, —OP(=O)(OR$^{cc}$)₂, —OP(=O)₂N(R$^{bb}$)₂, and —OP(=O)(NR$^{bb}$)₂, wherein R$^{aa}$, R$^{bb}$, and R$^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)₂(CF₂)₃CF₃ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference for the subject matter and purpose referenced herein. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy) alkyl esters or ((alkoxycarbonyl) oxy) alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" as used herein refers to a human (i.e., a male or a female of any age group, e.g., a pediatric subject (e.g., an infant, child, or an adolescent) or an adult subject (e.g., a young adult, a middle-aged adult, or a senior adult)). The subject may also include any non-human animals including, but not limited to a cynomolgus monkey or a rhesus monkey, a cattle, a pig, a horse, a sheep, a goat, a cat, a dog, a mouse, a rat, a rabbit, or a bird (e.g., a commercially relevant bird, such as a chicken, a duck, a goose, or a turkey). In certain embodiments, the non-human animal is a fish, a reptile, or an amphibian. In certain embodiments, the non-human animal is a mammal, a primate, a rodent, an avian, an equine, an ovine, a bovine, a caprine, a feline, or a canine. The non-human animal may be a male or a female at any stage of development. The non-human animal may be a transgenic animal or a genetically engineered animal. A "patient" refers to a human subject in need of treatment of a disease. The subject may also be a plant.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition (therapeutically or prophylactically). As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay, minimize, or abolish one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The present invention provides exemplary anti-cancer agents in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration is achieved in various ways. In some formulations, the agents are systemic after administration; in others, the agent is localized by virtue of the formulation, such as the use of an implant that acts to retain the active dose at the site of implantation.

As used herein, the terms "determining," "assessing," "assaying," "measuring," and "detecting" refer to both quantitative and qualitative determinations and as such, the term "determining" is used interchangeably herein with "assaying," "measuring," and the like. Where a quantitative determination is intended, the phrase "determining an amount" and the like is used. Where either a qualitative or quantitative determination is intended, the phrase "determining a level" or "detecting a level" is used.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The terms "alanine aminotransferase" and "ALT" are used interchangeably. The terms "aspartate transaminase" and "AST" are used interchangeably. The terms "Bcl-2-associated X protein" and "BAX" are used interchangeably. The term "BUN" refers to blood urea nitrogen; the term "CBSI" refers to Colchicine binding site inhibitor; and the term "Cre" refers to creatinine. The term "Cyto.C" refers to cytochrome C; the term "DAPI" refers to 4',6-diamidino-2-phenylindole. The term "GAPDH" refers to Glyceraldehyde-3-Phosphate Dehydrogenase; the term "HFB" refers to Human Fibroblast; and the term "NBE" refers to human normal bronchial epithelial cell. The term "NSCLC" refers to non-small cell lung cancer; the term "MDR" refers to multidrug resistance; the term "Mito." refers to mitochondria; and the term "MTCO1" refers to Mitochondrially Encoded Cytochrome C Oxidase I. The term "MTS" refers to 3-(4,5-dimethylthiazol-2-yl)-5-(3-carboxymethoxyphenyl)-2-(4-sulfophenyl)-2H-tetrazolium; the term "PARP" refers to poly[ADP-ribose] polymerase; the term "P-gp" refers to P-glycoprotein; the term "p-HH3" refers to phospho-histone H3; and the term "PI" refers to propidium iodide. The term "RF" refers to resistance factor; the term "RU" refers to resonance units; and the term "SPR" refers to surface plasmon resonance. The term "TNBC" refers to triple-negative breast cancer; the term "TKI" refers to tyrosine kinase inhibitor; and the term "TUNEL" refers to Terminal deoxynucleotidyl transferase dUTP nick end labeling.

The term "microtubule-targeting agent" or "MTA" refers to an agent that targets and interferes with cancer cell microtubules, regulate the dynamics of cancer cell microtubules and, consequently, cause mitotic arrest and subsequently cell apoptosis. Exemplary microtubule-targeting agents include, but are not limited to, microtubule stabilizers (MSAs) and destabilizers (MDAs). Exemplary microtubule stabilizers include, but are not limited to, taxanes and vinca alkaloids.

The details of one or more embodiments of the disclosure are set forth herein. Other features, objects, and advantages of the disclosure will be apparent from the Detailed Description, the Examples, and the Claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) the cytotoxic effects of exemplary compound AS1712 on different non-small cell lung cancer and normal lung cell lines (cells were treated with exemplary compound AS1712 for 72 hours, and cell viability was examined by the MTS assay; data are the mean of three determinations); (FIGS. 1B and 1C) CL1-0 cells were treated with AS1712 (12.5-200 nM) for 14 days (the colonies were fixed, stained with crystal violet, and then counted; data are the mean±SD; *p<0.05); (FIGS. 1D and 1E) H1975 cells were treated with AS1712 (12.5-200 nM) for 14 days (the colonies were fixed, stained with crystal violet, and then counted; data are the mean±SD; *p<0.05); and (FIG. 1F) H1975 cells ($2 \times 10^6$) were subcutaneously injected into BALB/c nude mice (mice were treated with DMSO or with 4 or 8 mg/kg of AS1712 intraperitoneally three times a week for the next 25 days; tumor volumes were measured before each injection; data are the mean±SEM; *p<0.05).

(FIG. 4A) pro-apoptotic protein expression was detected by immunoblotting; (FIG. 4B) cytochrome c levels were assessed in the cytosolic and mitochondrial fractions; (FIG. 4C) cells were stained with propidium iodide to determine their DNA content by flow cytometry; (FIG. 4D) proteins were immunoblotted to examine their expression levels; and (FIG. 4E) cells were subjected to high-content imaging by p-HH3 staining to calculate the population of mitotic cells (data are the mean±SD; *p<0.05); (FIG. 4F) cells were treated with AS1712 for 6 h to observe mitotic spindle organization by α-tubulin staining (green), wherein immunofluorescence was detected by confocal laser microscopy, and nuclei were detected by DAPI staining (blue).

(FIG. 6A) cells were incubated with AS1712 for 6-h prior to examining the microtubule networks as α-tubulin staining (green), wherein nuclei were detected by DAPI staining (blue); (FIG. 6B) cells were incubated with DMSO, AS1712, paclitaxel, or nocodazole for 6-h and then harvested and separated into soluble (tubulin monomers) and insoluble (tubulin polymers) fractions, wherein the amount of α-tubulin was detected by immunoblotting; (FIG. 6C) immunofluorescence-based microtubule polymerization assay H1975 cells were treated with 40 nM AS1712 for 1 h, after cold exposure for 30 min, and then were incubated at 37° C. for the indicated times; (FIG. 6D) purified porcine tubulin and GTP were incubated at 37° C. with 5 µM AS1712, 5 µM paclitaxel, 5 µM vincristine, 5 µM nocodazole, or with DMSO control, wherein microtubule polymerization was assessed every min for 1 h by monitoring the $A_{340}$; (FIG. 6E) purified centrosomes were first incubated with AS1712 and then with tubulin, wherein microtubule asters that formed were stained with monoclonal anti-α-tubulin (green), fiber lengths were measured (n=20 asters per group), and data are the mean±SD.

(FIG. 9A) H1975 cell lysates were incubated with mag-beads-control or AS1712 overnight and precipitated proteins were detected by immunoblotting; (FIG. 9B) binding affinity of AS1712 to tubulin as measured by surface plasmon resonance; (FIGS. 9C and 9D) tubulin (1 mg/mL) was incubated with 100 µM of nocodazole, vincristine, AS1712, or DMSO control for 30 min at 30° C., and then, the samples were subjected to trypsin digestion for 10 min on ice, wherein the positions of the tryptic cleavage products, αN, αC, and β-col, are shown to the right of the gel, and data are the mean±SD; (FIG. 9E) colchicine competition assay: AS1712 and nocodazole decreased the fluorescence of the colchicine-tubulin complex, wherein data are the mean±SD; (FIG. 9F) superimposition of the docked AS1712-tubulin (orange) and colchicine-tubulin complexes (purple); (FIG. 9G) interactions between the tubulin heterodimer and AS1712; (FIG. 9H) schematic of the AS1712 and tubulin-residue interactions.

(FIG. 10A) KBtax ($1\times10^7$) cells were subcutaneously injected into BALB/c nude mice, mice were treated with DMSO, paclitaxel (15 mg/kg), or RJ-LC-15-8 (8 mg/kg) intraperitoneally three times a week for 21 days, and the tumor volume was measured before each treatment, wherein data are shown as the mean±SEM; (FIG. 10B) tumor slices were histologically stained with hematoxylin and eosin (H&E), and the cell apoptosis status was determined by TUNEL staining; (FIG. 10C) Rhodamine efflux assay for P-gp pumping activity; (FIG. 10D) samples of KBtax cells were treated with one of the indicated concentrations of RJ-LC-15-8 for 24 h and then harvested to assess expression of the indicated proteins; (FIG. 10E) the microtubule networks and mitotic spindle organization in KBtax cells after a 6-hour treatment with 30 nM RJ-LC-15-8.

DETAILED DESCRIPTION OF THE PREFERRED EMBODIMENT

Figure 1A:
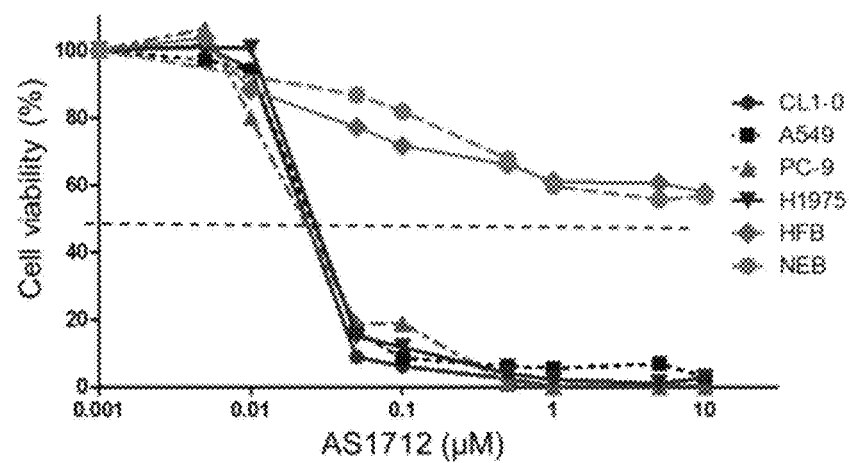
FIGS. 1A to 1F show that exemplary compound AS1712 inhibits cancer cell proliferation in vitro and in vivo.
Figure 1B:
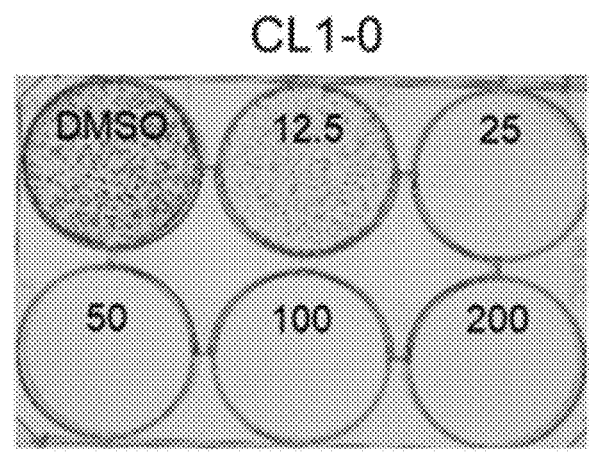
Figure 1C:
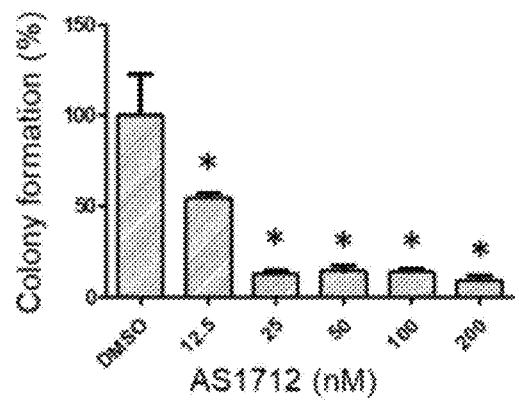
Figure 1D:
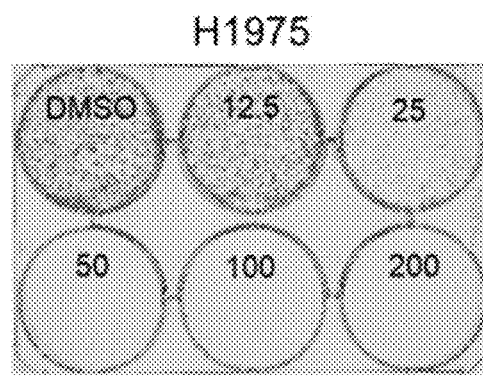
Figure 1E:
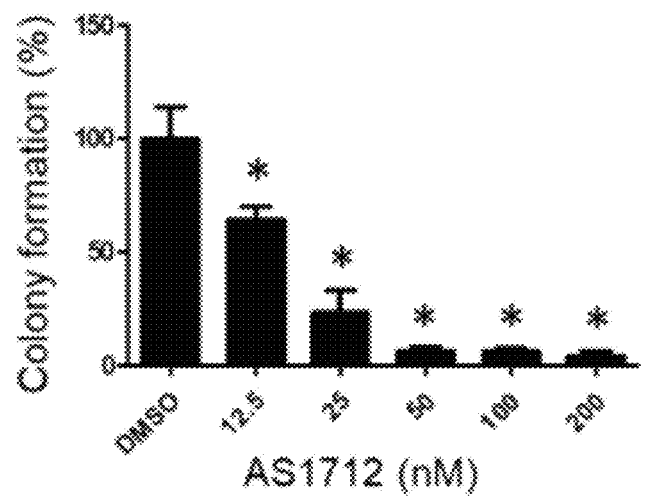
Figure 1F:
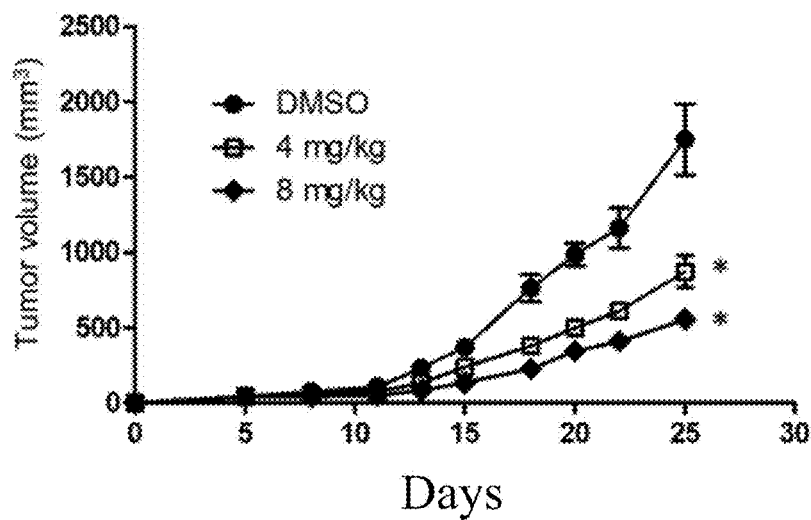

The present disclosure provides 4(1H)-quinolone derivatives for treating target proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression)). The cancers described herein may be resistant to treatment by one or more microtubule-targeting agents (e.g., taxanes or vinca alkaloids). The compounds described herein are useful in treating, delaying, and/or preventing proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression) (e.g., cancer resistant to treatment by one or more microtubule-targeting agents (e.g., taxanes or vinca alkaloids))), and/or inhibiting polymerization of a cancer cell microtubule in a subject in need thereof or a cell, tissue, or biological sample, binding β-tubulin, inhibiting microtubule assembly, and/or inducing apoptosis in a cancer cell resistant to multiple drugs in a tissue, biological sample, or subject. Also provided in the present disclosure are pharmaceutical compositions, kits, and methods of using the compounds for inhibiting polymerization of a cancer cell microtubule in a subject in need thereof or a cell, tissue, or biological sample, binding β-tubulin, inhibiting microtubule assembly, and/or inducing apoptosis in a cancer cell resistant to multiple drugs in a tissue, biological sample, or subject, and for treating any of the target proliferative diseases described herein.

Compounds

In one aspect, disclosed are compounds of Formula (I):

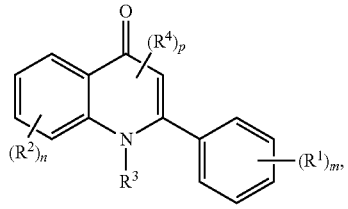

or a pharmaceutically acceptable salt thereof, wherein: $R^1$, $R^2$, $R^3$, $R^4$, m, n, and p are as described herein. In certain embodiments, a compound described herein is of Formula (I):

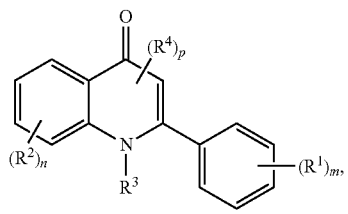

or a pharmaceutically acceptable salt thereof. In certain embodiments, the pharmaceutically acceptable salt is a mesylate salt. In certain embodiments, the pharmaceutically acceptable salt is a salt of MsOH. In certain embodiments, the pharmaceutically acceptable salt is a salt of $CH_3SO_2OH$.

In certain embodiments, a compound of Formula (I) is of Formulae (IA), (IB), or (IC):

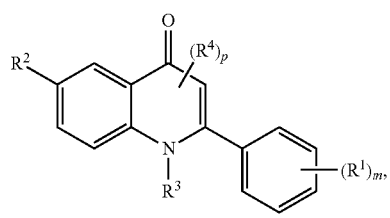

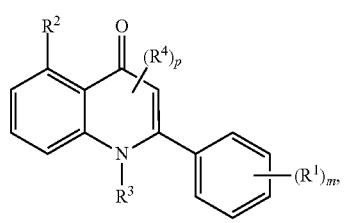

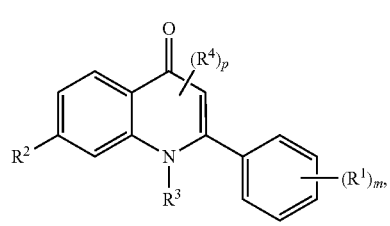

or a pharmaceutically acceptable salt, co-crystal, tautomer, stereoisomer, solvate, hydrate, polymorph, isotopically enriched derivative, or prodrug thereof, wherein $R^1$, $R^2$, $R^3$, $R^4$, m, and p are as described herein.

In some embodiments, Formula (I) includes zero or more instances of substituent $R^1$. In some embodiments, Formula (I) includes zero instances of substituent $R^1$. In some embodiments, Formula (I) includes one or more instances of substituent $R^1$. In certain embodiments, m is 0. In certain embodiments, m is 1. In certain embodiments, m is 2. In certain embodiments, m is 3. In certain embodiments, m is 4. In certain embodiments, m is 5. In certain embodiments, n is 4. In certain embodiments, at least one instance of $R^1$ is halogen (e.g., F, Cl, Br, or I). In certain embodiments, at least one instance of $R^1$ is bromo. In certain embodiments, at least one instance of $R^1$ is fluoro. In certain embodiments, at least one instance of $R^1$ is chloro. In certain embodiments, at least one instance of $R^1$ is iodo.

In certain embodiments, at least one instance of $R^1$ is —C(=O)(optionally substituted alkyl) (e.g., —C(=O)(optionally substituted $C_{1-6}$ alkyl)). In certain embodiments, at least one instance of $R^1$ is optionally substituted alkyl (e.g., optionally substituted $C_{1-6}$ alkyl). In certain embodiments, at least one instance of $R^1$ is optionally substituted $C_{1-6}$ alkyl (e.g., optionally substituted, methyl, ethyl, or propyl). In certain embodiments, at least one instance of $R^1$ is alkyl optionally substituted with halogen. In certain embodiments, at least one instance of $R^1$ is $C_{1-6}$ alkyl optionally substituted with halogen. In certain embodiments, at least one instance of $R^1$ is —$CF_3$.

In certain embodiments, at least one instance of $R^1$ is optionally substituted alkenyl (e.g., optionally substituted $C_2$-$C_6$ alkenyl). In certain embodiments, at least one instance of $R^1$ is optionally substituted alkynyl (e.g., optionally substituted $C_2$-$C_{10}$ alkynyl (e.g., optionally substituted, propynyl or butynyl)). In certain embodiments, at least one instance of $R^1$ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of $R^1$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of $R^1$ can be optionally substituted aryl (e.g., phenyl, or benzyl). In some embodiments, at least one instance of $R^1$ can be optionally substituted heteroaryl (e.g., 5- to 7-membered monocyclic heteroaryl, wherein one, two, three, or four atoms in the heteroaryl ring system are independently nitrogen, oxygen, or sulfur; or optionally substituted 8- to 10-membered bicyclic heteroaryl, wherein one, two, three, or four atoms in the heteroaryl ring system are independently nitrogen, oxygen, or sulfur). In some embodiments, at least one instance of $R^1$ can be —CN. In certain embodiments, at least one instance of $R^1$ is —$OR^{D1}$, —$N(R^{D1a})_2$, or —$SR^{D1}$, and $R^{D1}$ is as defined herein. In some embodiments, at least one instance of $R^1$ can be —$OR^{D1}$, —$N(R^{D1a})_2$, or —$SR^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring. In some embodiments, at least one instance of $R^1$ can be —$OR^{D1}$ (e.g., —OH or —OMe). In some embodiments, at least one instance of $R^1$ can be —$OR^{D1}$, and $R^{D1}$ is hydrogen or optionally substituted alkyl. In some embodiments, at least one instance of $R^1$ is —OH, —OMe, or of formula:

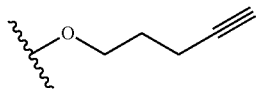

In some embodiments, at least one instance of $R^1$ is —OH. In some embodiments, at least one instance of $R^1$ is —O(optionally substituted alkyl) (e.g., —O(optionally substituted $C_{1-6}$ alkyl)). In certain embodiments, at least one instance of $R^1$ is —O(optionally substituted $C_{1-6}$ alkyl) (e.g., —O(optionally substituted methyl), —O(optionally substituted ethyl), or optionally substituted propyl)). In certain embodiments, at least one instance of $R^1$ is —OMe. In certain embodiments, at least one instance of $R^1$ is of formula: —$O(CH_2)_y(R^{1a})$, wherein y is 1, 2, 3, 4, 5, or 6; and $R^{1a}$ is halogen, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^1$ is of formula: —$O(CH_2)_y(R^{1a})$, wherein y is 1, 2, 3, or 4; and $R^{1a}$ is halogen, optionally substituted alkenyl, or optionally substituted alkynyl. In some embodiments, at least one instance of $R^1$ is of formula:

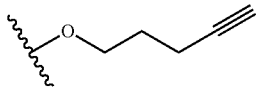

In certain embodiments, at least one instance of $R^1$ is of formula: —O(alkyl optionally substituted with alkynyl). In certain embodiments, at least one instance of $R^1$ is of formula: —O($C_{1-6}$ alkyl optionally substituted with alkynyl). In some embodiments, at least one instance of $R^1$ can be —$N(R^{D1a})_2$ (e.g., —$NH_2$ or —$NMe_2$). In some embodiments, at least one instance of $R^1$ can be —$SR^{D1}$ (e.g., —SH or —SMe).

In certain embodiments, $R^{D1}$ is hydrogen. In certain embodiments, $R^{D1}$ is optionally substituted acyl (e.g., —C(=O)Me). In certain embodiments, $R^{D1}$ is optionally substituted alkyl (e.g., substituted or unsubstituted $C_{1-6}$ alkyl). In certain embodiments, $R^{D1}$ is substituted or unsubstituted methyl. In certain embodiments, $R^{D1}$ is substituted or unsubstituted ethyl. In certain embodiments, $R^{D1}$ is substituted or unsubstituted propyl. In certain embodiments, $R^{D1}$ is optionally substituted alkenyl (e.g., substituted or unsubstituted $C_{2-6}$ alkenyl). In certain embodiments, $R^{D1}$ is optionally substituted alkynyl (e.g., substituted or unsubstituted $C_{2-6}$ alkynyl). In certain embodiments, $R^{D1}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{D1}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is optionally substituted aryl (e.g., substituted or unsubstituted, 6- to 10-membered aryl). In certain embodiments, $R^{D1}$ is benzyl. In certain embodiments, $R^{D1}$ is optionally substituted phenyl. In certain embodiments, $R_{D1}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is an oxygen protecting group when attached to an oxygen atom. In certain embodiments, $R^{D1}$ is a sulfur protecting group when attached to a sulfur atom.

In certain embodiments, at least one instance of $R^{D1a}$ is hydrogen. In certain embodiments, at least one instance of $R^{D1a}$ is optionally substituted acyl (e.g., —C(=O)Me). In certain embodiments, at least one $R^{D1a}$ is optionally substituted alkyl (e.g., substituted or unsubstituted $C_{1-6}$ alkyl). In certain embodiments, at least one instance of $R^{D1a}$ is substituted or unsubstituted methyl. In certain embodiments, at least one instance of $R^{D1a}$ is substituted or unsubstituted ethyl. In certain embodiments, at least one instance of $R^{D1a}$ is substituted or unsubstituted propyl. In certain embodiments, at least one instance of $R^{D1a}$ is optionally substituted alkenyl (e.g., substituted or unsubstituted $C_{2-6}$ alkenyl). In certain embodiments, at least one instance of $R^{D1a}$ is optionally substituted alkynyl (e.g., substituted or unsubstituted $C_{2-6}$ alkynyl). In certain embodiments, at least one instance of $R^{D1a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D1a}$ is optionally substituted aryl (e.g., substituted or unsubstituted, 6- to 10-membered aryl). In certain embodiments, at least one instance of $R^{D1a}$ is benzyl. In certain embodiments, at least one instance of $R^{D1a}$ is optionally substituted phenyl. In certain embodiments, at least one instance of $R^{D1a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In some embodiments, Formula (I) includes zero or more instances of substituent $R^2$. In some embodiments, Formula (I) includes zero instances of substituent $R^2$. In some embodiments, Formula (I) includes one or more instances of substituent $R^2$. In certain embodiments, n is 0. In certain embodiments, n is 1. In certain embodiments, n is 2. In certain embodiments, n is 3. In certain embodiments, n is 4. In certain embodiments, at least one instance of $R^2$ is halogen (e.g., F, Cl, Br, or I).

In certain embodiments, at least one instance of $R^2$ is optionally substituted acyl (e.g., —C(=O)(alkyl)). In certain embodiments, at least one instance of $R^2$ is of formula: —C(=O)OR$^{2a}$, —C(=O)N(R$^{2b}$)$_2$, or —(CH$_2$)$_x$OR$^{2a}$; and x is 0, 1, 2, 3, 4, 5, or 6; $R^{2a}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; each instance of $R^{2b}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, $R_{2a}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), methanesulfonate (mesylate), benzylsulfonate, or tosylate (Ts)).

In certain embodiments, $R^{2a}$ is hydrogen. In certain embodiments, $R^{2a}$ is optionally substituted alkyl (e.g., substituted or unsubstituted $C_{1-6}$ alkyl). In certain embodiments, $R^{2a}$ is optionally substituted alkenyl (e.g., substituted or unsubstituted $C_{2-6}$ alkenyl). In certain embodiments, $R^{2a}$ is optionally substituted alkynyl (e.g., substituted or unsubstituted $C_{2-6}$ alkynyl). In certain embodiments, $R^{2a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{2a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{2a}$ is optionally substituted aryl (e.g., substituted or unsubstituted, 6- to 10-membered aryl). In certain embodiments, $R^{2a}$ is benzyl. In certain embodiments, $R^{2a}$ is optionally substituted phenyl. In certain embodiments, $R^{2a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{2a}$ is an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, tbutyldimethylsilyl (TBDMS), t-butyldiphenylsilyl (TBDPS), methanesulfonate (mesylate), benzylsulfonate, or tosylate (Ts)). In certain embodiments, at least one instance of $R^{2b}$ is hydrogen. In certain embodiments, at least one instance of $R^{2b}$ is optionally substituted alkyl (e.g., substituted or unsubstituted $C_{1-6}$ alkyl). In certain embodiments, at least one instance of $R^{2b}$ is optionally substituted alkenyl (e.g., substituted or unsubstituted $C_{2-6}$ alkenyl). In certain embodiments, at least one instance of $R^{2b}$ is optionally substituted alkynyl (e.g., substituted or unsubstituted $C_{2-6}$ alkynyl). In certain embodiments, at least one instance of $R^{2b}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{2b}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{2b}$ is optionally substituted aryl (e.g., substituted or unsubstituted, 6- to 10-membered aryl). In certain embodiments, at least one instance of $R^{2b}$ is benzyl. In certain embodiments, at least one instance of $R^{2b}$ is optionally substituted phenyl. In certain embodiments, at least one instance of $R^{2b}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{2b}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, at least one instance of $R^2$ is —C(=O)OR$^{2a}$, and $R^{2a}$ is hydrogen, optionally substituted alkyl, optionally substituted alkenyl, or optionally substituted alkynyl. In certain embodiments, at least one instance of $R^2$ is —C(=O)OR$^{2a}$, and $R^{2a}$ is hydrogen or optionally substituted $C_{1-6}$ alkyl. In certain embodiments, at least one instance of $R^2$ is —C(=O)OH, —C(=O)OMe, —C(=O)OEt, —C(=O)O(iPr), —C(=O)(OCH$_2$CH$_2$)$_3$OH, or —C(=O)(OCH$_2$CH$_2$)$_4$OH. In certain embodiments, at least one instance of $R^2$ is —C(=O)OH. In certain embodiments, at least one instance of $R^2$ is —C(=O)O(unsubstituted $C_{1-6}$ alkyl). In certain embodiments, at least one instance of $R^2$ is —C(=O)OMe. In certain embodiments, at least one instance of $R^2$ is —C(=O)OEt. In certain embodiments, at least one instance of $R^2$ is —C(=O)O(propyl). In certain embodiments, at least one instance of $R^2$ is —C(=O)O(n-propyl). In certain embodiments, at least one instance of $R^2$ is —C(=O)O(iPr). In certain embodiments, at least one instance of $R^2$ is —C(=O)O(butyl). In certain embodiments, at least one instance of $R^2$ is —C(=O)O(n-butyl). In certain embodiments, at least one instance of $R^2$ is —C(=O)O(pentyl). In certain embodiments, at least one instance of $R^2$ is —C(=O)(OCH$_2$CH$_2$)$_z$O(R$^{2c}$), wherein z is 1, 2, 3, 4, 5, or 6, and $R^{2c}$ is hydrogen, optionally substituted alkyl, optionally substituted alkenyl, or optionally substituted alkynyl. In certain embodiments, z is 1. In certain embodiments, z is 2. In certain embodiments, z is 3. In certain embodiments, z is 4. In certain embodiments, z is 5. In certain embodiments, z is 6. In certain embodiments, at least one instance of $R^2$ is —C(=O)(OCH$_2$CH$_2$)$_z$O(R$^{2c}$), wherein z is 2, 3, 4, 5, or 6, and $R^{2c}$ is hydrogen or optionally substituted $C_{1-6}$ alkyl. In certain embodiments, at least one instance of $R^2$ is —C(=O)(OCH$_2$CH$_2$)$_3$OH. In certain embodiments, at least one instance of $R^2$ is —C(=O)(OCH$_2$CH$_2$)$_4$OH.

In certain embodiments, at least one instance of $R^2$ is —C(=O)N(R$^{2b}$)$_2$, and each instance of $R^{2b}$ is independently hydrogen, optionally substituted alkyl, optionally substituted alkenyl, or optionally substituted alkynyl. In certain embodiments, at least one instance of $R^2$ is —C(=O)NH(R$^{2b}$), and $R^{2b}$ is optionally substituted $C_{1-6}$ alkyl. In certain embodiments, at least one instance of $R^2$ is —C(=O)NH(R$^{2b}$), and $R^{2b}$ is unsubstituted $C_{1-6}$ alkyl. In certain embodiments, at least one instance of $R^2$ is —C(=O)NH(Me). In certain embodiments, at least one instance of $R^2$ is —C(=O)NH(Et). In certain embodiments, at least one instance of $R^2$ is —C(=O)NH(n-propyl). In certain embodiments, at least one instance of $R^2$ is —C(=O)NH(i-Pr). In certain embodiments, at least one instance of $R^2$ is —C(=O)NH(butyl). In certain embodiments, at least one instance of $R^2$ is —C(=O)NH(n-butyl). In certain embodiments, at least one instance of $R^2$ is —C(=O)NH(pentyl).

In certain embodiments, at least one instance of $R^2$ is —(CH$_2$)$_x$OR$^{2a}$, x is 1, 2, 3, 4, or 5, and $R^{2a}$ is optionally substituted $C_{1-6}$ alkyl. In certain embodiments, at least one instance of $R^2$ is —(CH$_2$)$_x$OR$^{2a}$, x is 1, 2, 3, 4, or 5, and $R^{2a}$ is unsubstituted $C_{1-6}$ alkyl. In certain embodiments, at least one instance of $R^2$ is —(CH$_2$)OMe. In certain embodiments, at least one instance of $R^2$ is —(CH$_2$)OEt. In certain embodiments, at least one instance of $R^2$ is —(CH$_2$)O(propyl). In certain embodiments, at least one instance of $R^2$ is —(CH$_2$)O(n-propyl). In certain embodiments, at least one instance of $R^2$ is —(CH$_2$)O(i-propyl). In certain embodiments, at least one instance of $R^2$ is —(CH$_2$)O(butyl). In certain embodiments, at least one instance of $R^2$ is —(CH$_2$)O(n-butyl). In certain embodiments, at least one instance of $R^2$ is —(CH$_2$)O(pentyl).

In certain embodiments, at least one instance of $R^2$ is optionally substituted alkyl (e.g., optionally substituted $C_{1-6}$ alkyl). In certain embodiments, at least one instance of $R^2$ is optionally substituted $C_{1-6}$ alkyl (e.g., optionally substituted, methyl, ethyl, or propyl). In certain embodiments, at least one instance of $R^2$ is optionally substituted alkenyl (e.g., optionally substituted $C_2$-$C_6$ alkenyl). In certain embodiments, at least one instance of $R^2$ is optionally substituted alkynyl (e.g., optionally substituted $C_2$-$C_{10}$ alkynyl (e.g., optionally substituted, propynyl or butynyl)). In certain embodiments, at least one instance of $R^2$ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of $R^2$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of $R^2$ can be optionally substituted aryl (e.g., phenyl, or benzyl). In some embodiments, at least one instance of $R^2$ can be optionally substituted heteroaryl (e.g., 5- to 7-membered monocyclic heteroaryl, wherein one, two, three, or four atoms in the heteroaryl ring system are independently nitrogen, oxygen, or sulfur; or optionally substituted 8- to 10-membered bicyclic heteroaryl, wherein one, two, three, or four atoms in the heteroaryl ring system are independently nitrogen, oxygen, or sulfur). In some embodiments, at least one instance of $R^2$ can be —CN. In certain embodiments, at least one instance of $R^2$ is —OR$^{D1}$, —N(R$^{D1a}$)$_2$, or —SR$^{D1}$, and $R^{D1}$ is as defined herein. In some embodiments, at least one instance of $R^2$ can be —OR$^{D1}$, —N(R$^{D1a}$)$_2$, or —SR$^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring. In some embodiments, at least one instance of $R^2$ can be —OR$^{D1}$ (e.g., —OH or —OMe). In some embodiments, at least one instance of $R^2$ can be —N(R$^{D1a}$)$_2$ (e.g., —NH$_2$ or —NMe$_2$). In some embodiments, at least one instance of $R^2$ can be —SR$^{D1}$ (e.g., —SH or —SMe).

Formula (I) includes substituent $R^3$. In some embodiments, $R^3$ is hydrogen. In some embodiments, $R^3$ is optionally substituted alkyl. In some embodiments, $R^3$ is optionally substituted $C_{1-6}$ alkyl. In certain embodiments, $R^3$ is $C_1$-$C_6$ alkyl optionally substituted with halogen (e.g., F, Cl, Br, or I). In some embodiments, $R^3$ is unsubstituted alkyl. In some embodiments, $R^3$ is unsubstituted $C_1$-$C_6$ alkyl (e.g., unsubstituted methyl, unsubstituted ethyl, unsubstituted propyl, unsubstituted butyl). In certain embodiments, $R^3$ is unsubstituted methyl. In certain embodiments, $R^3$ is unsubstituted ethyl. In certain embodiments, $R^3$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In some embodiments, Formula (I) includes zero or more instances of substituent $R^4$. In some embodiments, Formula (I) includes zero instances of substituent $R^4$. In some embodiments, Formula (I) includes one instance of substituent $R^4$. In certain embodiments, p is 0. In certain embodiments p is 1. In certain embodiments, at least one instance of $R^4$ is halogen (e.g., F, Cl, Br, or I). In certain embodiments, at least one instance of $R^4$ is optionally substituted acyl (e.g., —C(=O)(alkyl)).

In certain embodiments, at least one instance of $R^4$ is optionally substituted alkyl (e.g., optionally substituted $C_{1-6}$ alkyl). In certain embodiments, at least one instance of $R^4$ is optionally substituted $C_{1-6}$ alkyl (e.g., optionally substituted, methyl, ethyl, or propyl). In certain embodiments, at least one instance of $R^4$ is optionally substituted alkenyl (e.g., optionally substituted $C_2$-$C_6$ alkenyl). In certain embodiments, at least one instance of $R^4$ is optionally substituted alkynyl (e.g., optionally substituted $C_2$-$C_{10}$ alkynyl (e.g., optionally substituted, propynyl or butynyl)). In certain embodiments, at least one instance of $R^4$ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of $R^4$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of $R^4$ can be optionally substituted aryl (e.g., phenyl, or benzyl). In some embodiments, at least one instance of $R^4$ can be optionally substituted heteroaryl (e.g., 5- to 7-membered monocyclic heteroaryl, wherein one, two, three, or four atoms in the heteroaryl ring system are independently nitrogen, oxygen, or sulfur; or optionally substituted 8- to 10-membered bicyclic heteroaryl, wherein one, two, three, or four atoms in the heteroaryl ring system are independently nitrogen, oxygen, or sulfur). In some embodiments, at least one instance of $R^4$ can be —CN. In certain embodiments, at least one instance of $R^4$ is —$OR^{D1}$, —$N(R^{D1a})_2$, or —$SR^{D1}$, and $R^{D1}$ is as defined herein. In some embodiments, at least one instance of $R^4$ can be —$OR^{D1}$, —$N(R^{D1a})_2$, or —$SR^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring. In some embodiments, at least one instance of $R^4$ can be —$OR^{D1}$ (e.g., —OH or —OMe). In some embodiments, at least one instance of $R^4$ can be —$N(R^{D1a})_2$ (e.g., —$NH_2$ or —$NMe_2$). In some embodiments, at least one instance of $R^4$ can be —$SR^{D1}$ (e.g., —SH or —SMe).

In some embodiments, a compound described herein is of Formula (I):

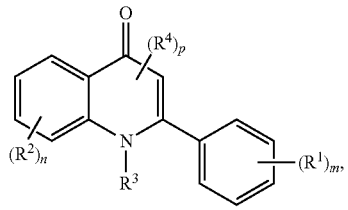

(I)

or a pharmaceutically acceptable salt, co-crystal, tautomer, stereoisomer, solvate, hydrate, polymorph, isotopically enriched derivative, or prodrug thereof, wherein:

each instance of $R^1$ is independently halogen, —C(=O) (optionally substituted alkyl); optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$;

each instance of $R^2$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$;

$R^3$ is hydrogen, optionally substituted alkyl, or a nitrogen protecting group;

each instance of $R^4$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$;

$R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring;

m is 0, 1, 2, 3, 4, or 5;

n is 0, 1, 2, 3, or 4; and p is 0 or 1.

In some embodiments, at least one of m and n is not 0.

In some embodiments, the compound of Formula (I) can be of one of the following formulae:

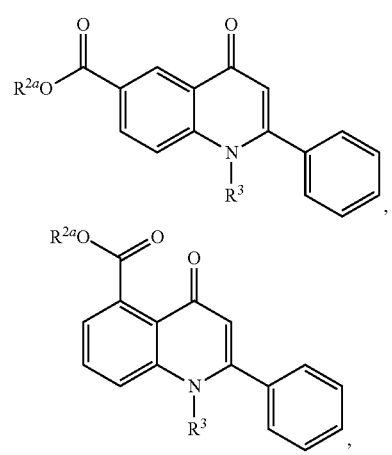

-continued
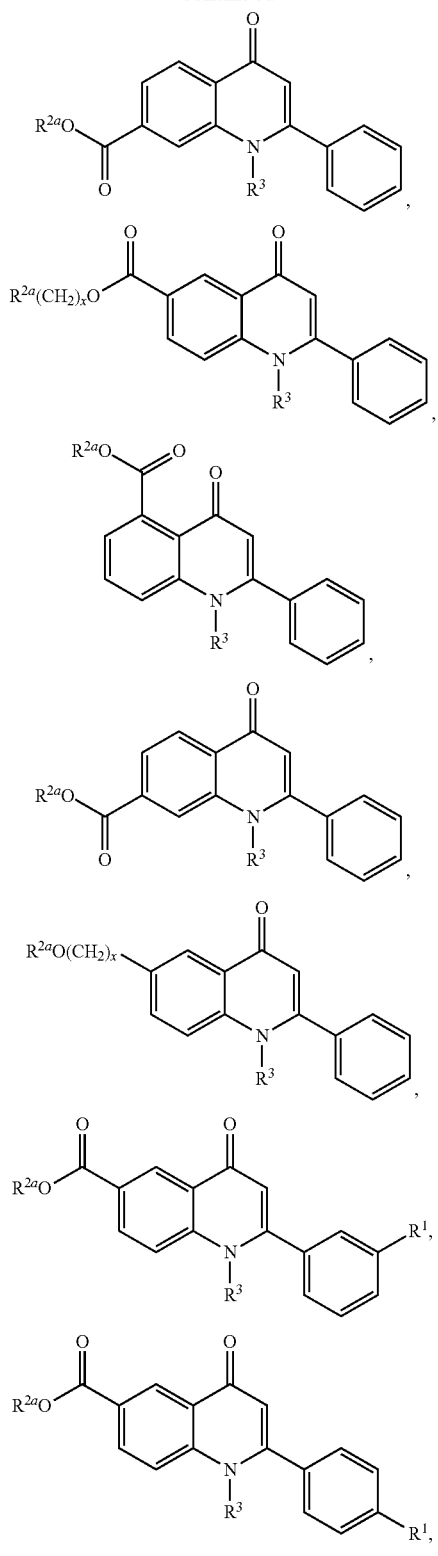
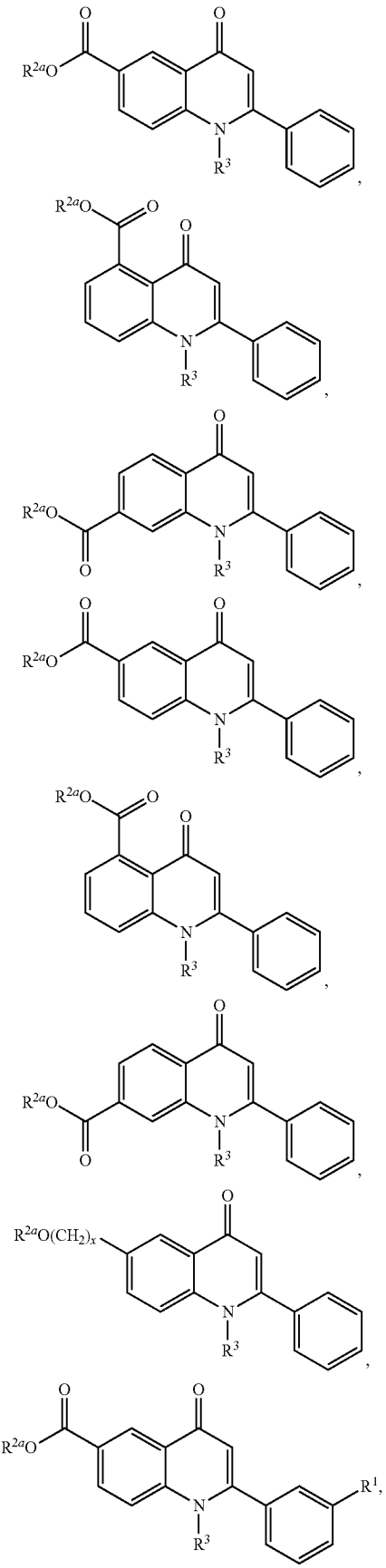
or a pharmaceutically acceptable salt, co-crystal, tautomer, stereoisomer, solvate, hydrate, polymorph, isotopically enriched derivative, or prodrug thereof.
In some embodiments, the compound of Formula (I) can be of one of the following formulae:

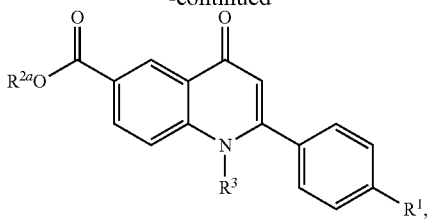

or a pharmaceutically acceptable salt thereof.

Exemplary compounds of Formula (I) are provided herein. In some embodiments, the compound of Formula (I) is a compound of any one of Examples 1-2. In some embodiments, the compound of Formula (I) is a compound of Table 3. In some embodiments, the compound of Formula (I) is a compound of Table 7. In some embodiments, the compound of Formula (I) can be of one of the following formulae:

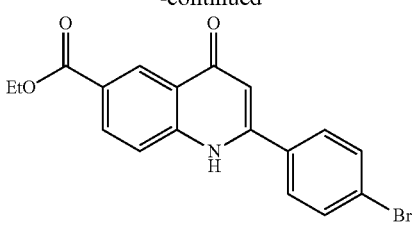
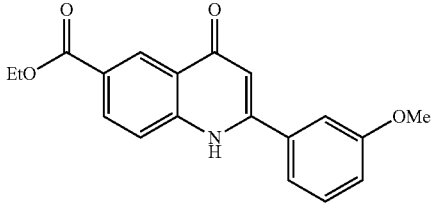
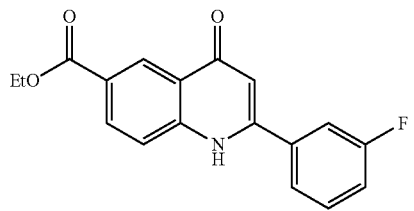
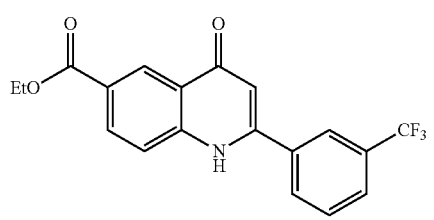
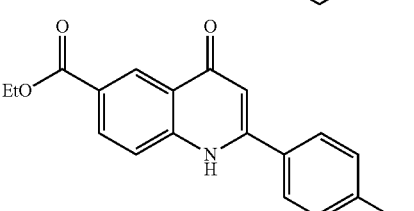
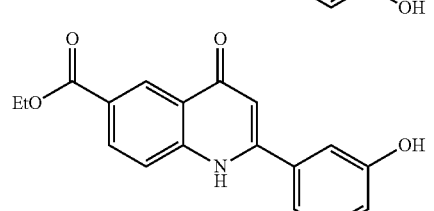
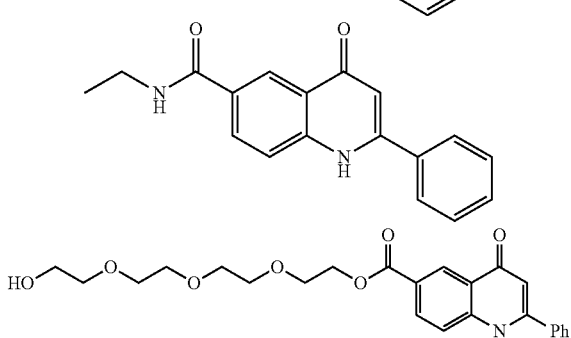
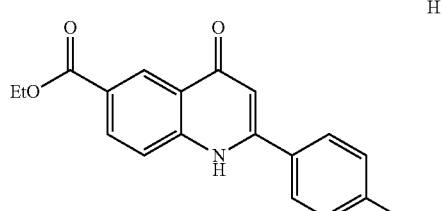
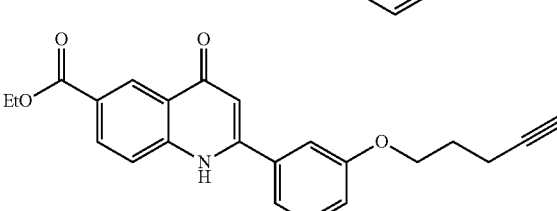
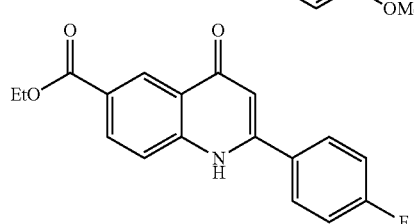
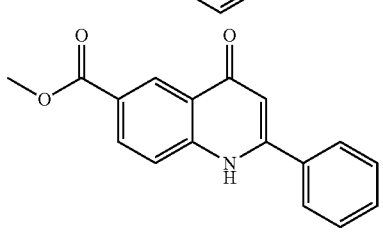

-continued
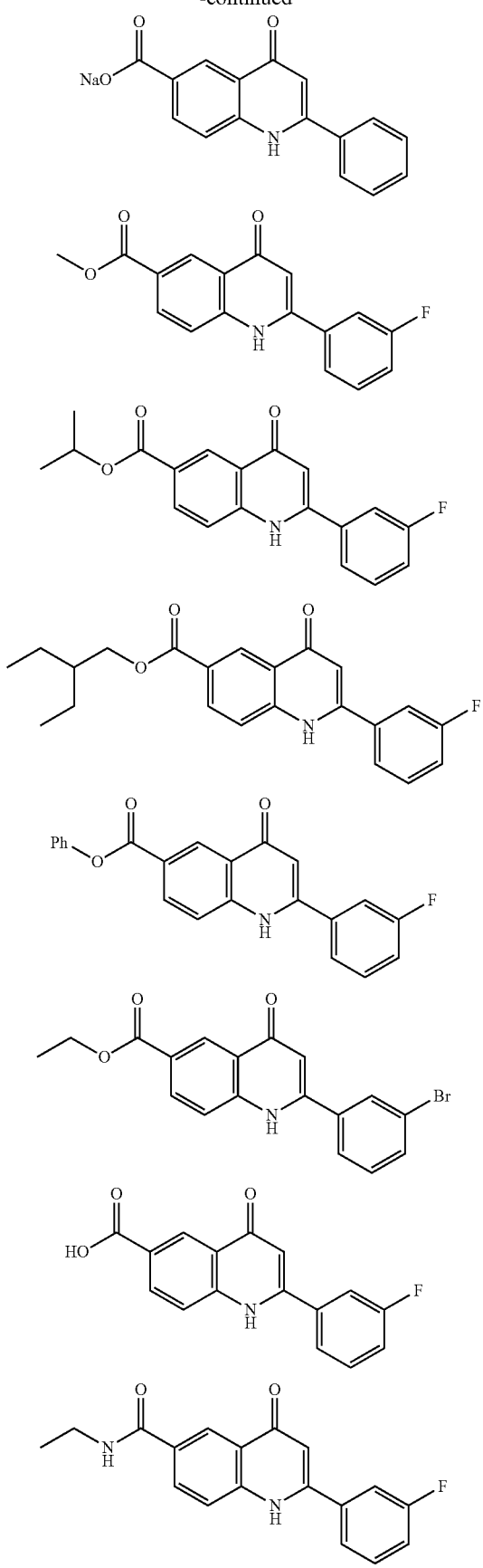
-continued
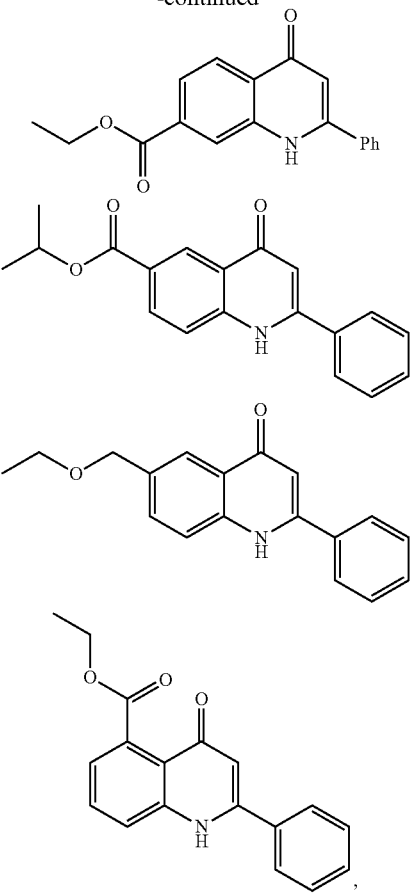
or a pharmaceutically acceptable salt, co-crystal, tautomer, stereoisomer, solvate, hydrate, polymorph, isotopically enriched derivative, or prodrug thereof.
In some embodiments, the compound of Formula (I) can be of one of the following formulae:

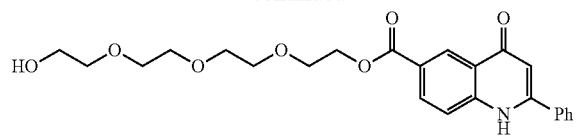
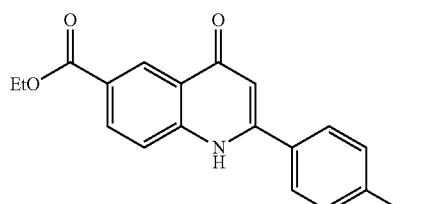
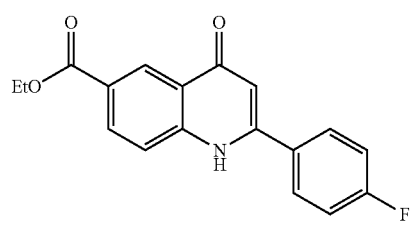
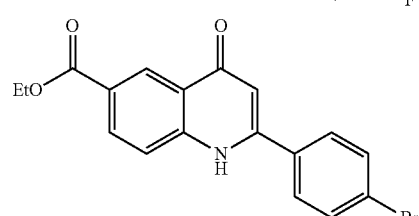
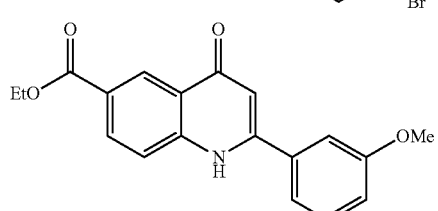
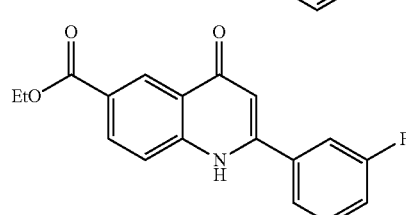
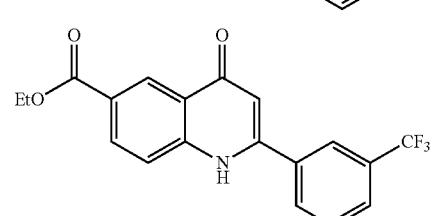
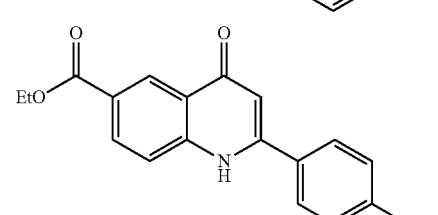
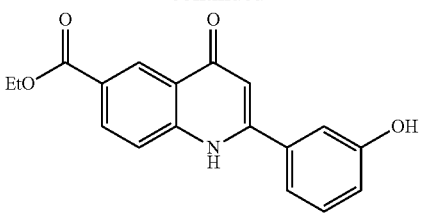
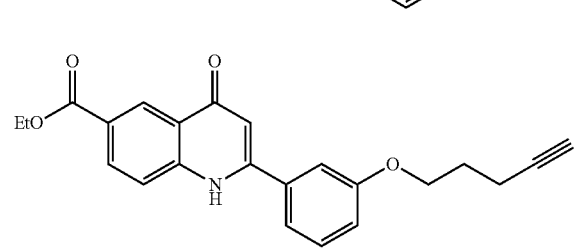
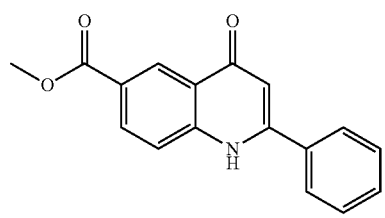
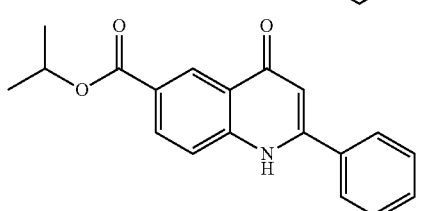
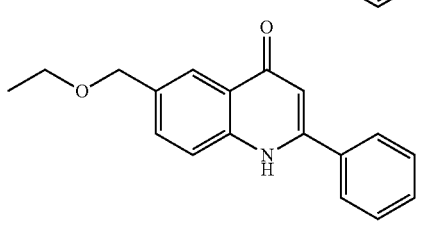
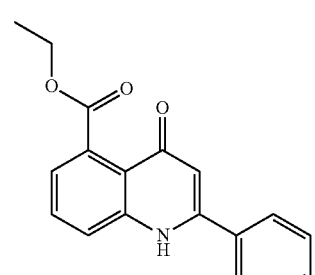
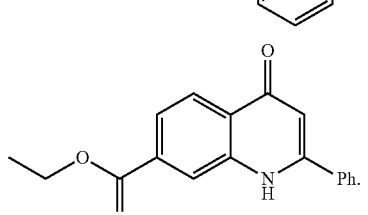
or a pharmaceutically acceptable salt thereof.
In some embodiments, the compound of Formula (I) can be of one of the following formulae:

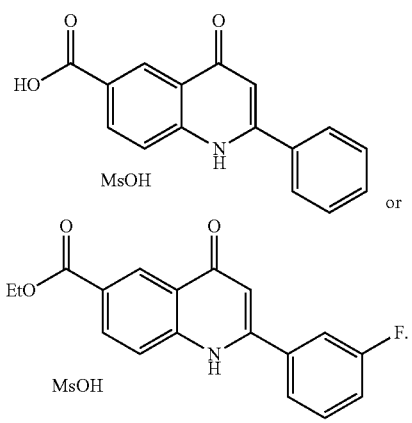

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the following synthetic routes may include, for example, solvents, reagents, catalysts, and protecting group and deprotecting group reagents. The methods described below may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of Formula (I) provided herein can be prepared from readily available starting materials using the following general methods and procedures. An exemplary schematic illustration for synthesizing the compounds described herein is provided in the Examples section below. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating a target disease such as proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids)). The pharmaceutical compositions described herein are useful in treating, delaying, and/or preventing proliferative diseases (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids)), and/or inhibiting polymerization of a cancer cell microtubule in a subject in need thereof or a cell, tissue, or biological sample, binding β-tubulin, inhibiting microtubule assembly and, consequently, inducing apoptosis in a cancer cell resistant to multiple drugs in a tissue, biological sample, or subject.

In certain embodiments, a subject being treated herein is an animal. The animal may be of either sex and may be at any stage of development. In certain embodiments, the subject is a human. In certain embodiments, the subject is a mammal (e.g., non-human mammal). In certain embodiments, the subject is a domesticated animal, such as a dog, cat, cow, pig, horse, sheep, or goat. In certain embodiments, a subject being treated herein is a companion animal such as a dog or cat. In certain embodiments, a subject being treated herein is a livestock animal such as a cow, pig, horse, sheep, or goat. In certain embodiments, a subject being treated herein is a zoo animal. In another embodiment, a subject being treated herein is a research animal such as a rodent (e.g., mouse, rat), dog, pig, or non-human primate. In certain embodiments, the animal is a genetically engineered animal. In certain embodiments, the animal is a transgenic or genetically engineered animal (e.g., transgenic mice and transgenic pigs). In certain embodiments, the subject suffers from or is suspected of having a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids)).

In certain embodiments, the cell contacted with an effective amount of a compound or pharmaceutical composition described herein is in vitro. In certain embodiments, the contacted cell is ex vivo. In certain embodiments, the cell described herein is in vivo.

In certain embodiments, the compound described herein is provided in an effective amount in the pharmaceutical composition. In certain embodiments, the effective amount is a therapeutically effective amount (e.g., amount effective for treating a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))) in a subject in need thereof). In certain embodiments, the proliferative disease is a cancer including, for example, lung cancer, breast cancer, ovarian cancer, prostate cancer, head cancer, neck cancer, head and neck cancer, or leukemia. In certain embodiments, the proliferative disease is lung cancer. In certain embodiments, the proliferative disease is breast cancer. In certain embodiments, the breast cancer is triple-negative breast cancer. In certain embodiments, the proliferative disease is neck cancer. In certain embodiments, the proliferative disease is lung cancer, breast cancer, ovarian cancer, prostate cancer, head cancer, neck cancer, head and neck cancer, or leukemia. In certain embodiments, the proliferative disease is non-small cell lung cancer.

In certain embodiments, the effective amount is a prophylactically effective amount (e.g., amount effective for preventing, delaying a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))). In certain embodiments, the effective amount is a therapeutically effective amount (e.g., amount effective for treating a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))).

In certain embodiments, the effective amount is an amount effective for inhibiting polymerization of a cancer cell microtubule in a subject in need thereof or a cell, tissue, or biological sample. In certain embodiments, the effective amount is an amount effective for binding β-tubulin in a subject in need thereof or a cell, tissue, or biological sample. In certain embodiments, the effective amount is an amount effective for inhibiting microtubule assembly in a subject in need thereof or a cell, tissue, or biological sample. In certain embodiments, the effective amount is an amount effective for inducing apoptosis in a cancer cell resistant to multiple drugs in a tissue, biological sample, or subject. In certain embodiments, the effective amount is an amount effective for inhibiting polymerization of a cancer cell microtubule in a subject in need thereof or a cell, tissue, or biological sample, binding β-tubulin, inhibiting microtubule assembly and, consequently, inducing apoptosis in a cancer cell resistant to multiple drugs in a tissue, biological sample, or subject.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. In certain embodiments, the composition of the instant disclosure is encapsulated in a carrier vehicle, which may be rigid vesicles, elastic vesicles, monolayer vesicles, multi-layer vesicles, liposomes, niosomes, proniosomes, Transfersomes®, ethosomes, L-595-PEG-8-L vesicles, nanoemulsions, nanosomes, nanoparticles, or a combination thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))). In certain embodiments, the disease is cancer including, for example, lung cancer, breast cancer, ovarian cancer, prostate cancer, head cancer, neck cancer, head and neck cancer, or leukemia. In certain embodiments, the proliferative disease is lung cancer. In certain embodiments, the proliferative disease is non-small cell lung cancer. In certain embodiments, the proliferative disease is breast cancer. In certain embodiments, the breast cancer is triple-negative breast cancer. In certain embodiments, the proliferative disease is neck cancer. In certain embodiments, the proliferative disease is lung cancer, breast cancer, ovarian cancer, prostate cancer, head cancer, neck cancer, head and neck cancer, or leukemia.

In some embodiments, the compounds described herein are useful in treating, delaying, and/or preventing the adverse effects of a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))); and/or inhibiting polymerization of a cancer cell microtubule in a subject in need thereof or a cell, tissue, or biological sample, binding β-tubulin, inhibiting microtubule assembly and, inducing apoptosis in a cancer cell resistant to multiple drugs in a tissue, biological sample, or subject.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))) in a subject in need thereof, and/or treating, delaying, and/or preventing the adverse effects of β-proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))) in a subject, cell, tissue, or biological sample. In certain embodiments, the kits and instructions provide for inhibiting polymerization of a cancer cell microtubule in a subject in need thereof or a cell, tissue, or biological sample, binding β-tubulin, inhibiting microtubule assembly and, inducing apoptosis in a cancer cell resistant to multiple drugs in a tissue, biological sample, or subject. In certain embodiments, the kits are useful for inducing apoptosis of a cancer cell (e.g., cell in vivo or in vitro). A kit described herein may include one or more additional pharmaceutical agents described herein as a separate composition.

Methods of Treatment

As shown in the Examples below, exemplary compounds described herein successfully bind to the colchicine-binding pocket of β-tubulin, induce mitotic cell cycle arrest, and induce apoptosis, to treat cancers resistant to treatment by one or more microtubule-targeting agents (e.g., cancer resistant to multiple drugs associated with P-glycoprotein (P-gp) overexpression, for example, resistant to paclitaxel and vincristine) (e.g., lung cancer, breast cancer, ovarian cancer, head and neck cancer, colon cancer, prostate cancer, leukemia)), and demonstrate inhibition of microtubule polymerization and tumor growth in cancer cells (e.g., lung cancer, breast cancer, ovarian cancer, head and neck cancer, colon cancer, prostate cancer, leukemia).

Accordingly, the present disclosure provides methods of treating a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))) in a subject in need thereof, the methods comprising administering to the subject an effective amount (e.g., therapeutically effective amount) of a compound, or pharmaceutical composition thereof, described herein. The present disclosure provides methods of inhibiting polymerization of a cancer cell microtubule in a subject in need thereof or a cell, tissue, or biological sample, binding β-tubulin, inhibiting microtubule assembly and, inducing apoptosis in a cancer cell resistant to multiple drugs in a tissue, biological sample, or subject.

Another aspect of the present disclosure relates to methods of preventing proliferative disease in a subject in need thereof, the methods comprising administering to the subject an effective amount (e.g., prophylactically effective amount) of a compound, or pharmaceutical composition thereof, described herein.

The compounds and pharmaceutical compositions described herein are useful in treating, delaying, and/or preventing a proliferative disease, such as a cancer including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))) in a subject in need thereof; and/or inhibiting polymerization of a cancer cell microtubule in a subject in need thereof or a cell, tissue, or biological sample, binding β-tubulin, inhibiting microtubule assembly and, inducing apoptosis in a cancer cell resistant to multiple drugs in a tissue, biological sample, or subject. In certain embodiments, the proliferative disease is cancer. In certain embodiments, the proliferative disease is a cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))). In certain embodiments, the cancer is resistant to multiple drugs associated with P-glycoprotein (P-gp) overexpression. In certain embodiments, the cancer is resistant to treatment by one or more microtubule-targeting agents. In certain embodiments, the one or more microtubule-targeting agents comprise a taxane or a vinca alkaloid. In certain embodiments, the cancer is resistant to taxanes and/or vinca alkaloids. In certain embodiments, the taxane is paclitaxel and/or ixabepilone. In certain embodiments, the vinca alkaloid is vincristine or vinblastine. In certain embodiments, the cancer is resistant to paclitaxel and vincristine. In certain embodiments, the proliferative disease is a cancer resistant to treatment by one or more microtubule-targeting agents (e.g., cancer resistant to multiple drugs associated with P-glycoprotein (P-gp) overexpression (e.g., cancers resistant to treatment by one or more microtubule-targeting agents (e.g., taxanes or vinca alkaloids))), and a cancer including, for example, lung cancer, breast cancer, ovarian cancer, prostate cancer, head cancer, neck cancer, head and neck cancer, or leukemia. In certain embodiments, the proliferative disease is lung cancer, breast cancer, ovarian cancer, prostate cancer, head cancer, neck cancer, head and neck cancer, or leukemia. In certain embodiments, the proliferative disease is lung cancer. In some embodiments, the proliferative disease is small cell lung cancer (SCLC). In certain embodiments, the proliferative disease is non-small cell lung cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the breast cancer is triple-negative breast cancer. In certain embodiments, the proliferative disease is neck cancer. In certain embodiments, the proliferative disease is ovarian cancer. In certain embodiments, the proliferative disease is head and neck cancer. In certain embodiments, the proliferative disease is colon cancer. In certain embodiments, the proliferative disease is prostate cancer. In certain embodiments, the proliferative disease is leukemia.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes a therapeutic for treating proliferative disease (e.g., cancers).

The compounds and compositions provided herein can be administered by any route, including enteral (e.g., oral), parenteral, intravenous, intramuscular, intra-arterial, intracranial, intramedullary, intrathecal, subcutaneous, intraventricular, transdermal, intradermal, interdermal, rectal, intravaginal, intraperitoneal, topical (as by powders, ointments, creams, and/or drops), by any means that facilitate in vivo or ex vivo transport of the compound or composition as described herein in, into, or through tissue/skin of a subject (such as iontophoresis), mucosal, nasal, buccal, sublingual; by intratracheal instillation, bronchial instillation, and/or inhalation; and/or as an oral spray, nasal spray, and/or aerosol. In some embodiments, the pharmaceutical composition is administered orally or parentally. In some embodiments, the pharmaceutical composition is administered orally. In some embodiments, the pharmaceutical composition is administered parentally. Specifically contemplated routes are oral administration, intravenous administration (e.g., systemic intravenous injection), transfusion, perfusion, regional administration via blood and/or lymph supply, and/or direct administration to an affected site, such as intra-tumoral. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower, higher, or the same as that administered to an adult.

A compound or composition, as described herein, can be administered in combination with one or more additional pharmaceutical agents (e.g., therapeutically and/or prophylactically active agents) useful in treating proliferative disease (e.g., cancer) in a subject in need thereof). The compounds or compositions can be administered in combination with additional pharmaceutical agents that improve their activity (e.g., activity (e.g., potency and/or efficacy) in treating proliferative disease (e.g., cancer) in a subject in need thereof, and/or in treating, delaying, and/or preventing the adverse effects of proliferative disease (e.g., cancer in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, for different disorders, and/or it may achieve different effects. In certain embodiments, a pharmaceutical composition described herein including a compound described herein is administered to a patient in need thereof, to advantageously treat one or more diseases. In certain embodiments, said one or more diseases is a proliferative disease (e.g., cancer, including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression))), or a combination thereof. In a preferred embodiment, said one or more diseases is lung cancer, breast cancer, ovarian cancer, prostate cancer, head cancer, neck cancer, head and neck cancer, or leukemia, all resistant to treatment by one or more microtubule-targeting agents (e.g., cancer resistant to multiple drugs associated with P-glycoprotein (P-gp) overexpression), or a combination thereof.

The compound or composition may be administered concurrently with, prior to, or subsequent to one or more additional pharmaceutical agents, which may be useful as, e.g., combination therapies. In certain embodiments, the compound or composition described herein can be administered to a patient in need thereof, wherein the cancer (e.g., lung cancer, breast cancer, ovarian cancer, prostate cancer, colon cancer, head cancer, neck cancer, head and neck cancer, or leukemia) of the patient is resistant to at least one pharmaceutical agent (e.g., a cancer resistant to treatment by one or more microtubule-targeting agents (e.g., cancer resistant to multiple drugs associated with P-glycoprotein (P-gp) overexpression)). In certain embodiments, the disease is cancer (e.g., lung cancer, breast cancer, ovarian cancer, prostate cancer, colon cancer, head cancer, neck cancer, head and neck cancer, or leukemia) and said cancer (e.g., lung cancer, breast cancer, ovarian cancer, prostate cancer, colon cancer, head cancer, neck cancer, head and neck cancer, or leukemia) is resistant to one or more microtubule-targeting agents (e.g., cancer resistant to multiple drugs associated with P-glycoprotein (P-gp) overexpression)) including but not limited to taxanes or vinca alkaloids. In certain embodiments, the cancer resistant to multiple drugs is associated with P-glycoprotein (P-gp) overexpression. In certain embodiments, the cancer resistant to multiple drugs is associated with β-tubulin mutations.

Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease (e.g., cancer). In certain embodiments, the additional pharmaceutical agent is a pharmaceutical agent useful in preventing a proliferative disease (e.g., cancer) in erythrocytes. In certain embodiments, the additional pharmaceutical agent is a pharmaceutical agent useful in inhibiting polymerization of a cancer cell microtubule in a subject in need thereof or a cell, tissue, or biological sample, binding □-tubulin, inhibiting microtubule assembly and, inducing apoptosis in a cancer cell resistant to multiple drugs in a tissue, biological sample, or subject. In certain embodiments, the additional pharmaceutical agent is a pharmaceutical agent approved by a regulatory agency (e.g., the US FDA) for treating and/or preventing a proliferative disease (e.g., cancer). In certain embodiments, the additional pharmaceutical agent is a pharmaceutical agent approved by a regulatory agency (e.g., the US FDA) for treating and/or preventing lung cancer (e.g., non-small cell lung cancer). In certain embodiments, the additional pharmaceutical agent is a pharmaceutical agent approved by a regulatory agency (e.g., the US FDA) for treating and/or preventing breast cancer (e.g., triple-negative breast cancer). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent), anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with anti-cancer therapy. In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PRO VENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof.

The present disclosure also provides a compound of Formula (I), or a pharmaceutically acceptable salt, co-crystal, tautomer, stereoisomer, solvate, hydrate, polymorph, isotopically enriched derivative, or prodrug, or composition thereof, for use in the treatment of proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression) (e.g., taxanes or vinca alkaloids)), in a subject in need thereof.

The present disclosure also provides uses of a compound of Formula (I), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of proliferative diseases, such as cancers including, for example, lung cancer, breast cancer, ovarian cancer, prostate cancer, head cancer, neck cancer, head and neck cancer, or leukemia (e.g., cancer resistant to treatment by one or more microtubule-targeting agents (e.g., cancer resistant to multiple drugs associated with P-glycoprotein (P-gp) overexpression) (e.g., taxanes or vinca alkaloids)), in a subject in need thereof.

In certain embodiments, provided are methods of inhibiting polymerization of a cancer cell microtubule in a subject in need thereof, the method comprising administering to the subject a therapeutically effective amount of a compound of Formula (I), or a pharmaceutically acceptable salt, co-crystal, tautomer, stereoisomer, solvate, hydrate, polymorph, isotopically enriched derivative, or prodrug thereof, or a pharmaceutical composition described herein.

In some embodiments, provided are methods of inducing apoptosis in a cancer cell resistant to multiple drugs in a tissue, biological sample, or subject, the method comprising administering to the subject or contacting the cell, tissue, or biological sample a therapeutically effective amount of a compound of Formula (I), or a pharmaceutically acceptable salt, co-crystal, tautomer, stereoisomer, solvate, hydrate, polymorph, isotopically enriched derivative, or prodrug thereof, or a pharmaceutical composition described herein. In some embodiments, the methods further comprise contacting the cell, tissue, or biological sample with a therapeutically effective amount of an additional pharmaceutical agent in combination with a compound described herein.

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Analysis of Exemplary Compounds for Biological Activity

In this study, a two-step high-throughput screening of 2 million compounds was performed to search for novel molecules with therapeutic activity against lung cancer. An exemplary compound, Ethyl 4-oxo-2-phenyl-1,4-dihydroquinoline-6-carboxylate (AS1712) was found to have anti-cancer activity in vitro and in vivo and a superior therapeutic specificity for cancer instead of normal cells. It was found that AS1712 inhibited the growth of various types of cancer cells, including those of the lung, prostate, ovary, breast, colon, and head and neck and leukemia. By targeting the colchicine-binding site of β-tubulin, AS1712 induced mitotic cell cycle arrest and apoptosis. Notably, the distinct tubulin-binding site of AS1712 circumvented resistance caused by β-tubulin alterations and P-gp overexpression.

[AS1712 Inhibited Lung Cancer Cell Proliferation In Vitro and In Vivo and Had Broad Anti-Cancer Activity]

With the use of two-step high-throughput screening procedure, exemplary compound ethyl 4-oxo-2-phenyl-1,4-dihydroquinoline carboxylate (AS1712) was shown to drastically decrease the proliferation of many different lung cancer cell lines, including the EGFR TKI-resistant cell lines H1975 and PC9/IR; the clinical isolates CL25, CL83, CL97, CL100, CL141, and CL152; and the ATCC cell line PC-9. The cytotoxic effects of exemplary compound AS1712 on different non-small cell lung cancer cell lines were first evaluated using an MTS assay and it was found that AS1712 induced cell death in different EGFR-status cell lines, including A549 (wild-type EGFR), CL1-0 (wild-type EGFR), PC9 (EGFR exon 19 deletion), and H1975 (T790M and L858R mutations in EGFR). The $IC_{50}$ values for the affected cell lines ranged from 16 to 33 nM (FIG. 1A), which indicated that the cytotoxic effect of AS1712 was not related to the EGFR status of lung cancer cells. Furthermore, AS1712 was relatively non-toxic against normal bronchial epithelial (NBE) and human fibroblast (HFB) cells ($IC_{50}$>10 µM; FIG. 1A). The colony-forming abilities of CL1-0 and H1975 cells were suppressed in a dose-dependent manner by exemplary compound AS1712 (FIGS. 1B-1E). The aforementioned data suggested that AS1712 inhibited non-small cell lung cancer proliferation in vitro.

Figure 2A:
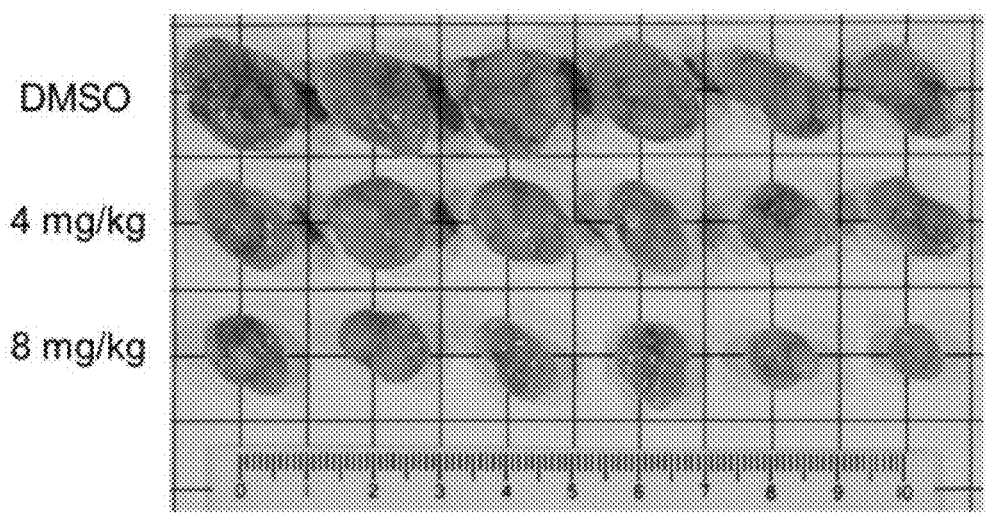
FIGS. 2A to 2D show inhibition of H1975 xenograft tumor growth by treatment with exemplary compound AS1712 (4 or 8 mg/kg) (data are the mean±SEM, *p<0.05): images of tumors (FIG. 2A); tumor weights (FIG. 2B); representative hematoxylin and eosin (H&E)-stained sections after sacrifice (FIG. 2C); and body masses (FIG. 2D).
Figure 2B:
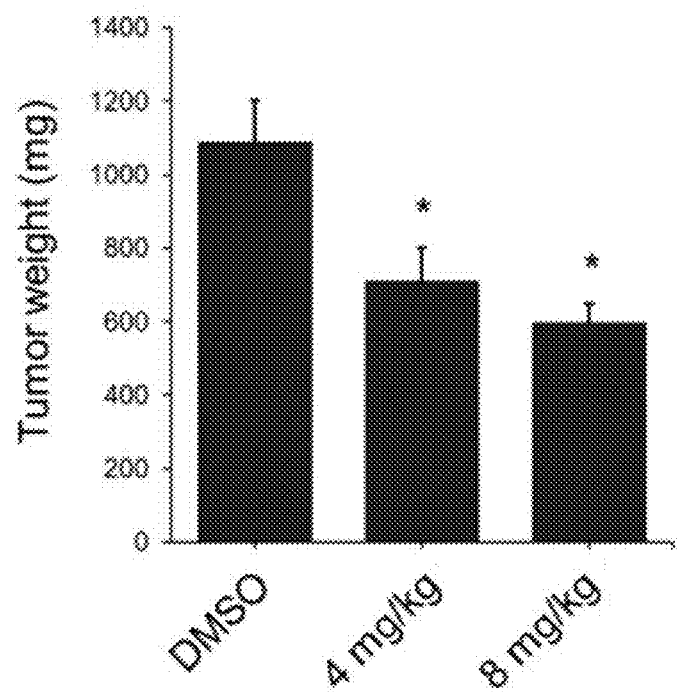
Figure 2C:
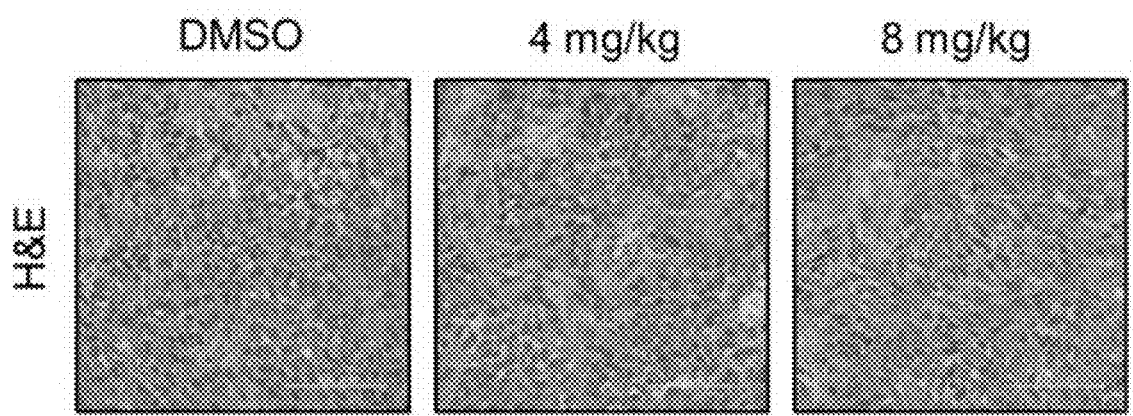
Figure 2D:
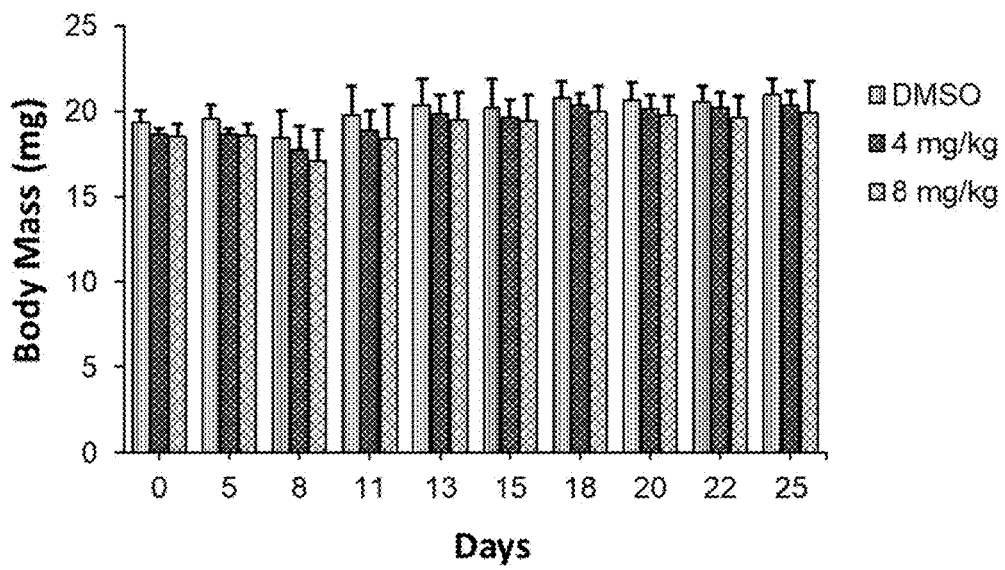

To evaluate the in vivo anti-tumor efficacy of exemplary compound AS1712, athymic BALB/c nude mice each bearing an established subcutaneous H1975 tumor were intraperitoneally injected with DMSO (control) or with 4 or 8 mg/kg AS1712, three times a week for 25 days (n=6 per group). The tumor volume and body mass of each mouse were monitored throughout the treatment period. Treatment with AS1712 markedly reduced H1975 xenograft tumor growth compared with that found for the control group (average tumor size, 1749±234.5 mm$^3$ for DMSO treatment; 871.3±106 mm$^3$ for the 4 mg/kg and 587.2±67 mm$^3$ for 8 mg/kg treatments; all measured on day 25 and both p<0.01; FIGS. 1F, 2A-2D and Table 1). The body masses and serum biochemical markers for liver and kidney functions, including ALT, AST, BUN, and Cre, were non-toxic affected on day 25 of the experiment (FIG. 2D and Table 1). Thus AS1712 inhibited tumor growth with low toxicity in vivo.

TABLE 1

Serum biochemical markers of the liver and kidney functions
ALT, AST, BUN, and Cre (data are the mean ± SEM)

|         | ALT (IU/L)  | AST (IU/L)   | BUN (mg/dl) | Cre (mg/dl)    |
|---------|-------------|--------------|-------------|----------------|
| DMSO    | 36.6 ± 5.9  | 122 ± 14.5   | 18.5 ± 1.6  | 0.14 ± 0.02    |
| 4 mg/kg | 40.8 ± 11   | 138.7 ± 58.6 | 23.2 ± 2.5  | 0.26 ± 0.05    |
| 8 mg/kg | 54.2 ± 16   | 170.8 ± 44.5 | 20.9 ± 1.5  | 0.17 ± 0.02    |

The cytotoxicity of exemplary compound AS1712 against various types of cancer cells was also assessed and it was found that AS1712 decreased the viability of many different types of malignant cells, including those derived from lung (A549, CL1-0, PC9, and H1975), breast (BT-549, Hs578t, MDA-MB-231, 37T, and 82T), ovarian (SKOV-3, IGR-OV1, and Ovcar-3), head and neck (SAS, OECM1, and KB), colon (HCT116, HT-29, Colon205, and SW620), and prostate (Du-145 and PC-3) cancers and from leukemia (Molt4 and CCRF-CEM). For the 23 cancer cell lines tested, their $IC_{50}$ values ranged from 16 to 84 nM (Table 2), suggesting that exemplary compound AS1712 or a derivative of exemplary compound AS1712 might be used for the treatment of various types of cancers.

TABLE 2

Inhibitory Activities of AS1712 against the Proliferation
of different Cancer Cell lines or Normal cell lines

| Cell line          | $IC_{50}$ (nM) |
|--------------------|----------------|
| Lung cancer    |                |
| A549               | 20 ± 0.98      |
| CL1-0              | 16 ± 2.48      |
| PC9                | 17 ± 2.09      |
| H1975              | 33 ± 4.86      |
| Breast cancer  |                |
| BT-549             | 33 ± 1.51      |
| Hs578t             | 41 ± 2.87      |
| MDA-MB-231         | 55 ± 6.83      |
| 37T                | 34 ± 2.99      |
| 82T                | 35 ± 0.67      |
| Ovarian cancer |                |
| SKOV-3             | 50 ± 0.32      |
| IGR-OV1            | 84 ± 2.07      |
| Ovcar-3            | 28 ± 1.08      |
| Head and Neck cancer |          |
| SAS                | 78 ± 10.4      |
| OECM1              | 52 ± 1.94      |
| KB                 | 37 ± 0.27      |
| Colon cancer   |                |
| HCT116             | 50 ± 0.81      |
| HT-29              | 48 ± 0.62      |
| Colon205           | 57 ± 5.17      |
| SW620              | 35 ± 1.18      |
| Prostate cancer|                |
| Du-145             | 47 ± 1.28      |
| PC-3               | 45 ± 1.77      |
| Leukemia       |                |
| Molt4              | 38 ± 1.03      |
| CCRF-CEM           | 45 ± 0.45      |
| Normal cell line |              |
| NEB                | >10 μM         |
| HFB                | >10 μM         |

[AS1712 Induced Apoptosis and Cell Cycle Arrest]

Figure 3:
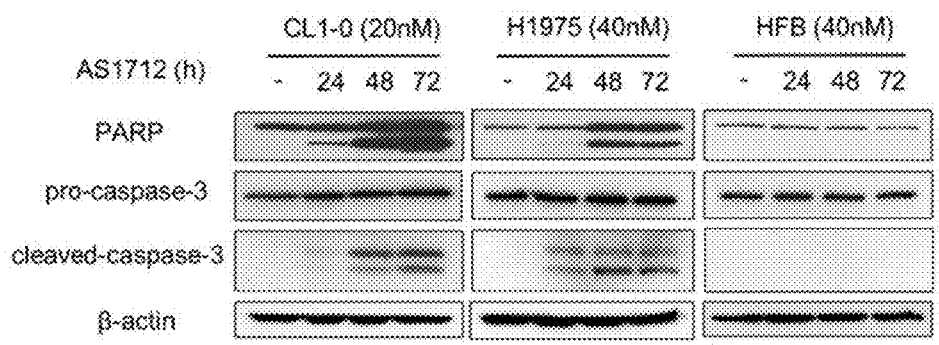
FIG. 3 shows that CL1-0, H1975, and HFB cells were treated with the indicated concentrations of exemplary compound AS1712 for 24-72 h prior to assessing the extent of pro-apoptotic protein expression.
Figure 4A:
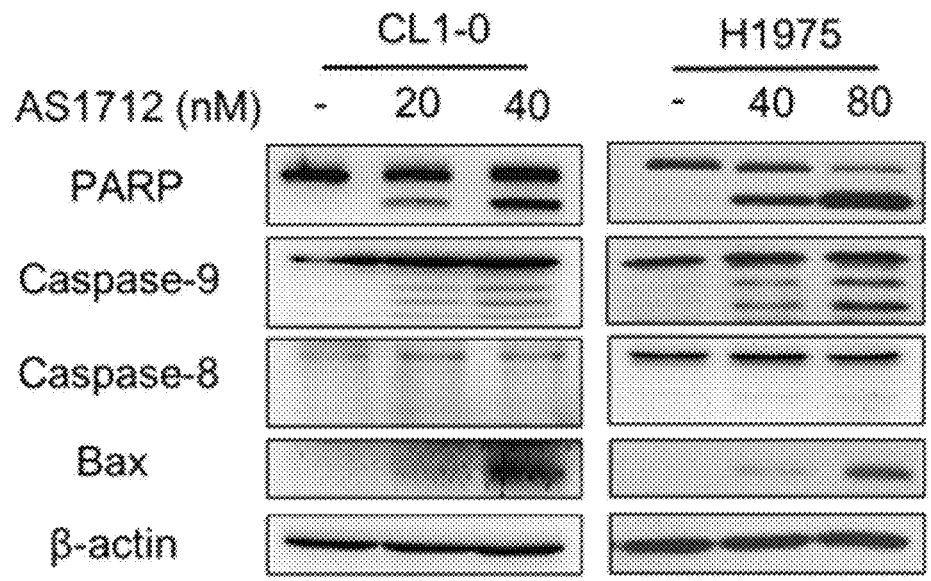
FIGS. 4A to 4F show that exemplary compound AS1712 induced apoptosis and cell cycle arrest in CL1-0 and H1975 lung cancer cell lines (cells were treated with the indicated concentrations of AS1712 for 24 h)
Figure 4B:
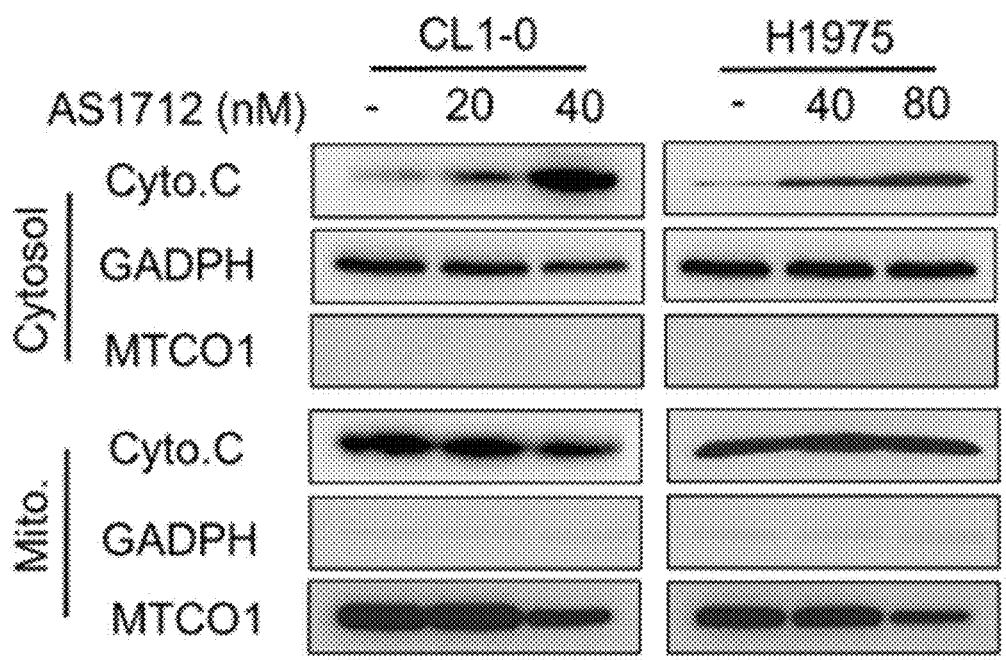
Figure 5A:
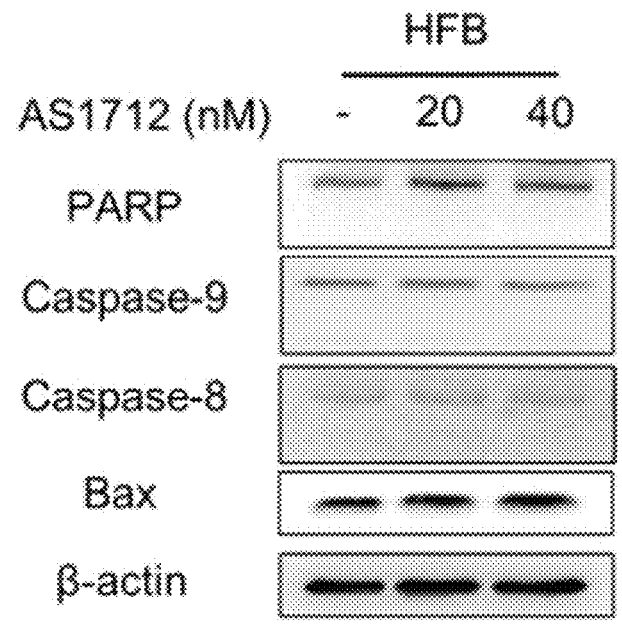
FIGS. 5A to 5C show that AS1712-treated-HFB cells were examined for apoptotic pathway markers (FIG. 5A), cytochrome c from mitochondria (FIG. 5B), and cell cycle regulation (FIG. 5C).
Figure 5B:
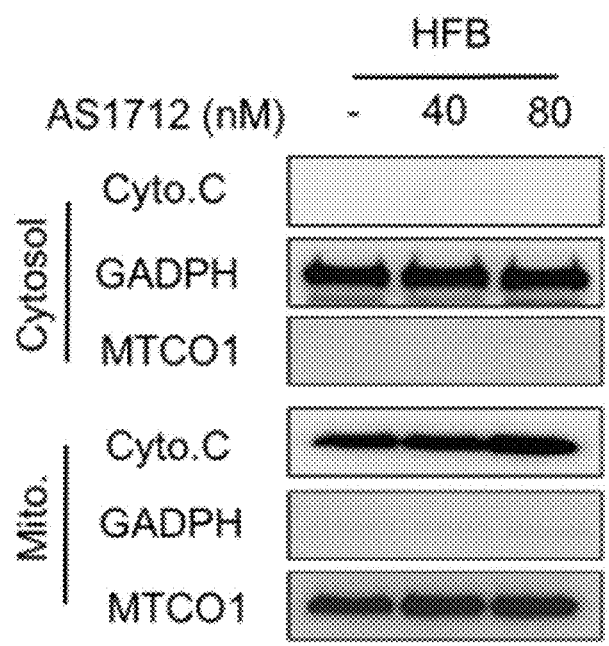

To evaluate whether the cytotoxic effect of exemplary compound AS1712 correlated with apoptotic cell death, CL1-0, H1975, and HFB cells were treated with AS1712 for 24 to 72 h and then monitored for the activation of major pro-apoptotic proteins. It was found that AS1712 induced cleavage of poly(ADP-ribose) polymerase (PARP) and caspase-3 in CL1-0 and H1975 cells in a time-dependent manner; PARP and caspase-3 in the normal HFB cells were not affected by AS1712 (FIG. 3). Apoptotic pathway proteins that might have been activated by AS1712 were then investigated and it was found that AS1712 induced two intrinsic apoptosis pathway markers, cleavage of caspase-9 and expression of Bax, in a dose-dependent manner (FIG. 4A). Conversely, the extrinsic apoptosis pathway marker, caspase-8, was not activated by AS1712 treatment (FIG. 4A). It was also found that a 24-h treatment with AS1712 increased the cytosolic level of cytochrome c (FIG. 4B), whereas the same dose of AS1712 did not induce apoptosis in HFB cells or cytochrome c release (FIGS. 5A and 5B). AS1712 therefore induced activation of the intrinsic apoptosis pathway only in cancer cells.

Figure 4C:
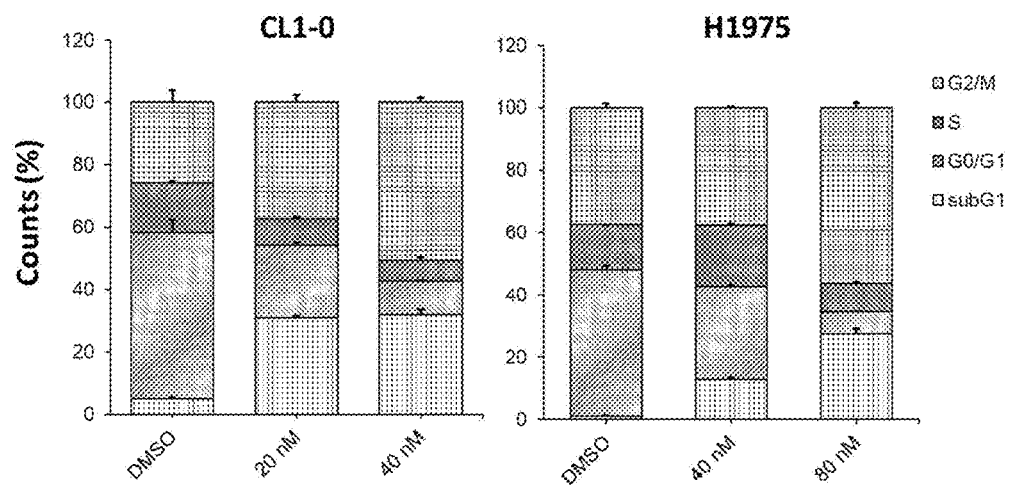
Figure 4D:
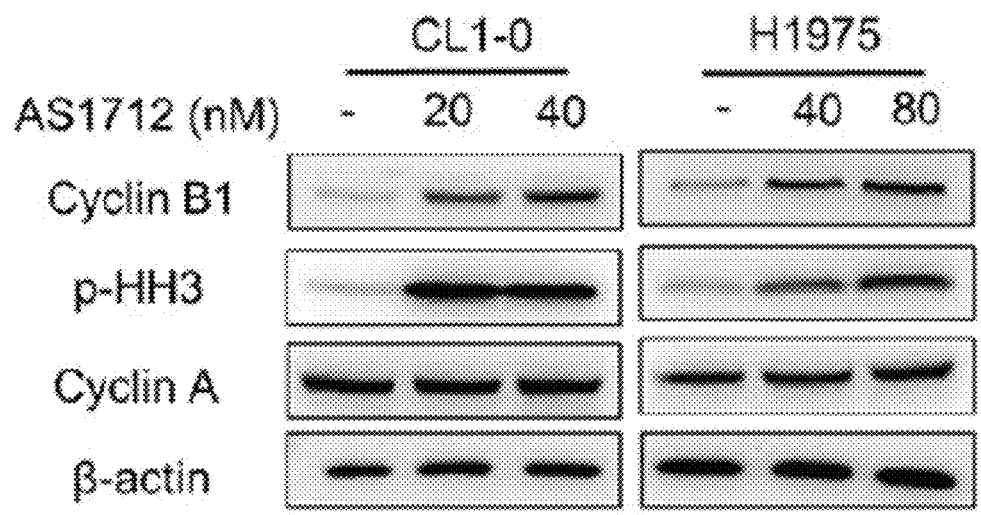
Figure 4E:
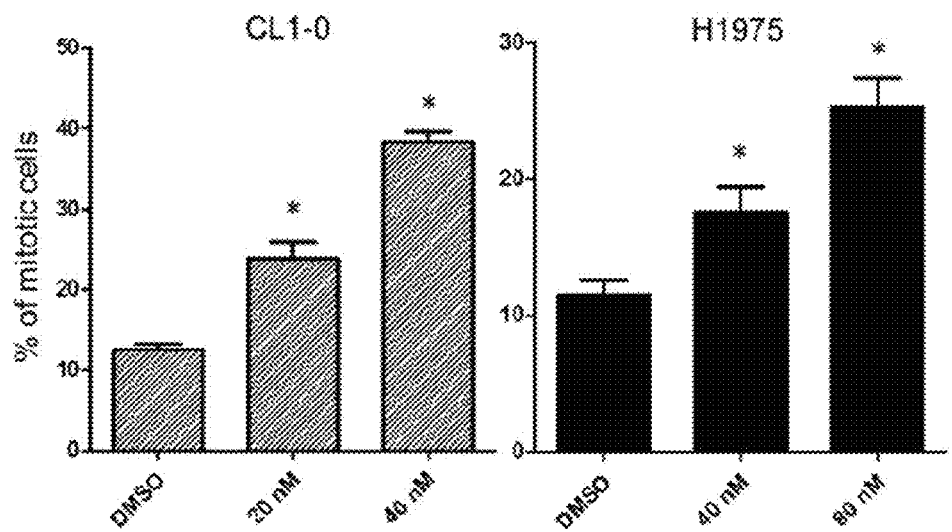
Figure 4F:
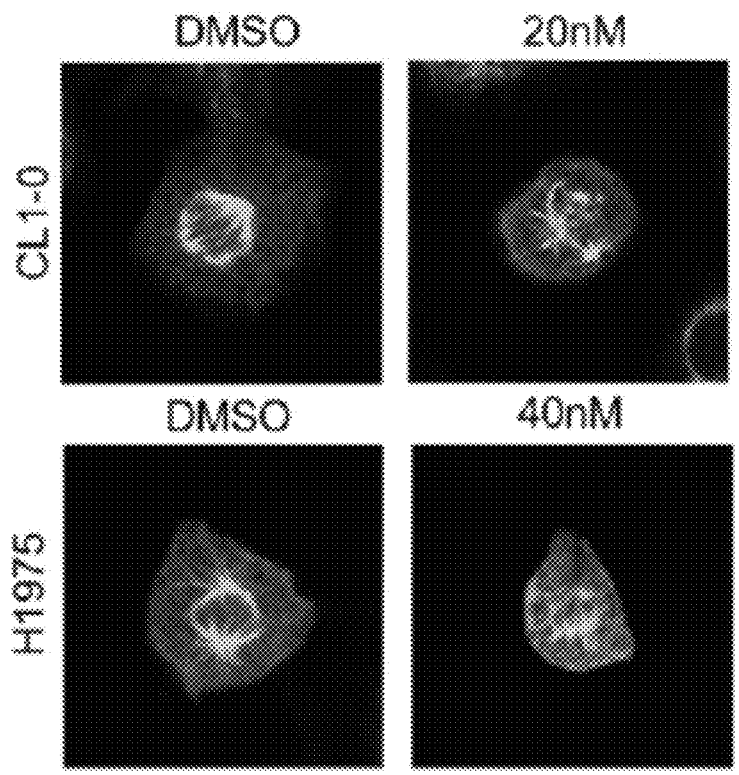
Figure 5C:
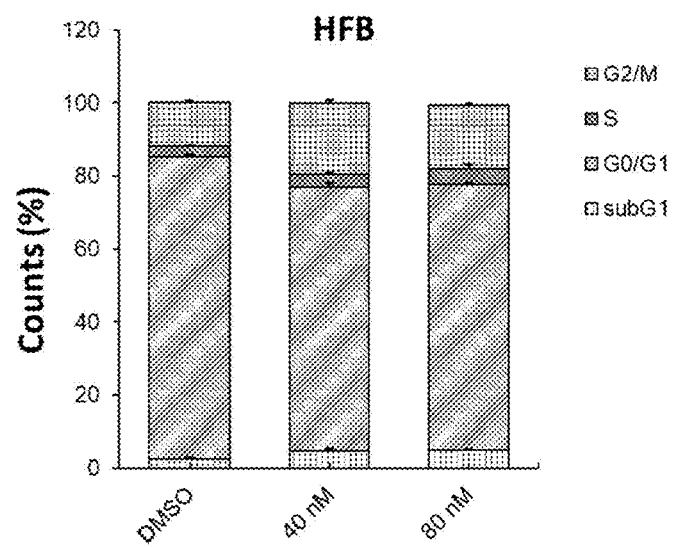

Next, it was explored whether the apoptotic effect of AS1712 was caused by aberrant cell cycle progression. The distribution of CL1-0, H1975, and HFB cells among phases of the cell cycle was examined by flow cytometry. AS1712 treatment increased the sub-G1 (apoptotic cell population) and the G2/M-phase population of CL1-0 and H1975 cells in a dose-dependent manner (FIG. 4C) but not of HFB cells (FIG. 5C). To clarify whether AS1712 induced G2 or mitotic cell cycle arrest, the cell cycle was characterized at its checkpoints for CL1-0 and H1975 cells and it was found that AS1712 increased the mitotic-phase markers cyclin B1 and phospho-histone H3 (p-HH3) but not the G2-phase marker cyclin A (FIG. 4D). High-content imaging was also used to measure the mitosis index (the population of mitotic cells) by staining for the specific mitotic phase marker p-HH3 and found that AS1712 treatment caused CL1-0 and H1975 cells to accumulate in the mitotic phase in a dose-dependent manner (FIG. 4E). Furthermore, the mitotic-spindle organization was directly evaluated using α-tubulin immunofluorescence staining and observed that arrangement of the mitotic spindles was disrupted by AS1712 treatment (FIG. 4F). The aforementioned data showed that AS1712 induced mitotic cell cycle arrest.

[AS1712 Directly Inhibited Microtubule Polymerization]

Figure 6A:
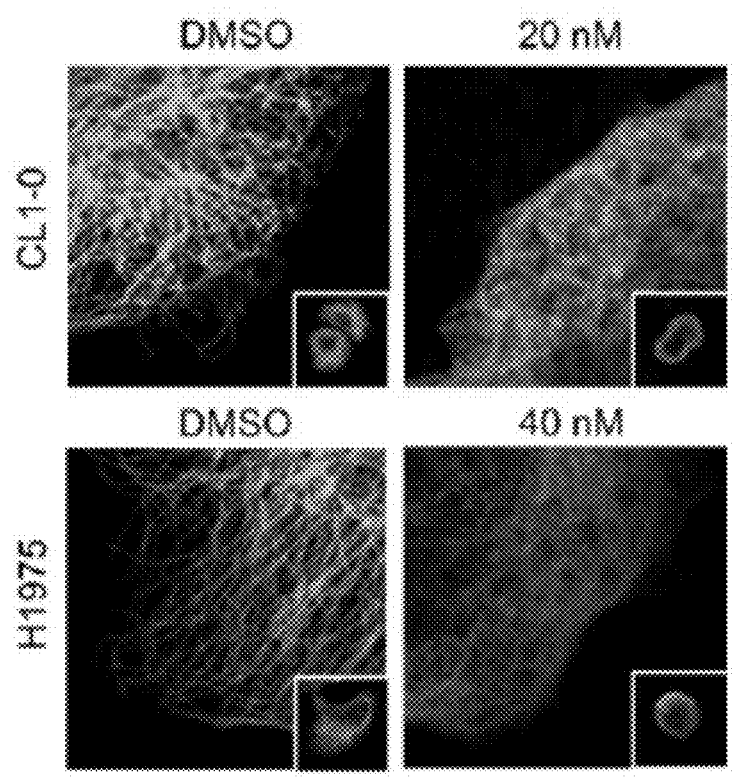
FIGS. 6A to 6E show that exemplary compound AS1712 inhibited microtubule polymerization.
Figure 6B:
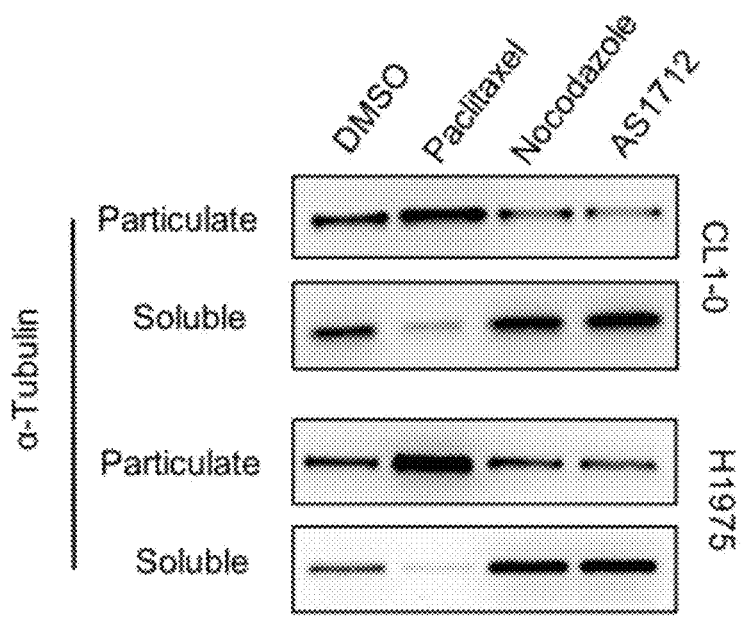
Figure 6C:
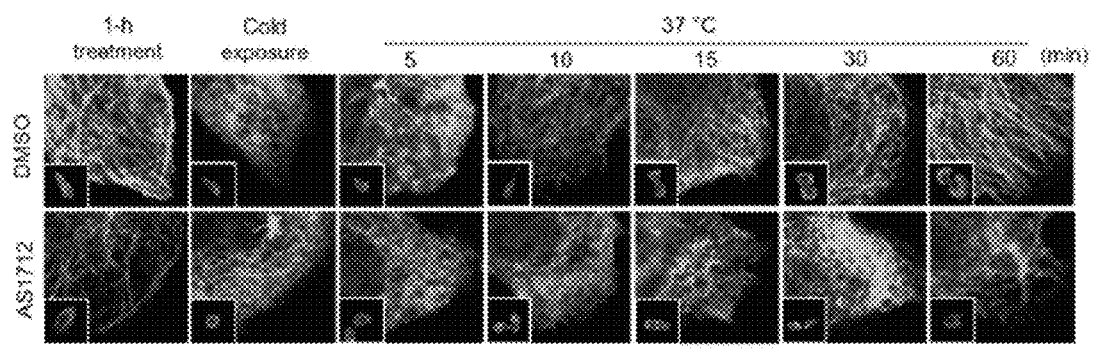
Figure 6D:
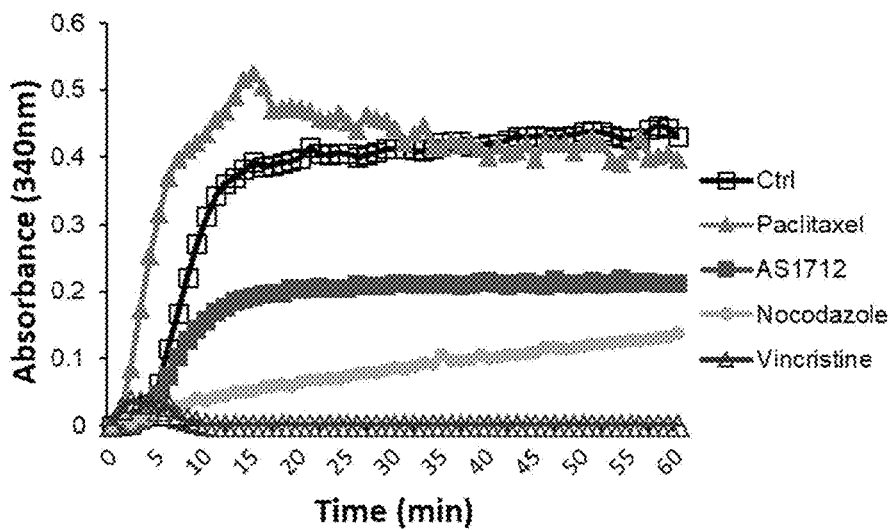
Figure 6E:
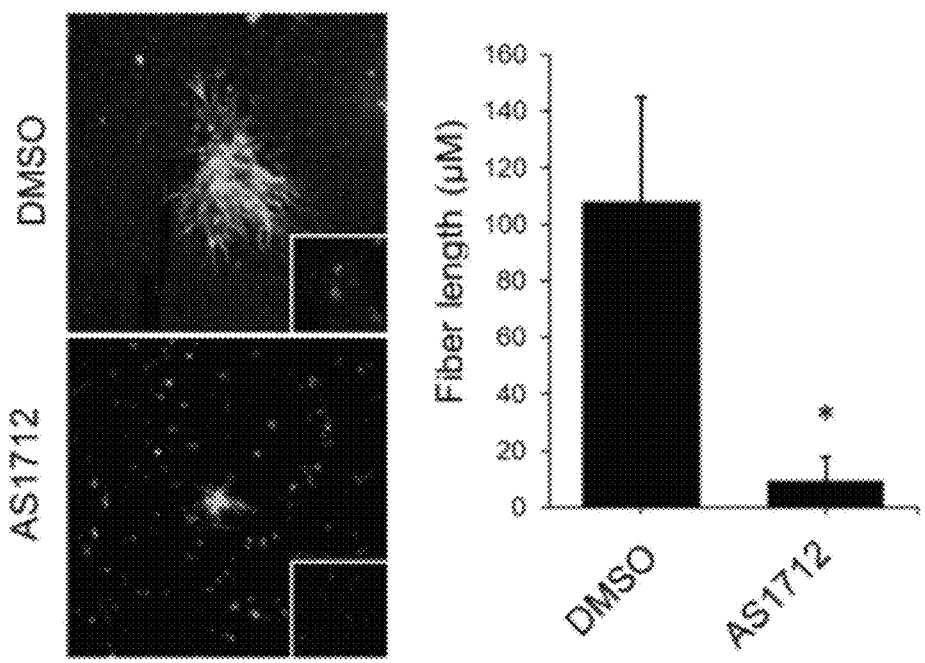
Figure 7:
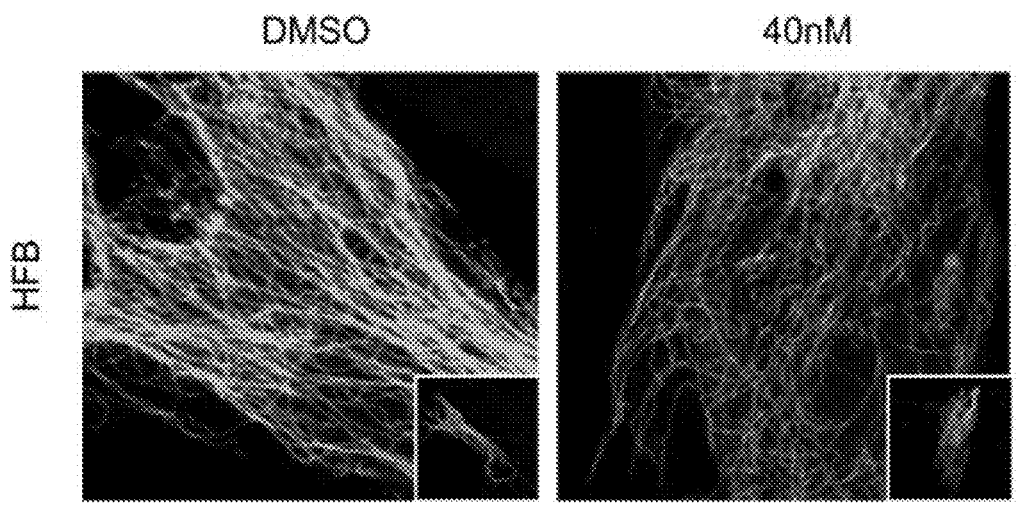
FIG. 7 shows the microtubule networks in HFB cells after 6 h of treatment with 40 nM AS1712.

The observation that AS1712 treatment disrupted mitotic-spindle organization led to the possibility that the treatment might interfere with dynamic microtubule association and/or dissociation. Therefore, an immunofluorescence assay was performed to examine the status of microtubule networks in AS1712-treated CL1-0, H1975, and HFB cells. AS1712 treatment of CL1-0 and H1975 cells resulted in depolymerization of their microtubules (FIG. 6A), whereas such treatment had only a minor effect on microtubules in HFB cells (FIG. 7). An in-cell microtubule assembly assay was performed, after first separating assembled and disassembled microtubules into particulate and soluble fractions, respectively, by centrifugation. Notably, AS1712 substantially increased the amount of α-tubulin in the soluble fraction, a finding similar to that found for nocodazole but not paclitaxel treatment (FIG. 6B). It was further confirmed that AS1712 induced depolymerization of microtubules using an immunofluorescence-based microtubule polymerization assay. H1975 cells were first treated with 40 nM AS1712 for 1 h, were then exposed to the cold for 30 min, and then were shifted to 37° C. for various times. When treated with AS1712, the microtubules failed to polymerize at 37° C. (FIG. 6C). Next, an in vitro tubulin polymerization assay was used with purified tubulin to examine whether AS1712 directly interfered with microtubule assembly in a cell-free system. As expected, the reference agents nocodazole and vincristine were found to inhibit tubulin polymerization, whereas paclitaxel enhanced polymerization. AS1712 was also found to directly inhibit tubulin polymerization (FIG. 6D). An in vitro microtubule nucleation assay was carried out to test whether AS1712 directly inhibited the assembly of new microtubules at purified centrosomes. Purified centrosomes and tubulins were incubated with AS1712 or DMSO. AS1712 substantially inhibited the formation of microtubule asters from the centrosome (FIG. 6E, left panel). A quantitative analysis of microtubule fiber length also showed a dramatic difference between AS1712 and DMSO treatments (FIG. 6E, right panel). The aforementioned data showed that AS1712 directly inhibited microtubule polymerization.

Example 2. Synthesis of Exemplary Compounds

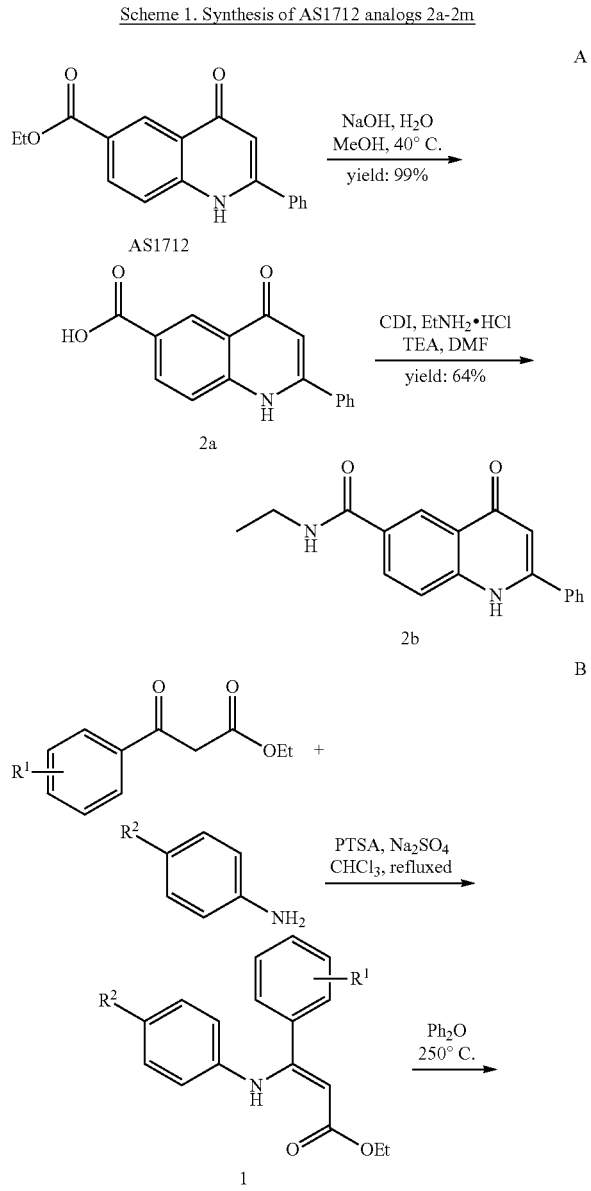

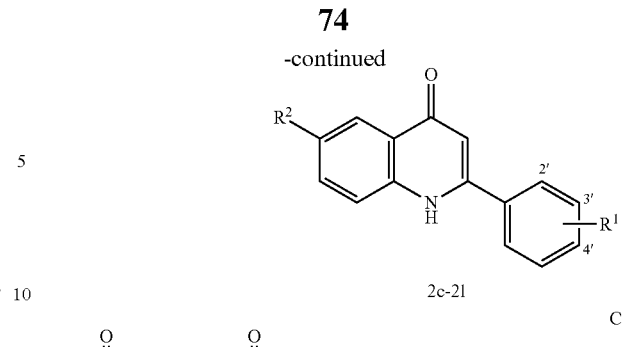

2c $R^1$ = 4'-OMe   $R^2$ = COOEt   Yield: 73%
2d $R^1$ = 4'-F     $R^2$ = COOEt   Yield: 83%
2e $R^1$ = 4'-Br    $R^2$ = COOEt   Yield: 87%
2f $R^1$ = 4'-OH    $R^2$ = COOEt   Yield: 48%
2g $R^1$ = 3'-OMe   $R^2$ = COOEt   Yield: 85%
2h $R^1$ = 3'-F     $R^2$ = COOEt   Yield: 88%
2i $R^1$ = 3'-CF$_3$ $R^2$ = COOEt   Yield: 82%
2j $R^1$ = 3'-OH    $R^2$ = COOEt   Yield: 27%
2k $R^1$ = H        $R^2$ = COOMe   Yield: 82%
2l $R^1$ = H        $R^2$ = COO$^i$Pr Yield: 73%

[Cell-Based Structure-Activity Relationship (SAR) Study of AS1712 Led to the Identification of the More Potent Anti-Cancer Compound RJ-LC-15-8]

To find more potent AS1712-based compounds with increased anti-cancer activity, an SAR study was carried out using H1975 cells and exemplary AS1712 analogs, which possessed the 4(1H)-quinolone scaffold. As shown in above Scheme 1A and below Table 3, AS1712 was first hydrolyzed to the acid 2a, which had an $IC_{50}$>5 µM. Next 2a was transformed into the ethyl amide 2b, which had an $IC_{50}$=3.7 µM. Both analogs had substantially less activity against H1975 cells then did AS1712. The focus was then moved to structural optimization of the phenyl group at the C-2 position of the 4(1H)-quinolone scaffold. The effects of substituents at the meta or para positions of the aryl ring were explored using 2c-2j, which were readily synthesized by reactions involving ethyl 3-aryl-3-oxypropanoates and ethyl 4-aminobenzoates, and cyclization of the resulting β-enamino esters 1 in hot diphenyl ether (Scheme 1B). Addition of an electron-donating group (2c, $IC_{50}$=2.2 µM), -withdrawing groups (2d, $IC_{50}$=2.1 µM and 2e, $IC_{50}$=4.5 µM), or a hydroxyl group (2f, $IC_{50}$=475 nM) at the para position of the phenyl group resulted in substantial decreases in inhibitory activity against H1975 cells. Interestingly, while exploring the effects of meta substituents, it was found that 2h possessing a meta-fluorophenyl moiety had increased inhibitory activity ($IC_{50}$=24 nM) against H1975 cells, whereas 2i and 2j, which bore a trifluoromethyl and a hydroxyl group respectively at the meta position of the phenyl ring showed substantially decreased potencies ($IC_{50}$=780 nM and 1.95 µM, respectively) compared with that of AS1712. The introduction of a meta-methoxy group (2g) on the tail aryl ring slightly reduced activity ($IC_{50}$=44 nM). The effects of substituents at the 6-position of the 4(1H)-quinolone scaffold were also explored by replacing the ethyl group with less or more sterically bulky groups (2k, $IC_{50}=207$ nM and 2l, $IC_{50}=48$ nM, respectively) or by removal of the oxo group (2m, Scheme 1C, $IC_{50}=810$ nM). The results showed that the original ethyl carbonate is the optimal substituent at the C-6 position. Overall, the data gained from the SAR study suggested that 2h (denoted RJ-LC-15-8) possessed a greater anti-cellular proliferation potency ($IC_{50}=24$ nM) against H1975 cells than did AS1712.

TABLE 3

Cell-based SAR study of AS1712 for the inhibition of H1975 cells

| Compound | $R^1$ | $R^2$ | $IC_{50}$ |
|---|---|---|---|
| AS1712 | H | COOEt | 35 nM |
| 2a | H | COOH | >5 μM |
| 2b | H | CONHEt | 3.7 μM |
| 2c | 4'-OMe | COOEt | 2.2 μM |
| 2d | 4'-F | COOEt | 2.1 μM |
| 2e | 4'-Br | COOEt | 4.5 μM |
| 2f | 4'-OH | COOEt | 475 nM |
| 2g | 3'-OMe | COOEt | 44 nM |
| 2h(RJ-LC-15-8) | 3'-F | COOEt | 24 nM |
| 2i | 3'-$CF_3$ | COOEt | 780 nM |
| 2j | 3'-OH | COOEt | 1.95 μM |
| 2k | H | COOMe | 207 nM |
| 2l | H | $COO^iPr$ | 48 nM |
| 2m | H | $CH_2OEt$ | 810 nM |

[RJ-LC-15-8 Inhibited H1975 Tumor Growth Using a Mechanism Similar to AS1712]

Figure 8A:
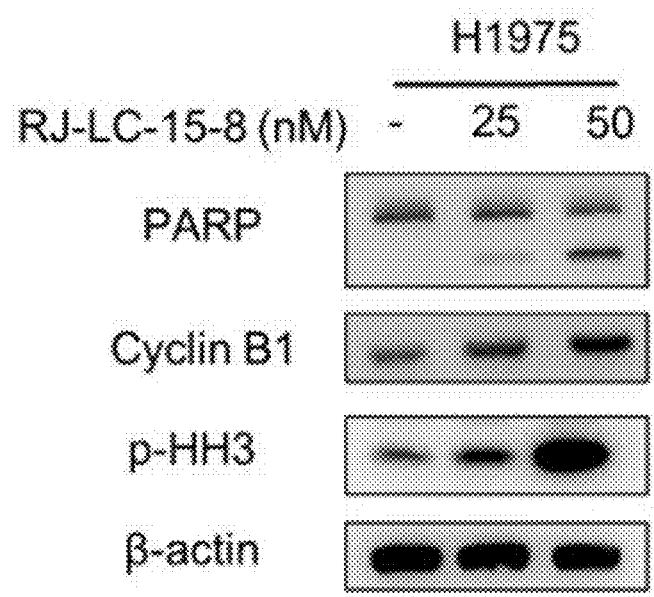
FIGS. 8A to 8G show exemplary compound RJ-LC-15-8 inhibited tumor progression by interfering with microtubule polymerization: H1975 cells were treated with RJ-LC-15-8 for 24 hours prior to observing expression of the indicated proteins (FIG. 8A); microtubule networks in H1975 cells after a 6-hour treatment with 25 nM RJ-LC-15-8 (FIG. 8B); purified tubulin and GTP incubated with the reaction mixture containing buffer alone (control), 5 µM RJ-LC-15-8, 5 µM paclitaxel, 5 µM vincristine, or 5 µM nocodazole, wherein microtubule polymerization was monitored every min for 1 hour (FIG. 8C); H1975 xenograft tumors were treated with intraperitoneally injected DMSO or RJ-LC-15-8 (4 or 8 mg/kg) three times a week for 21 days: tumor volumes (FIG. 8D), body masses (FIG. 8E), wherein data are the mean±SEM; MDA-MB-231 xenograft tumors were treated with intraperitoneally injected DMSO or RJ-LC-15-8 (4 or 8 mg/kg) three times a week for 35 days: tumor volumes (FIG. 8F) and body masses (FIG. 8G), wherein data are the mean±SEM.
Figure 8B:
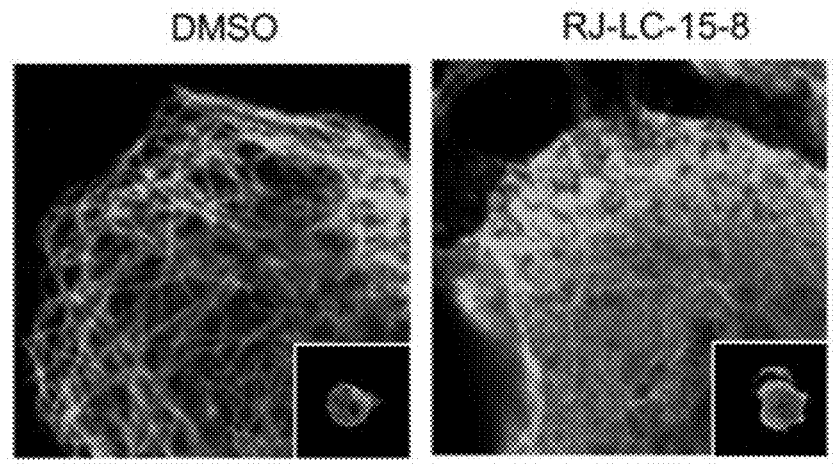
Figure 8C:
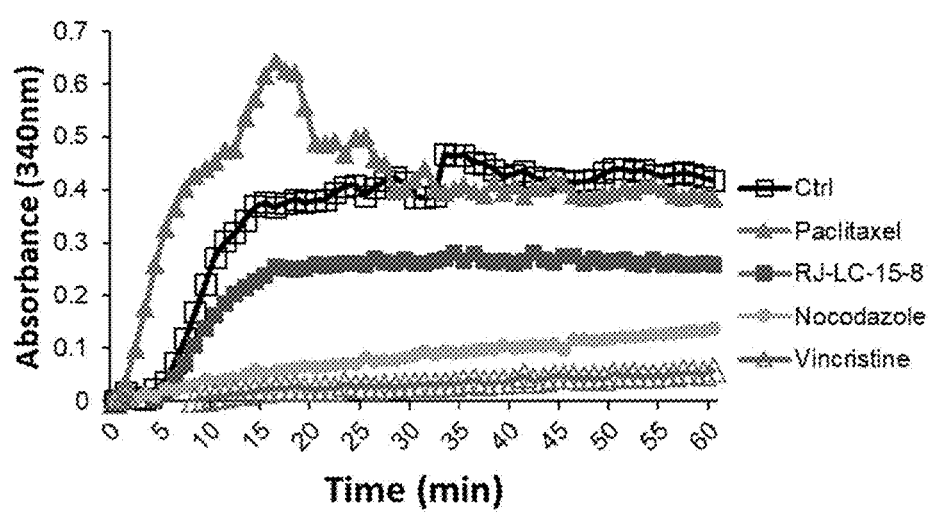
Figure 8D:
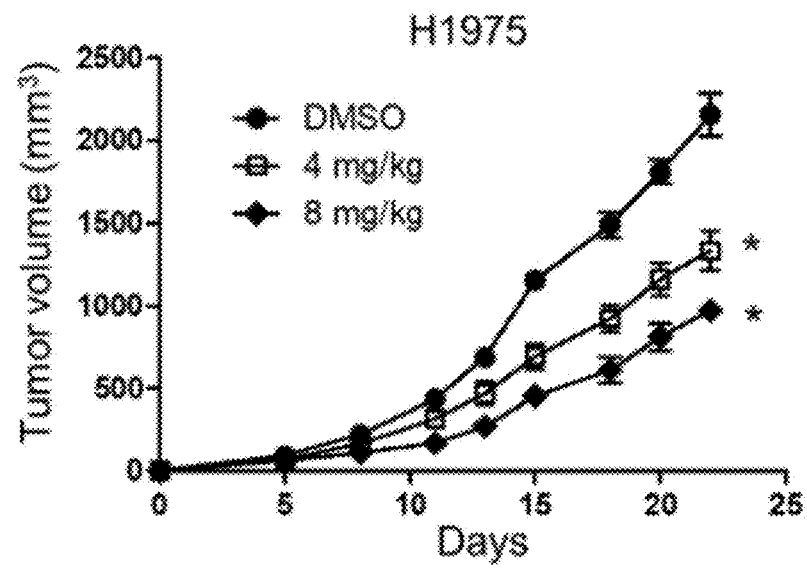
Figure 8E:
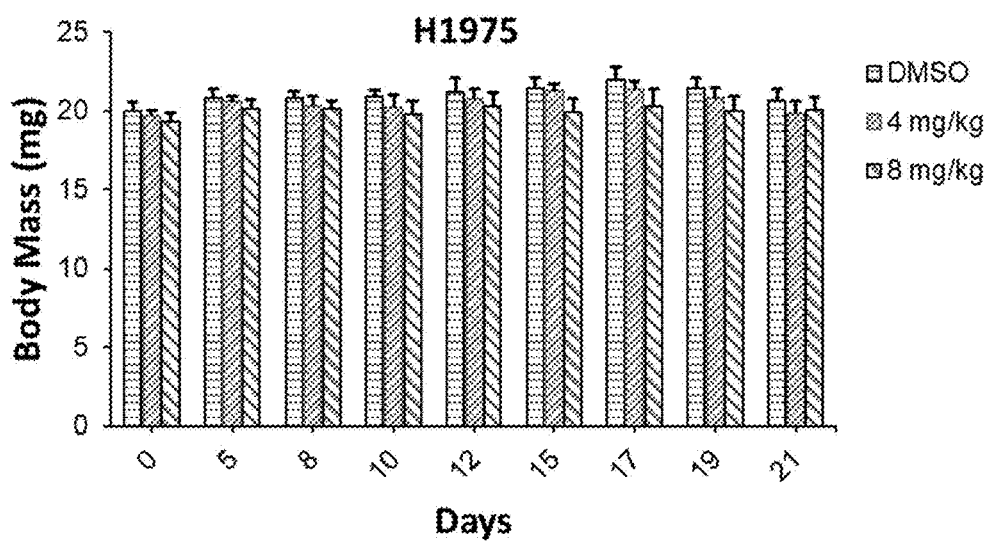
Figure 8F:
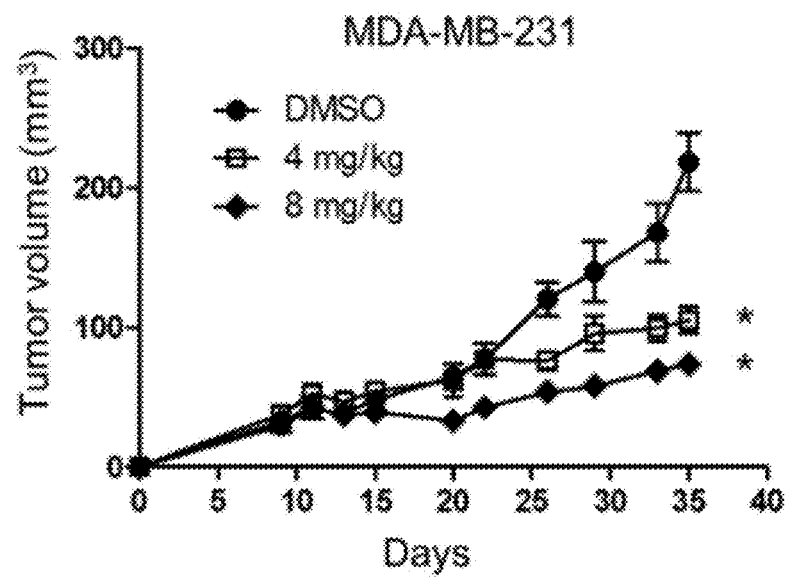
Figure 8G:
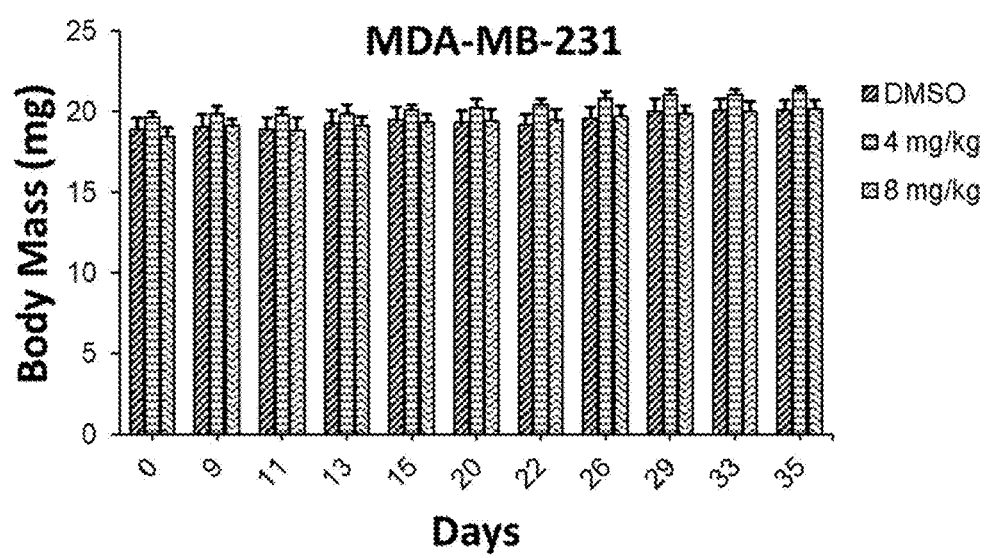

To verify that the mechanism of action of RJ-LC-15-8 is similar to AS1712, additional experiments were performed with H1975 cells. Immunoblotting showed that RJ-LC-15-8 induced cleavage of PARP and increased the expression of the mitotic phase markers cyclinB1 and p-HH3 (FIG. 8A). In situ immunofluorescence of α-tubulin staining showed that RJ-LC-15-8 treatment inhibited microtubule polymerization (FIG. 8B). The in vitro tubulin polymerization assay also showed direct inhibition by RJ-LC-15-8 of microtubule polymerization (FIG. 8C). Next, the anti-tumor ability of RJ-LC-15-8 was evaluated using the H1975 xenograft model, and the data showed that, in comparison with the control group, RJ-LC-15-8 inhibited tumor growth (average tumor size, 2153±126.3 $mm^3$ for the DMSO control treatment and 1333±121.9 $mm^3$ for the 4 mg/kg and 972.5±52.3 $mm^3$ for the 8 mg/kg RJ-LC-15-8 treatments on day 21; both p<0.01; FIG. 8D). At the end of the experiment, it was found that RJ-LC-15-8 treatment had not affected body mass (FIG. 8E). The cytotoxicity of RJ-LC-15-8 was also evaluated against triple-negative breast cancer (TNBC). It was found that RJ-LC-15-8 was more effective than AS1712 in different TNBC cell lines, with $IC_{50}$ values ranging from 21 to 35 nM (Table 4). The MDA-MB-231 xenograft model showed RJ-LC-15-8 could inhibit TNBC tumor growth in comparison with the control group (average tumor size, 218±20.9 $mm^3$ for the DMSO control treatment and 105±9.4 $mm^3$ for the 4 mg/kg and 73.6±8.2 $mm^3$ for the 8 mg/kg RJ-LC-15-8 treatments on day 35; both p<0.05; FIG. 8F). RJ-LC-15-8 treatment did not affect body mass in MDA-MB-231 xenograft model (FIG. 8G).

TABLE 4

Cytotoxic effects of exemplary compound RJ-LC-15-8 on different triple-negative breast cancer cell lines (cells were treated with RJ-LC-15-8 for 72 h, cell viability was examined by the MTS assay, data are the mean of three determinations)

| TNBC | $IC_{50}$ (nM) |
|---|---|
| BT-549 | 21 ± 1.14 |
| Hs578t | 34 ± 4.71 |
| MDA-MB-231 | 35 ± 1.45 |
| 37T | 22 ± 0.61 |
| 82T | 23 ± 1.27 |

Scheme 2. Preparation of Exemplary Compound (A)

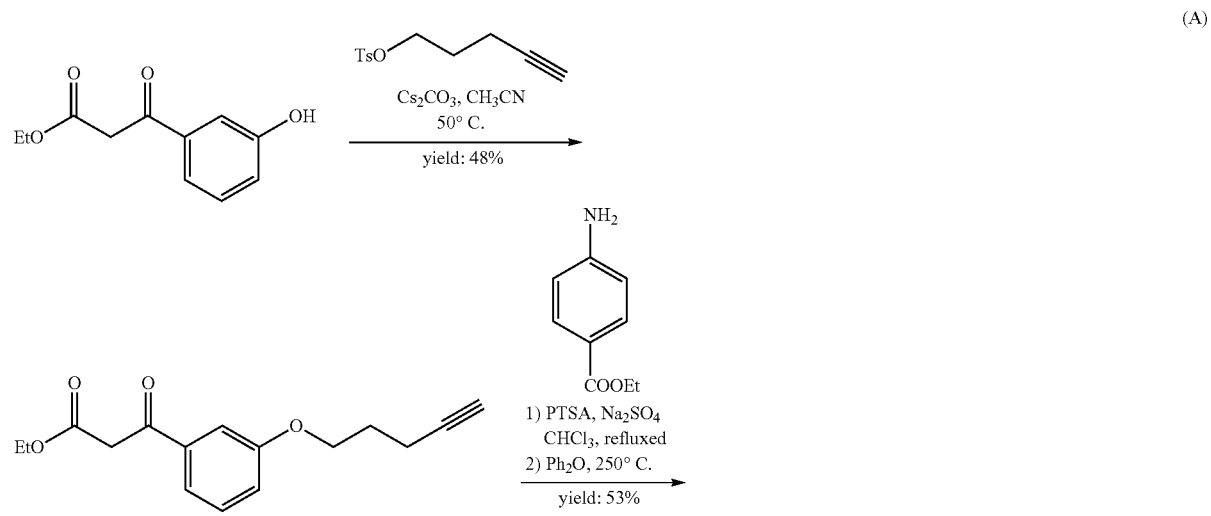

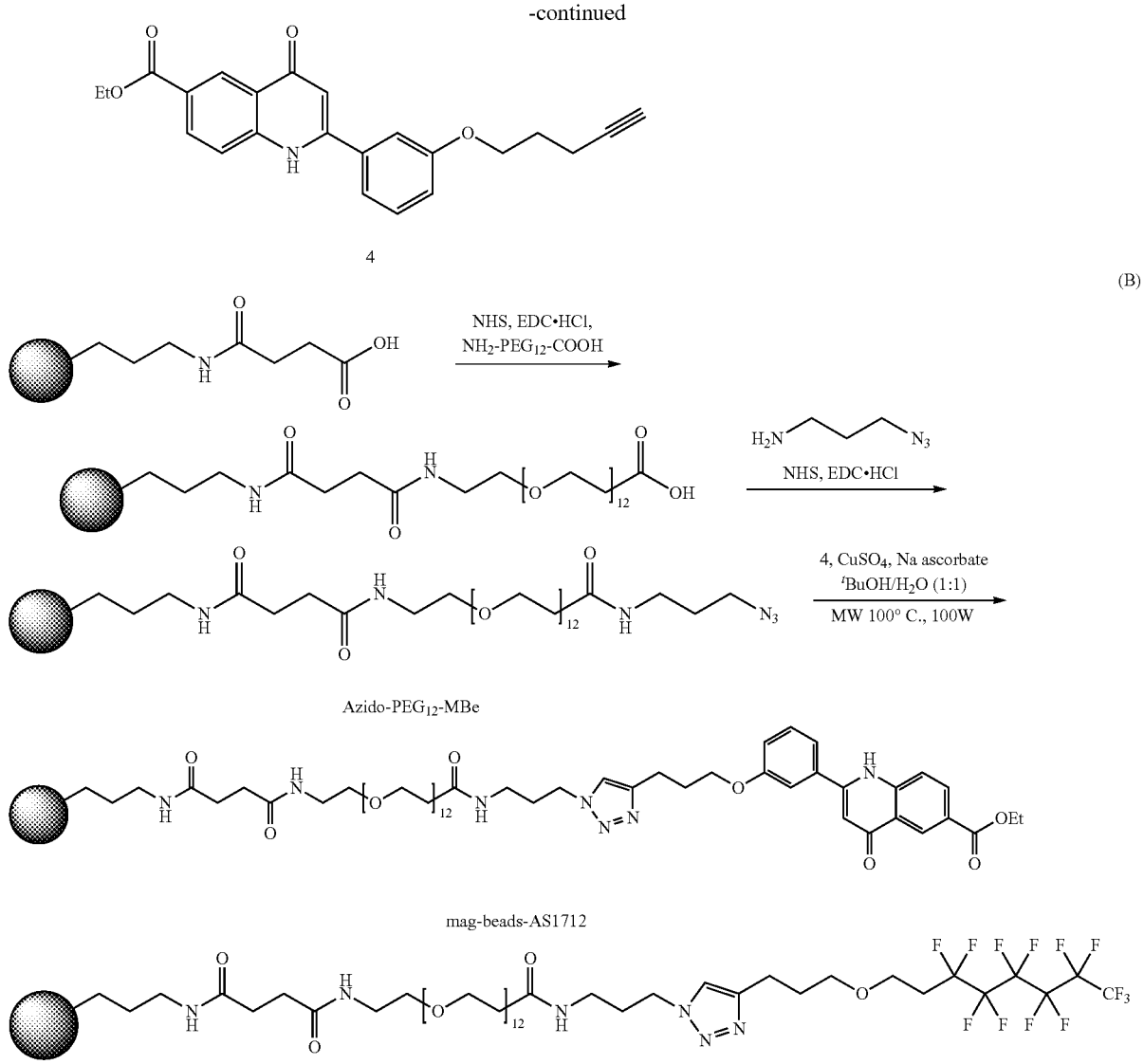

[AS1712 Binds the Colchicine-Binding Pocket of β-Tubulin]

Figure 9A:
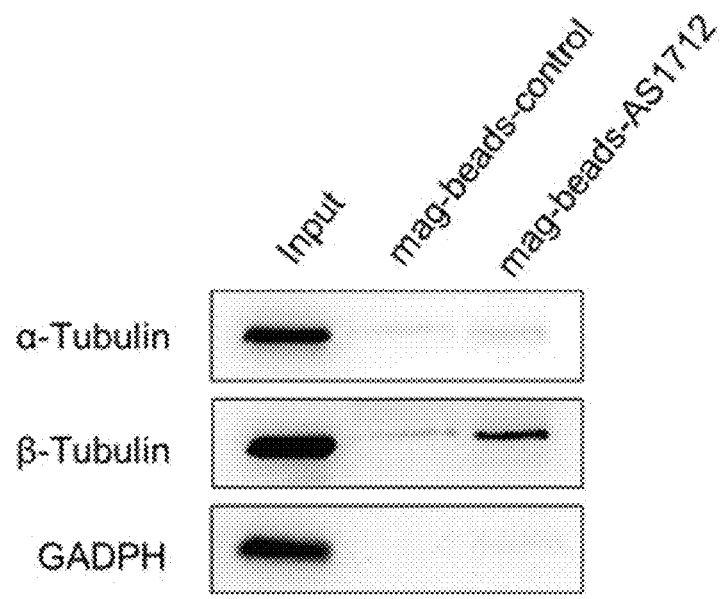
FIGS. 9A to 9H show that exemplary compound AS1712 binds to the colchicine-binding pocket of β-tubulin.
Figure 9B:
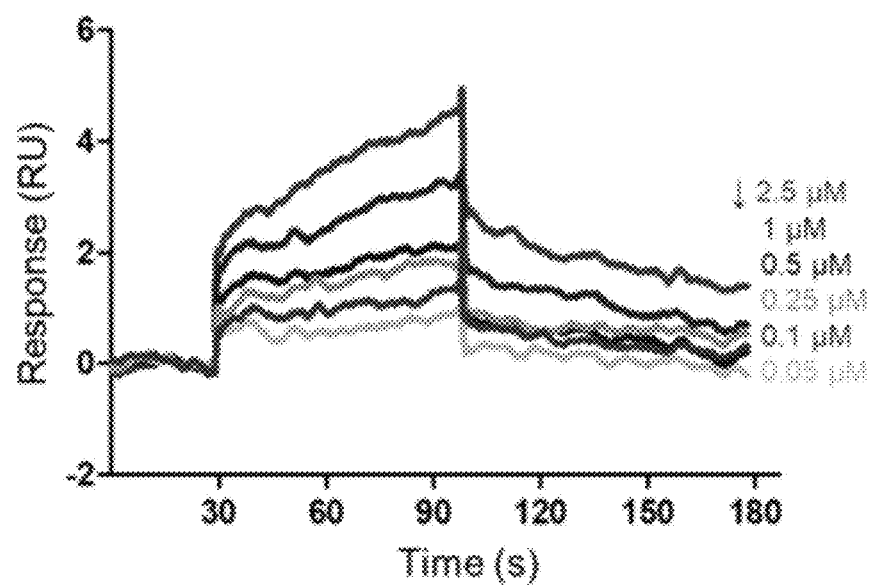

Inhibition by exemplary compound AS1712 of microtubule polymerization led to the possibility that AS1712 directly targeted tubulin. To provide evidence for this possible outcome, a pull-down assay was performed using magnetic beads conjugated with AS1712. First, the alkyne 4 was synthesized via a three-step procedure from ethyl 3-(3-hydroxyphenyl)-3-oxopropanoatealkyne (Scheme 2A) and then coupled to magnetic beads equipped with polyethylene glycol$_{12}$-azido linkers to generate "mag-beads-AS1712" (Scheme 2B). After incubating H1975 lysates separately with mag-beads-AS1712 or mag-beads-control overnight at 4° C., immunoblotting showed that the mag-beads-AS1712 had pulled down only β-tubulin (FIG. 9A). Next, a surface plasmon resonance study was performed to measure the value of the dissociation constant ($K_D$) for the tubulin-AS1712 complex. Different concentrations of AS1712 were injected over a tubulin-immobilized sensor chip surface, and the formation of complexes was monitored. The number of resonance units, which reflected the amount of complex formed, increased in a dose-dependent manner (FIG. 9B). The $K_D$ value for the complex was 13.8 μM as determined by fitting the data to a steady-state model. The data indicated that AS1712 directly interacted with tubulin.

Figure 9C:
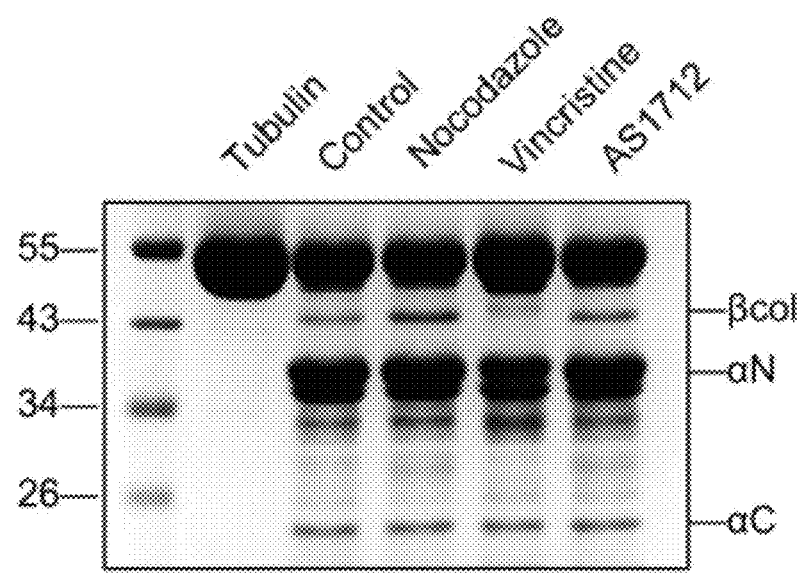
Figure 9D:
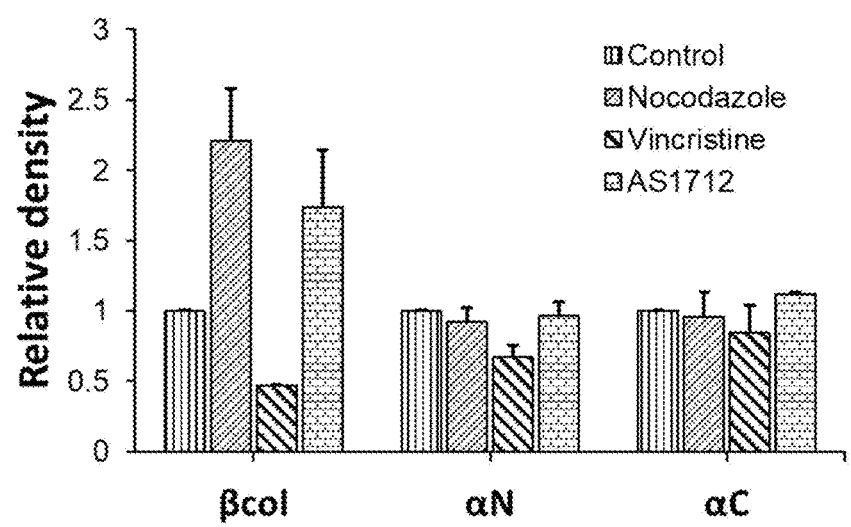
Figure 9E:
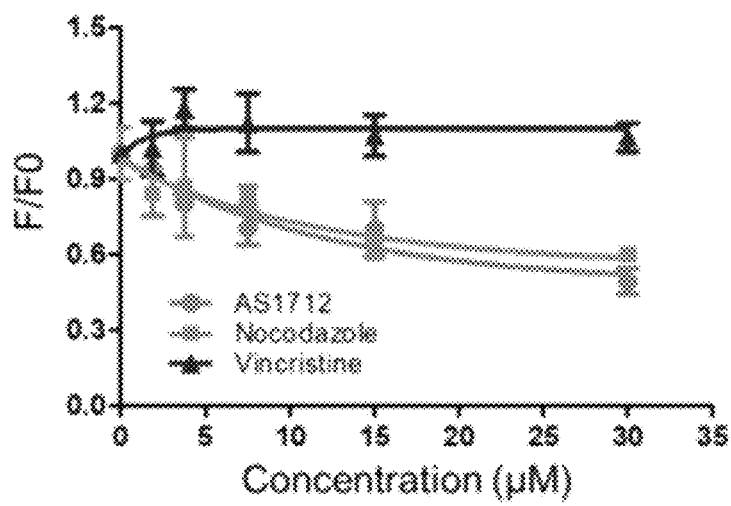

The AS1712-binding site on tubulin was further characterized using a limited proteolysis assay. Two different tubulin-binding sites for microtubule-destabilizing agents are known: the vinca site and the colchicine site. When a drug binds to tubulin, it induces conformational changes that can be probed by a limited trypsin-digestion assay (FIGS. 9C and 9D). The colchicine-site agent nocodazole caused β-tubulin to unfold and produced an increased amount of βcol after a limited trypsin digestion. In contrast, the vinca-site agent vincristine stabilized the α- and β-tubulin folds and decreased the amount of the βcol, αN, and αC fragments produced in comparison with the control digest. The tryptic pattern for the tubulin sample exposed to AS1712 was similar to that of nocodazole (FIGS. 9C and 9D). A competition assay for the colchicine site using colchicine and AS1712 was performed to confirm that AS1712 binds to the colchicine site (FIG. 9E). The presence of AS1712 decreased the colchicine fluorescence in a dose-dependent manner as did nocodazole, whereas vincristine did not.

Figure 9F:
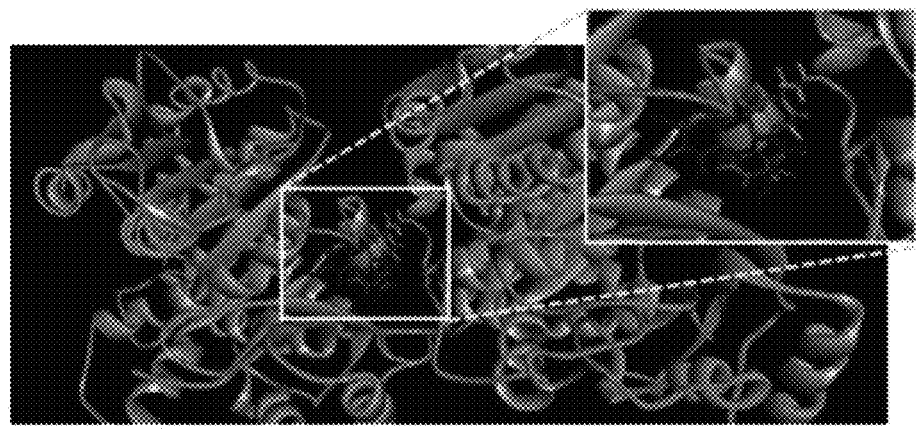
Figure 9G:
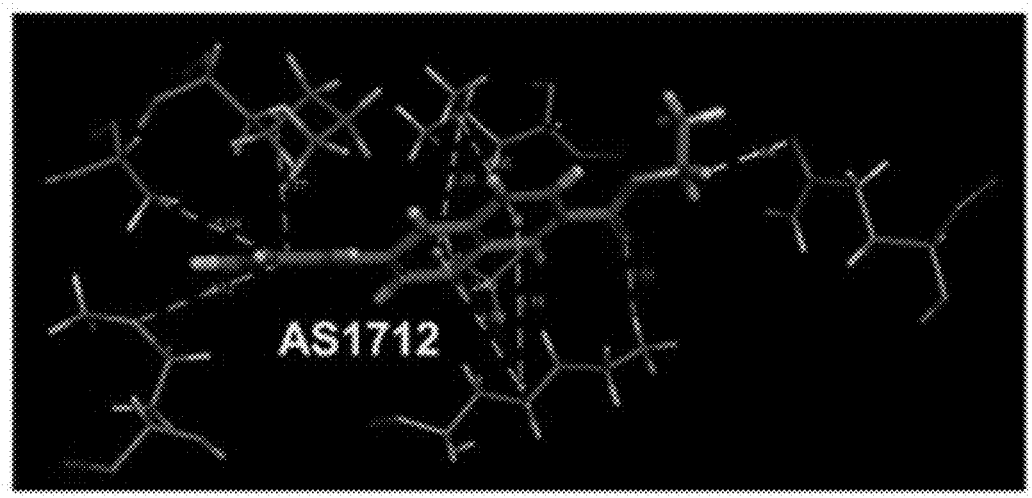
Figure 9H:
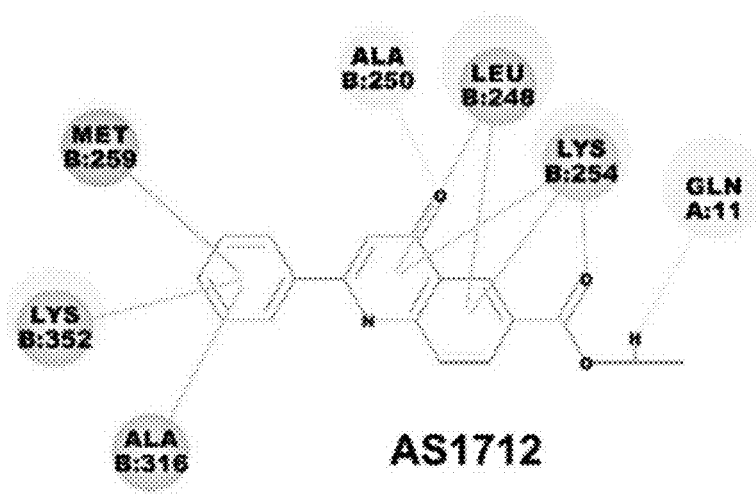

A molecular modeling study was performed to explore the binding mode of AS1712 in the colchicine pocket of a heterodimeric tubulin crystal structure. The orientation of colchicine, which was the original ligand in the crystal structure, was used as a reference. The binding pose of AS1712 was generated by molecular docking into the colchicine binding pocket could be superimposed onto the colchicine structure with an RMSD value of 0.383 Å (FIG. 9F). The docking energy score for the AS1712 complex (−32.8706 kcal/mol) was higher than that for the colchicine complex (−4.47969 kcal/mol). Various types of bonds were found between AS1712 and the α/β-tubulin dimer within a distance of 7 Å (FIG. 9G), including hydrogen bonds between AS1712 and Ala250 and Lys254 of β-tubulin and Gln11 of α-tubulin, as well as pi-bonds with Leu248, Lys254, Met259, Ala316, and Lys352 of the β-tubulin (FIG. 9H). These results suggested that AS1712 binds to β-tubulin at its colchicine-binding pocket.

Exemplary Compound AS1712 Overcame P-Glycoprotein-Mediated Multidrug Resistance

A major mechanism of MTA-induced MDR is P-gp overexpression, which is also the most common resistance mechanism that is clinically relevant to cancer therapy. Therefore, the cytotoxic effects of AS1712 and RJ-LC-15-8 on the KBtax, KBvin, and CEM/VBL cancer cell lines, which overexpress P-gp, were tested. The KBtax and KBvin cell lines were developed by exposure of the human oral cancer cell line KB to paclitaxel and vincristine, respectively. CEM/VBL cells were developed by exposure of the human T-lymphoblastic leukemia cell line CCRF-CEM to vinblastine. The resistance factor (RF) values for the KBtax, KBvin, and CEM/VBL cells against paclitaxel were 10, 70, and 214, respectively, and the values against vincristine were 32, 163, and 440, respectively (Table 5). These results confirmed that these cell lines were resistant to paclitaxel and vincristine. By contrast, AS1712 and RJ-LC-15-8 were cytotoxic to these cell lines, and their effects on these cells were equal to or greater than those on the parent cells (Table 5). Notably, ixabepilone, a second-line MTA used for advanced breast cancer that no longer responds to available chemotherapies, did not effectively inhibit the viability of these multidrug resistant cell lines (Table 5).

The cytotoxicity of AS1712 and RJ-LC-15-8 against triple-negative breast cancer (TNBC) cell line (HDPQ1) and their Paclitaxel-resistant subline (HDPQ1/TAX) was also tested. The RF values for the HDPQ1/TAX cells against paclitaxel was 167. AS1712 and RJ-LC-15-8 were cytotoxic to HDPQ1/TAX cells, and their effects on these cells were equal to or greater than those on the parent cells.

TABLE 6

The cytotoxicity of AS1712 and RJ-LC-15-8 against HDPQ1 cells and their Paclitaxel-resistant sublines

| Compound | HDQP1 IC$_{50}$ (nM) | HDQP1/TAX IC$_{50}$ (nM) | RF$^a$ |
|---|---|---|---|
| AS1712 | 68 ± 5.38 | 63 ± 16.3 | 0.92 |
| RJ-LC-15-8 | 39 ± 0.49 | 40 ± 3.26 | 1.02 |
| Paclitaxel | 5 ± 3.05 | 839 ± 142 | 167 |

$^a$RF, resistance factor (IC$_{50}$ in resistant cell line/IC$_{50}$ in parent cell line).

Figure 10A:
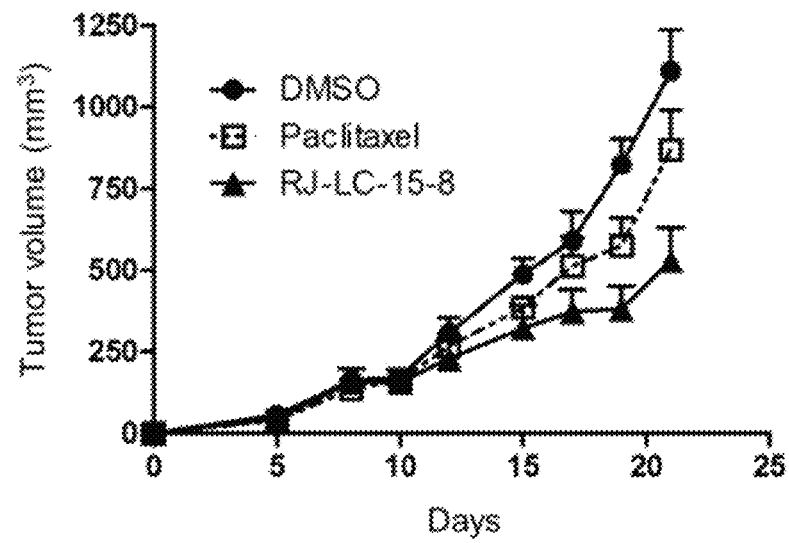
FIGS. 10A to 10E show RJ-LC-15-8 inhibited KBtax tumor growth and induced apoptosis without interfering with P-gp.
Figure 10B:
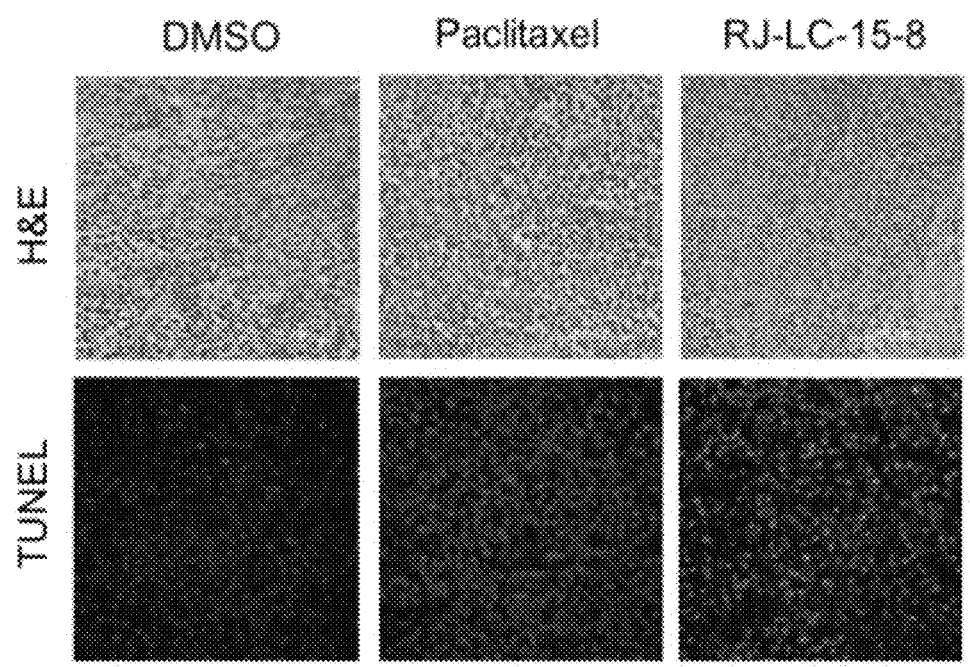
Figure 11A:
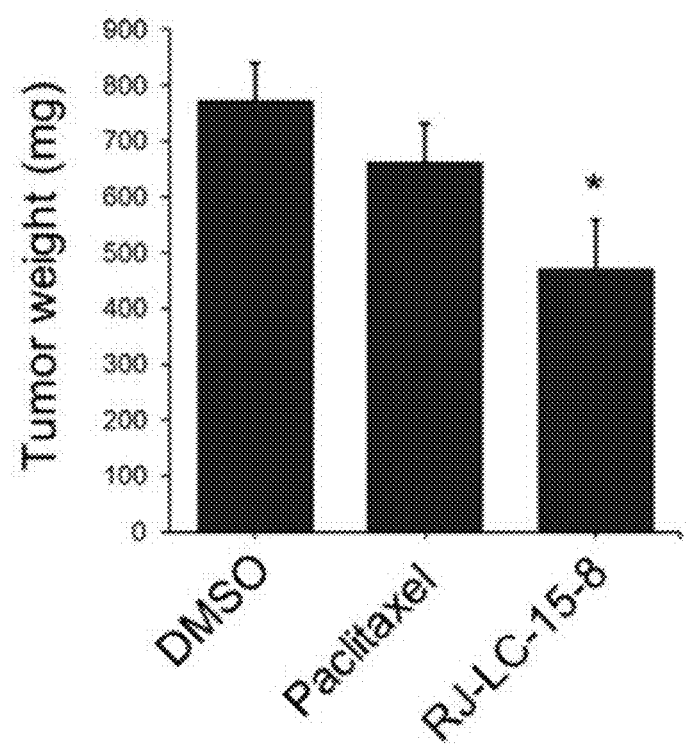
FIGS. 11A to 11B show mice carrying KBtax xenograft tumors treated with DMSO, paclitaxel, or RJ-LC-15-8: tumor weights (FIG. 11A), and body masses (FIG. 11B), wherein data are the mean±SEM; *p<0.05.
Figure 11B:
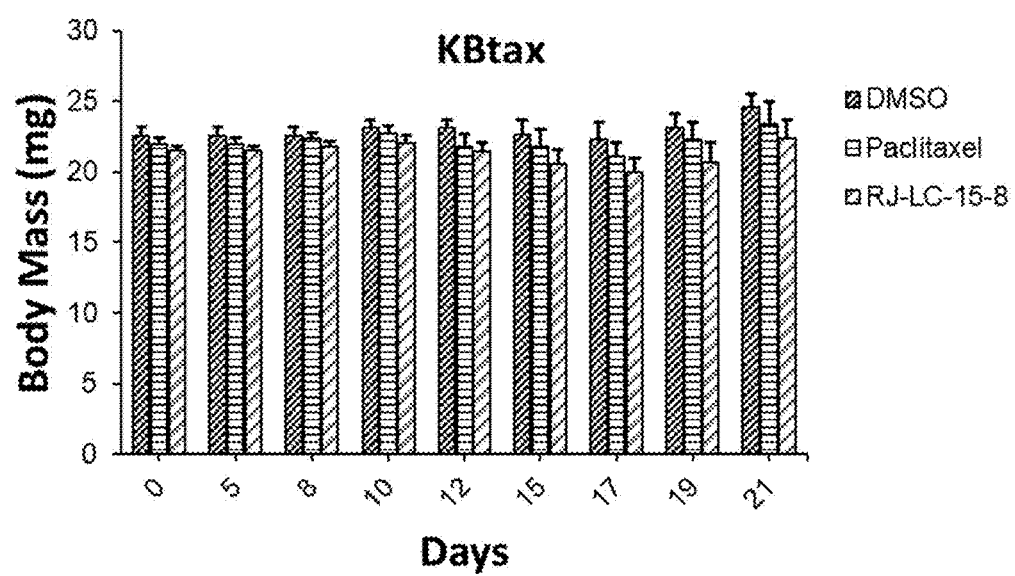

To assess the activity of RJ-LC-15-8 against tumor viability in vivo, BALB/c mice were grafted with KBtax cells and then intraperitoneally injected with DMSO, paclitaxel, (15 mg/kg), or RJ-LC-15-8 (8 mg/kg) three times a week (n=5 per group). After 21 days of treatment, the RJ-LC-15-8 group showed substantially decreased tumor growth as compared with the paclitaxel and DMSO groups (average tumor size, 1109±128.3 mm³ for DMSO; 868.7±121.4 mm³ for paclitaxel; and 528.4±101.6 mm³ for RJ-LC-15-8; FIGS. 10A and 11A). TUNEL staining of the tumor tissues showed that the RJ-LC-15-8 treatment induced apoptosis (FIG. 10B). Body mass and serum biochemical markers for liver and kidney functions were not negatively affected at the end of the experiment (FIG. 11B and Table 7). Thus RJ-LC-15-8 inhibited the growth of an MDR-type cancer tumor with low toxicity.

TABLE 7

Serum biochemical marker activities against KBtax xenograft tumors (data are the mean ± SEM)

| | ALT(IU/L) | AST(IU/L) | BUN(mg/dl) | Cre(mg/dl) |
|---|---|---|---|---|
| DMSO | 32.7 ± 4.8 | 94.2 ± 12.5 | 17.8 ± 1.1 | 0.22 ± 0.02 |
| Paclitaxel | 48.4 ± 13.5 | 102.8 ± 18.9 | 19 ± 1.3 | 0.16 ± 0.02 |
| RJ-LC-15-8 | 64 ± 10.8 | 120.7 ± 27.5 | 18.2 ± 1 | 0.26 ± 0.04 |

Figure 10C:
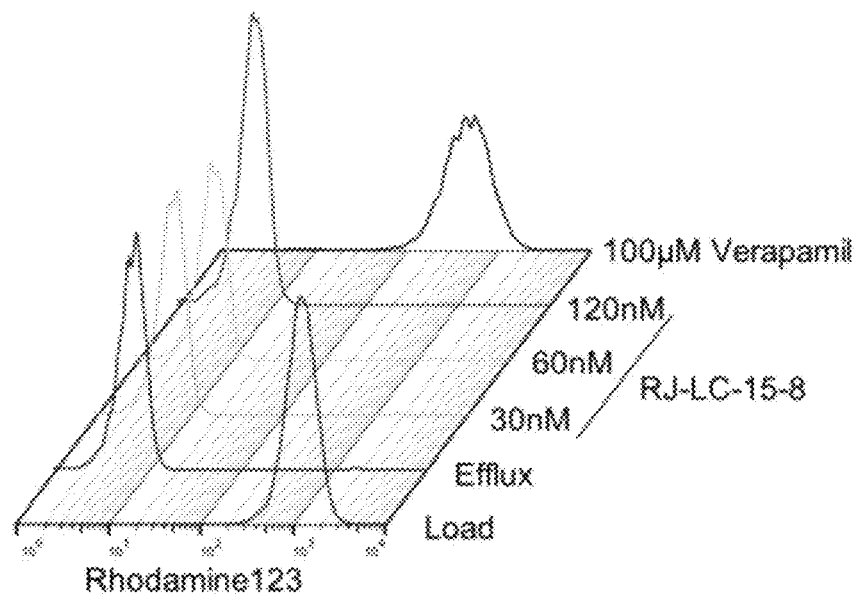
Figure 10D:
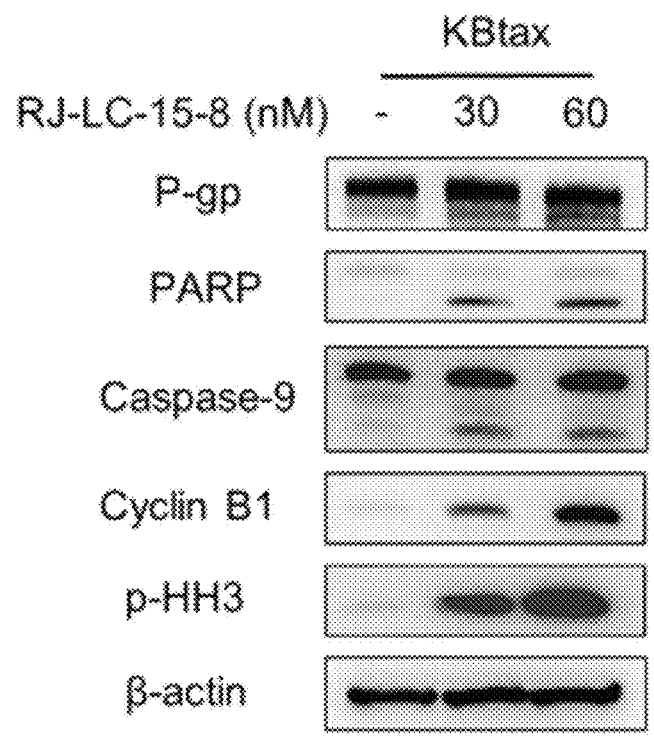

Because RJ-LC-15-8 displayed inhibitory activity against the KBtax cells, it was sought to be determined whether its effects were related to P-gp, either through a direct inhibition or because it is not a P-gp substrate. Therefore, the effects of RJ-LC-15-8 on P-gp efflux activity and its expression were examined. A rhodamine efflux assay showed that RJ-LC-15-8 did not directly inhibit pump activity in KBtax cells but that verapamil, a known P-gp inhibitor, did (FIG. 10C). The immunoblotting study showed that RJ-LC-15-8 did not affect P-gp expression in KBtax cells, whereas it induced cleavage of the apoptosis markers PARP and caspase-9 and increased the expression of the mitotic phase markers cyclin B1 and p-HH3 (FIG. 10D). In situ immunofluorescence staining of α-tubulin showed that RJ-LC-15-8 treatment inhibited microtubule polymerization and disrupted mitotic

TABLE 5

The cytotoxicity of AS1712 against KB, CCRF-CEM cells and their multidrug resistant sublines

| Compound | KB IC$_{50}$ (nM) | KBtax IC$_{50}$ (nM) | RF$^a$ | KBvin IC$_{50}$ (nM) | RF | CCRF-CEM IC$_{50}$ (nM) | CEM/VBL IC$_{50}$ (nM) | RF |
|---|---|---|---|---|---|---|---|---|
| AS1712 | 37 ± 0.27 | 30 ± 0.65 | 0.81 | 37 ± 0.77 | 1 | 45 ± 0.45 | 45 ± 0.45 | 0.97 |
| RJ-LC-15-8 | 34 ± 0.39 | 30 ± 1.35 | 0.88 | 35 ± 0.88 | 1 | 20 ± 1.71 | 16 ± 0.52 | 0.8 |
| Paclitaxel | 10 ± 0.32 | 101 ± 5.52 | 10 | 708 ± 46.9 | 70 | 4 ± 0.02 | 857 ± 9.89 | 214 |
| Vincristine | 5 ± 0.31 | 49 ± 2.96 | 32 | 817 ± 47.4 | 163 | 3 ± 0.04 | 1320 ± 20.6 | 440 |
| Ixabepilone | 8 ± 0.37 | 35 ± 0.71 | 4.3 | 193 ± 24.2 | 24 | 3 ± 0.06 | 150 ± 6.59 | 50 |

Figure 10E:
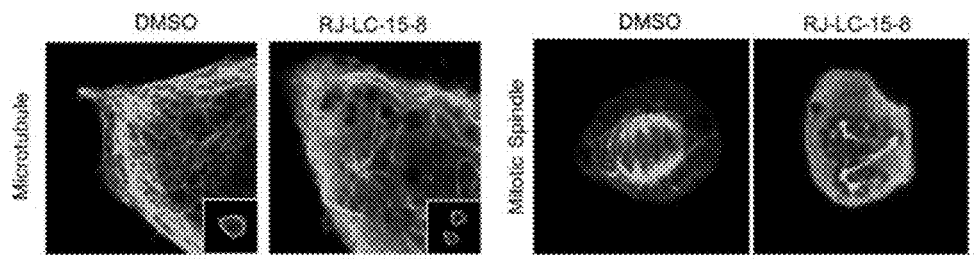

$^a$RF, resistance factor (IC$_{50}$ in resistant cell line/IC$_{50}$ in parent cell line).

spindle organization (FIG. 10E). RJ-LC-15-8 induced apoptosis in multidrug resistant cells without interfering directly with P-gp expression OR activity and, more broadly, the mechanism of cytotoxicity of RJ-LC-15-8 was not related to P-gp.

Experimental Section

General. Anhydrous solvents were freshly dried and purified by conventional methods prior to use. The progress of all the reactions were monitored by TLC, using TLC glass plates precoated with silica gel 60 F254 (Merck). Column chromatography was performed on silica gel Geduran® Si 60 (Merck). $^1$H and $^{13}$C NMR spectra were recorded with Bruker AV-III 400 MHz, Bruker N-600, Bruker AV-400, or AV-500 MHz spectrometers and chemical shifts were measured in δ (ppm) with residual solvent peaks as internal standards (CDCl$_3$, δ 7.26 ppm in $^1$H NMR, δ 77 ppm in $^{13}$C NMR; CD$_3$OD, δ 3.31 ppm in $^1$H NMR, δ 49.0 ppm in $^{13}$C NMR; DMSO-d$_6$, δ 2.50 ppm in $^1$H NMR, δ 39.52 ppm in $^{13}$C NMR). Coupling constants J, measured in Hz. Coupling constants (J) are reported in hertz, and the splitting abbreviations used were as follows: s, singlet; d, doublet; t, triplet; m, multiplet. Melting points were recorded on Buchi 565 apparatus.

Antibodies against PARP, caspase-3, caspase-8, caspase-9, Bax, and MDR-1 were purchased from Cell Signaling. Antibodies against cyclin B1, cyclin A, GADPH, and MTCO1 were obtained from Santa Cruz. Antibodies against α-tubulin, β-tubulin, and β-actin were from Sigma Aldrich. The antibody preparation against cytochrome c was from Abcam. The antibody preparation against p-HH3 (S10) was from Merck Millipore. Horseradish peroxidase☐labeled anti-mouse and anti-rabbit antibodies were purchased from Santa Cruz. Fluorescein isothiocyanate☐labeled anti-mouse antibody was from Thermo Fisher Scientific. Roswell Park Memorial Institute (RPMI) 1640 medium, Dulbecco's Modified Eagle medium (DMEM), and fetal bovine serum were purchased from GIBCO Life Technologies. The in situ cell death detection (TUNEL) kit was purchased from Roche. The tubulin polymerization assay kit was obtained from Cytoskeleton. The BCA protein assay kit was purchased from Pierce. The Series S Sensor Chip SA and HBS-EP+ running buffer were obtained from GE Healthcare.

Identification of AS1712 by High-Throughput Screening

Through high-throughput screening, a library of 2 million compounds was used to evaluate anti-proliferation activities against H1975 lung cancer cells at 10 μM concentration. The coefficient of variation (CV %) and Z' values of the primary screening were determined as 4.9% and 0.58, respectively. In the first screening, ~6,800 small molecules exhibited >80% growth inhibition of H1975 cells. These compounds were further screened against other eight lung cancer cells, including clinical isolates (CL25, CL83, CL97, CL100, CL141, CL152), an ATCC cell line (PC-9) and its derivative resistant clone (PC9/IR). By filtered with the criteria of IC$_{50}$≤6 μM for all tested cells, only 232 small molecules were kept for the further study. AS1712 was one of these molecules displaying superior cytotoxic effects on lung cancer cells and a notable therapeutic window between cancer cells and normal cells.

Cell Lines and Cell Culture

CL1-0 cells were isolated from a 64-year-old male patient with a poorly differentiated adenocarcinoma. PC9 cells were obtained from Dr. C. H. Yang (Graduate Institute of Oncology, Cancer Research Center, National Taiwan University). Molt4 leukemia cells were obtained from Dr. Tang K. Tang (Institute of Biomedical Sciences, Academia Sinica). KB, KBtax, KBvin, CCRF-CEM, and CEM/VBL cells were obtained from Dr. T. C. Lee (Institute of Biomedical Sciences, Academia Sinica). The KB cell line was originally derived from an oral epidermal carcinoma and has been shown to be contaminated with HeLa cells. Hs578T, MDA-MB-231, 37T, and 82T cells were obtained from Dr. Y. S. Lu (Department of Internal Medicine, College of Medicine, National Taiwan University). 37T and 82T cells were isolated from breast cancer patients and cultured in 2% IH medium. SKOV-3, IGR-OV1, Ovcar-3, HCT116, HT-29, Colon205, SW620, Du-145, and PC-3 cells were obtained from Dr. S. L. Yu (Department of Clinical Laboratory Sciences and Medical Biotechnology, National Taiwan University). The NBE cell line was provided by Dr. Reen Wu (Department of Anatomy, Physiology and Cell Biology, University of California Davis) and cultured in bronchial epithelial basal medium. SAS and OECM1 cells were obtained from Dr. C. Y. Chen (Graduate Institute of Health Industry Technology and Research Center for Industry of Human Ecology, Chang Gung University of Science and Technology). A549, H1975, BT-549, and HFB cells were purchased from American Type Culture Collection (Rockville, MD, USA). In general, cells were cultured in RPMI 1640 medium or DMEM supplemented with 10% heat-inactivated fetal bovine serum and 1% penicillin-streptomycin in a humidified incubator under an atmosphere of 5% CO$_2$ and 95% air.

Cell Cytotoxicity Assay

Cells were seeded into the wells of 96-well plates (2000 cells/well). After an overnight culture, the cells were treated with different concentrations of a compound for 72 h. The CellTiter 96 AQueous one-solution cell proliferation assay (MTS) reagent was used to determine cytotoxicity. After treatment with a compound, 20 μL of the MTS reagent was added to each well and the plates were incubated at 37° C. for 1-4 h. Next, the absorbance at 490 nm of the culture medium in each well was determined using a VersaMax microplate reader (Molecular Devices).

Colony Formation Assay

Cells were seeded into the wells of six-well plates (1000 cells/well). After overnight culture, the cells were treated with various concentrations of AS1712 for 2 weeks. Then, the colonies in each well were fixed with 3.7% paraformaldehyde, stained with 0.04% crystal violet, and dissolved in 1 ml DMSO. The absorbance at 590 nm of each DMSO solution was read using the VersaMax microplate reader.

Cell Cycle Analysis

After treatment, cells were trypsinized and fixed in ice-cold 70% ethanol overnight. Fixed cells were washed with PBS and stained with 0.5 mL of a propidium iodide (10 μg/mL)/RNase (20 μg/mL) solution for 30 minutes. The cellular DNA content was analyzed with a FACSCanto flow cytometer (Becton Dickinson).

Immunoprecipitation and Immunoblotting

The cells were harvested and lysed in RIPA buffer (20 mM Tris-HCl, 150 mM NaCl, 1 mM Na$_2$EDTA, 1% sodium deoxycholate, 1% IGEPAL CA-630, 0.1% SDS, pH 7.5) with protease inhibitors (Roche). Protein concentration was measured by the BCA assay. For immunoprecipitation, protein extracts were incubated with mag-beads-AS1712 or mag-beads-control at 4° C. overnight and then washed five times with PBS before immunoblotting. For immunoblotting, equivalent amounts of denatured proteins were separated through SDS-PAGE gels and then transferred to PVDF membranes (Millipore), which were each blocked with 5% nonfat milk in PBS and 0.1% Tween-20 (Sigma Aldrich) for 1 h. Then each membrane was incubated with a primary antibody overnight at 4° C., followed by incubation with a horseradish peroxidase conjugated secondary antibody for 1 h at room temperature. The signal was visualized by enhanced chemiluminescence detection, and images were acquired using a BioSpectrum Imaging System (UVP).

Immunofluorescence Staining

Cells or microtubule asters were fixed with 3.7% paraformaldehyde, permeabilized with 0.1% Triton X-100, stained with anti-α-tubulin (1:1000 dilution) at 4° C. overnight, and then incubated with a fluorescein isothiocyanate☐conjugated secondary antibody (1:500) at 37° C. for 1 h. Cells were then mounted with Prolong Gold Antifade Reagent and stained with DAPI (Thermo Fisher Scientific), after which images were acquired with an LSM 700 laser scanning confocal microscope (Carl Zeiss).

In Vivo Microtubule Assembly Assay

Cell samples were treated with a compound for 6 h, and the cells were then harvested and were lysed in 20 mM Tris-HCl, 1 mM $MgCl_2$, 2 mM EGTA, 0.5% IGEPAL CA-630, 2 mM PMSF, 200 U/mL aprotinin, and a protease inhibitor cocktail (pH 6.8). After centrifugation of each lysate at 16,000 rpm for 15 min at room temperature, its supernatant containing soluble monomeric tubulin and the particulate fraction containing polymerized tubulin were separately subjected to immunoblotting.

In Vitro Tubulin Polymerization Assay

Reagents from a Tubulin Polymerization Assay kit (Cytoskeleton) were used according to the manufacturer's instructions. Purified porcine tubulin (4 mg/mL; >99% purity) in G-PEM buffer (80 mM PIPES, 2 mM $MgCl_2$, 0.5 mM EGTA, 1 mM GTP, 15% glycerol, pH 6.9) was mixed with each test compound in the wells of a 96-well plate. Then, the $A_{340}$ value was recorded each minute for 1 h at 37° C. with the VersaMax microplate reader.

In Vitro Microtubule Nucleation Assay

Purified centrosomes were incubated with or without AS1712 and with porcine tubulin (Cytoskeleton) in 80 mM PIPES, 1 mM $MgCl_2$, 1 mM EGTA, and 1 mM GTP, pH 6.8 for 8 min at 37° C. Microtubule asters were fixed in 1% glutaraldehyde, sedimented onto acid-treated coverslips, and finally subjected to immunofluorescence with anti-α-tubulin. The fiber lengths of the microtubule asters were measured using MetaMorph image analysis software (n=20/group).

Binding Affinity Assay

Surface plasmon resonance technology was used to analyze the binding affinity of AS1712 for tubulin. A Series S Sensor Chip SA was conditioned with three consecutive 1-min injections of 1 M NaCl in 50 mM NaOH, and then 50 μg/mL biotin-tubulin (Cytoskeleton) was immobilized onto the sensor chip surface in a Biacore T200 system (GE Healthcare) to attain 3,000 resonance units. One flow cell on the chip was left free to serve as the negative control. Biocytin (Sigma Aldrich) was used to block any remaining unmodified streptavidin sites. Different concentrations of AS1712 in 10 mM HEPES, 150 mM NaCl, 3 mMEDTA, and 0.05% surfactant P20, pH 7.4 were separately injected over the sensor chip surface to measure the association and dissociation of AS1712 and tubulin at 25° C. The value of $K_D$ was calculated using the steady-state fitting mode in Biacore T200 Evaluation Software.

Limited Proteolysis Assay

Tubulin (1 mg/mL) was incubated individually with a test compound for 30 min at 30° C. in 0.1 M morpholino ethanesulfonic acid, 1 mM $MgCl_2$, 1 mM EGTA, pH 6.9, and then 25 μg/mL trypsin (TPCK-treated, Sigma Aldrich; 1:40 [w/w] trypsin/tubulin) was added to the solution for a 10-min digestion at 4° C. Samples were electrophoresed through a 15% SDS-PAGE gel and stained with Coomassie brilliant blue R250. The images were scanned and quantified using a BioSpectrum Imaging System (UVP).

Colchicine Competition Assay

Tubulin (3 M) and colchicine (3 M) were incubated with the various concentrations of AS1712, nocodazole, or vincristine in 80 mM PIPES, 2 mM $MgCl_2$, 0.5 mM EGTA, pH 6.9 at 37° C. for 1 h. Fluorescence intensities (excitation and emission wavelengths at 365 and 435 nm, respectively) were recorded using an Infinite M200 plate reader (Tecan). Fluorescence values were normalized to the DMSO control.

Molecular Modeling

The DMA-colchicine-bound tubulin heterodimer crystal structure (PDB-ID: 1SA0) was used for the docking study. Molecular docking was conducted using Discovery Studio (Accelrys Inc.) to assess the probably binding mode of AS1712 in the colchicine-binding site of tubulin. The initial crystal structure was prepared using the Prepare Protein protocol in Discovery Studio that protonates the structure and inserts missing loop regions. The docking was performed using the CDOCKER docking protocol in Discovery Studio based on the grid-based molecular docking method and the CHARMm force field for binding-energy minimization. Random ligand conformations were generated from each initial ligand structure via random rotations and high-temperature molecular dynamics. The random conformations were refined by grid-based simulated annealing and minimization. The pose was each chosen based on their highest docking score for further interaction analyses. The post-docking analyses were performed using the View Interactions tool in Discovery Studio to identify the ligand-protein hydrogen bonds, bumps, and Pi interactions.

Rhodamine Efflux Assay

KBtax cells ($2.5 \times 10^5$/test) were collected and held on ice for 1 h in cold medium with 5 mM rhodamine. Then, the cells were resuspended in medium warmed to 37° C. with one of the indicated compounds and incubated for 1 h in a water bath at the same temperature for efflux determination. The fluorescence intensities were quantified by FACSCanto flow cytometry.

Xenograft Tumor Model

Using the H1975, MDA-MB-231, and KBtax xenograft models, tumors were established after inoculation into the right flanks of 6-week-old BALB/c nude mice (NARLabs, Taipei, Taiwan). After establishment of the tumors, vehicle and test compounds, which had been dissolved in DMSO, were each injected intraperitoneally into a separate group of animals three times per week. The body mass of each animal and tumor volumes were measured before each drug delivery. Tumor volume was calculated as $0.5W^2L$ (with W being the width of the smaller diameter and L being the length of the larger diameter). The animal experiment was carried out in accordance with the procedures and guidelines of the Institutional Animal Care and Use Committee, Institute of Biomedical Sciences, Academia Sinica.

General Procedure A for Synthesis of AS1712 and Analogues

A solution of 4-aniline (0.616 mmol), benzoylacetate (0.71 mmol), TsOH·$H_2O$ (0.03 mmol) and $Na_2SO_4$ (6.16 mmol) in $CHCl_3$ (3 ml) was stirred and refluxed for 48 h. The reaction mixture was concentrated in vacuo and washed with hexane or $Et_2O$. Next, collected filtrate and evaporated to get imine. The imine was dissolved in diphenylether (1 ml) and heated to 250° C. for 10 mins. The reaction mixture was cooled to room temperature. After trituration with $Et_2O$, the product was collected by filtration.

Ethyl 4-oxo-2-phenyl-1,4-dihydroquinoline-6-carboxylate (AS1712)

The title compound was prepared by the above general procedure A. Yield: 79%; Mp 308-311° C.; $^1$H NMR (600 MHz, DMSO-d$_6$) δ 11.98 (s, 1H), 8.71 (s, 1H), 8.17 (dd, J=8.7 Hz, J=1.5 Hz, 1H), 7.87-7.83 (m, 3H), 7.61-7.58 (m, 3H), 6.43 (s, 1H), 4.35 (q, J=7.1 Hz, 2H), 1.36 (t, J=7.2 Hz, 3H); $^{13}$C NMR (150 MHz, DMSO-d$_6$) δ 177.1, 165.8, 151.4, 144.1, 134.4, 132.0, 131.2, 129.5, 128.0, 127.5, 124.8, 124.6, 120.0, 108.7, 61.3, 14.7.

Ethyl 2-(4-methoxyphenyl)-4-oxo-1,4-dihydroquinoline-6-carboxylate (2c)

The title compound was prepared by the above general procedure A. Yield: 73%; Mp 325-330° C.; IR (neat): 3260, 3159, 2981, 1697, 1635, 1574, 1538, 1486, 1456, 1395, 1248, 1230, 1191, 1124, 1022, 820, 786 cm$^{-1}$; $^1$H NMR (600 MHz, DMSO-d$_6$) δ 11.84 (s, 1H), 8.69 (s, 1H), 8.15 (dd, J=8.7 Hz, J=2.2 Hz, 1H), 7.95-7.90 (m, 2H), 7.83 (d, J=8.5 Hz, 1H), 7.14 (d, J=8.5 Hz, 1H), 6.40 (s, 1H), 4.35 (q, J=7.2 Hz, 2H), 3.85 (s, 3H), 1.36 (t, J=7.1 Hz, 3H); $^{13}$C NMR (150 MHz, DMSO-d$_6$) δ 177.2, 165.8, 161.8, 150.9, 143.9, 132.0, 129.5, 127.5, 126.3, 124.7, 124.5, 119.7, 114.9, 108.0, 61.3, 56.0, 14.7. ESI-HRMS (m/z): Calcd for $C_{19}H_{16}NO_4$ [(M)-] 322.1079. found [(M)-] 322.1084.

Ethyl 2-(4-fluorophenyl)-4-oxo-1,4-dihydroquinoline-6-carboxylate (2d)

The title compound was prepared by the above general procedure A. Yield: 83%; Mp 335-340° C.; IR (neat): 3261, 3145, 3083, 2979, 2912, 1711, 1639, 1552, 1502, 1487, 1417, 1391, 1257, 1223, 1130, 1111, 1027, 923, 844, 774, 761 cm$^{-1}$; $^1$H NMR (600 MHz, DMSO-d$_6$) δ 11.97 (s, 1H), 8.70 (s, 1H), 8.18 (dd, J=8.5 Hz, J=1.9 Hz, 1H), 7.95-7.90 (m, 2H), 7.83 (d, J=9.0 Hz, 1H), 7.44 (t, J=8.5 Hz, 1H), 6.42 (s, 1H), 4.35 (q, J=7.1 Hz, 2H), 1.36 (t, J=7.2 Hz, 3H); $^{13}$C NMR (150 MHz, DMSO-d$_6$) δ 177.2, 165.8, 164.8, 163.2, 150.2, 143.9, 132.1, 130.7, 130.5, 130.5, 127.5, 124.9, 124.5, 119.8, 116.6, 116.4, 108.9, 61.3, 14.7. ESI-HRMS (m/z): Calcd for $C_{18}H_{13}NO_3F$ [(M)-] 310.0879. found [(M)-] 310.0871.

Ethyl 2-(4-bromophenyl)-4-oxo-1,4-dihydroquinoline-6-carboxylate (2e)

The title compound was prepared by the above general procedure A. Yield: 87%; Mp 345-350° C.; IR (neat): 3255, 3140, 3085, 2976, 1711, 1638, 1571, 1491, 1409, 1364, 1269, 1254, 1074, 1010, 914, 820, 776, 764 cm$^{-1}$; $^1$H NMR (600 MHz, DMSO-d$_6$) δ 11.99 (s, 1H), 8.70 (s, 1H), 8.18 (dd, J=8.6 Hz, J=1.9 Hz, 1H), 7.85-7.79 (m, 5H), 6.45 (s, 1H), 4.35 (q, J=6.9 Hz, 2H), 1.37 (t, J=7.2 Hz, 3H); $^{13}$C NMR (150 MHz, DMSO-d$_6$) δ 177.3, 165.7, 150.0, 143.9, 133.4, 132.5, 132.2, 130.1, 127.5, 124.9, 124.8, 124.6, 119.8, 109.0, 61.3, 14.7. ESI-HRMS (m/z): Calcd for $C_{18}H_{13}NO_3Br$ [(M)-] 370.0079. found [(M)-] 370.0081.

Ethyl 2-(4-hydroxyphenyl)-4-oxo-1,4-dihydroquinoline-6-carboxylate (2f)

The title compound was prepared by the above general procedure A. Yield: 48%; Mp 313-316° C.; IR (neat): 3252, 3148, 3082, 2986, 2906, 1715, 1638, 1557, 1505, 1496, 1487, 1443, 1262, 1231, 1174, 1128, 1028, 965, 898, 839, 804, 789, 772, 755, 705, 667 cm$^{-1}$; $^1$H NMR (600 MHz, DMSO-d6) δ 11.76 (s, 1H), 10.11 (s, 1H), 8.69 (s, 1H), 8.14 (dd, J=9.0 Hz, J=1.8 Hz, 1H), 7.83 (d, J=8.6 Hz, 1H), 7.71 (d, J=8.7 Hz, 2H), 6.95 (d, J=8.9 Hz, 2H), 6.34 (s, 1H), 4.35 (q, J=7.0 Hz, 2H), 1.36 (t, J=7.1 Hz, 3H); $^{13}$C NMR (150 MHz, DMSO-d6) δ 176.6, 165.3, 159.9, 150.7, 143.4, 131.4, 129.0, 127.0, 124.1, 124.0, 119.1, 115.8, 107.0, 60.8, 14.2. ESI-HRMS (m/z): Calcd for $C_{18}H_{14}NO_4$ [(M)-] 308.0923. found [(M)-] 308.0930.

Ethyl 2-(3-methoxyphenyl)-4-oxo-1,4-dihydroquinoline-6-carboxylate

The title compound was prepared by the above general procedure A. Yield: 85%; Mp 277-280° C.; IR (neat): 3140, 3077, 2968, 1713, 1643, 1550, 1504, 1265, 1235, 1128, 1032, 882, 840, 771, 754, 706, 669 cm$^{-1}$; $^1$H NMR (600 MHz, DMSO-d$_6$) δ 11.93 (s, 1H), 8.71 (s, 1H), 8.18 (dd, J=9.0 Hz, J=1.5 Hz, 1H), 7.85 (d, J=8.5 Hz, 1H), 7.51 (t, J=8.2 Hz, 1H), 7.43-7.38 (m, 2H), 7.17 (d, J=8.5 Hz, 1H), 6.45 (s, 1H), 4.36 (q, J=7.1 Hz, 2H), 3.87 (s, 3H), 1.36 (t, J=7.2 Hz, 3H); $^{13}$C NMR (150 MHz, DMSO-d$_6$) δ 177.3, 165.8, 160.0, 151.0, 143.8, 135.6, 132.1, 130.7, 127.5, 124.8, 124.6, 120.2, 119.8, 116.9, 113.4, 108.9, 61.3, 55.9, 14.7. ESI-HRMS (m/z): Calcd for $C_{19}H_{16}NO_4$ [(M)-] 322.1079. found [(M)-] 322.1085.

Ethyl 2-(3-fluorophenyl)-4-oxo-1,4-dihydroquinoline-6-carboxylate (2h)

The title compound was prepared by the above general procedure A. Yield: 88%; Mp 307-310° C.; IR (neat): 3247, 3143, 3079, 2981, 2901, 1715, 1639, 1583, 1505, 1486, 1444, 1264, 1233, 1174, 1130, 1026, 901, 840, 790, 773, 756, 706 cm$^{-1}$; $^1$H NMR (600 MHz, DMSO-d$_6$) δ 11.98 (s, 1H), 8.71 (s, 1H), 8.19 (dd, J=9.1 Hz, J=2.4 Hz, 1H), 7.85 (d, J=8.7 Hz, 1H), 7.79-7.70 (m, 2H), 7.68-7.63 (m, 1H), 7.45 (t, J=8.7 Hz, 1H), 6.48 (s, 1H), 4.37 (q, J=7.1 Hz, 2H), 1.37 (t, J=7.2 Hz, 3H); $^{13}$C NMR (150 MHz, DMSO-d$_6$) δ 177.3, 165.7, 163.5, 161.9, 149.7, 143.8, 136.5, 132.2, 131.7, 131.6, 127.5, 125.0, 124.6, 124.2, 119.9, 118.0, 117.9, 115.1, 114.9, 109.2, 61.3, 14.7. ESI-HRMS (m/z): Calcd for $C_{18}H_{13}NO_3F$ [(M)-] 310.0879. found [(M)-] 322.0873.

Ethyl 4-oxo-2-(3-(trifluoromethyl)phenyl)-1,4-dihydroquinoline Carboxylate (2i)

The title compound was prepared by the above general procedure A. Yield: 82%; Mp 320-325° C.; IR (neat): 3255, 3140, 3082, 2984, 2906, 1715, 1637, 1582, 1505, 1486, 1443, 1262, 1174, 1128, 1111, 1025, 840, 804, 789, 772, 755, 705, 668 cm$^{-1}$; $^1$H NMR (600 MHz, DMSO-d$_6$) δ 12.08 (s, 1H), 8.72 (s, 1H), 8.24-8.15 (m, 3H), 7.97 (d, J=8.0 Hz, 1H), 7.84 (t, J=8.2 Hz, 2H), 6.52 (s, 1H), 4.37 (q, J=7.1 Hz, 2H), 1.37=8 (t, J=7.1 Hz, 3H); $^{13}$C NMR (150 MHz, DMSO-d$_6$) δ 177.3, 165.7, 149.6, 143.9, 135.3, 132.3, 130.7, 130.5, 130.3, 130.1, 129.9, 127.7, 127.5, 125.3, 125.0, 124.7, 123.5, 119.9, 109.6, 61.3, 14.7. ESI-HRMS (m/z): Calcd for $C_{19}H_{13}NO_3F_3$ [(M)-] 360.0848. found [(M)-] 360.0842.

Ethyl 2-(3-hydroxyphenyl)-4-oxo-1,4-dihydroquinoline-6-carboxylate (2j)

The title compound was prepared by the above general procedure A. Yield: 27%; Mp 268-309° C.; IR (neat): 3204, 1724, 1583, 1500, 1488, 1272, 1135, 833, 759, 711, 683 cm$^{-1}$; $^1$H NMR (600 MHz, DMSO-d$_6$) δ 11.92 (s, 1H), 9.88 (s, 1H), 8.70 (s, 1H), 8.17 (dd, J=1.4, 8.7 Hz, 1H), 7.84 (d, J=8.7 Hz, 1H), 7.39 (t, J=7.9 Hz, 1H), 7.24 (d, J=7.5 Hz, 1H), 7.18 (s, 1H), 6.99 (d, J=7.6 Hz, 1H), 6.33 (s, 1H), 4.36 (q, J=7.1 Hz, 2H), 1.36 (t, J=7.1 Hz, 3H); $^{13}$C NMR (125 MHz, DMSO-d$_6$) δ 177.3, 165.8, 158.2, 151.3, 143.8, 135.6, 132.0, 130.7, 127.5, 124.8, 124.6, 119.8, 118.6, 118.1, 114.6, 108.6, 61.3, 14.7; ESI-HRMS (m/z): calc. for C$_{18}$H$_{15}$NO$_4$ [M+H]$^+$ 310.1079. found for 310.1079.

Methyl 4-oxo-2-phenyl-1,4-dihydroquinoline-6-carboxylate (2k)

The title compound was prepared by the above general procedure A. Yield: 82%; Mp 357-360° C.; IR (neat): 3252, 3143, 3082, 2978, 1704, 1636, 1578, 1489, 1437, 1395, 1279, 1257, 1236, 1119, 973, 840, 768, 697, 683, 669 cm$^{-1}$; $^1$H NMR (600 MHz, DMSO-d$_6$) δ 11.98 (s, 1H), 8.73 (s, 1H), 8.18 (d, J=8.9 Hz, 1H), 7.89-7.83 (m, 3H), 7.64-7.59 (m, 3H), 6.42 (s, 1H), 3.91 (s, 3H); $^{13}$C NMR (150 MHz, DMSO-d$_6$) δ 177.3, 166.3, 151.3, 143.9, 134.3, 132.0, 131.2, 129.5, 128.0, 127.7, 124.7, 124.6, 119.9, 108.9, 52.7. EI-HRMS (m/z): Calcd for C$_{17}$H$_{13}$NO$_3$ [(M)-] 279.0895. found [(M)-] 279.0900.

Isopropyl 4-oxo-2-phenyl-1,4-dihydroquinoline-6-carboxylate (2l)

The title compound was prepared by the above general procedure A. Yield: 73%; Mp 291-294° C.; IR (neat): 3260, 3146, 3085, 2973, 1713, 1644, 1580, 1549, 1497, 1266, 1128, 838, 750, 690, 683 cm$^{-1}$; $^1$H NMR (600 MHz, DMSO-d$_6$) δ 11.97 (s, 1H), 8.70 (s, 1H), 8.18 (dd, J=8.5 Hz, J=1.8 Hz, 1H), 7.88-7.84 (m, 3H), 7.63-7.59 (m, 3H), 6.43 (s, 1H), 5.19 (sept, J=6.2 Hz, 1H), 1.37 (d, J=6.2 Hz, 6H); $^{13}$C NMR (150 MHz, DMSO-d$_6$) δ 177.3, 165.3, 151.2, 143.9, 134.3, 132.1, 131.2, 129.5, 128.0, 127.5, 125.2, 124.6, 119.8, 108.8, 68.7, 22.2. EI-HRMS (m/z): Calcd for C$_{19}$H$_{17}$NO$_3$ [(M)-] 307.1208. found [(M)-] 307.1206.

Methyl 2-(3-fluorophenyl)-4-oxo-1,4-dihydroquinoline-6-carboxylate (RJ-LC-15-22)

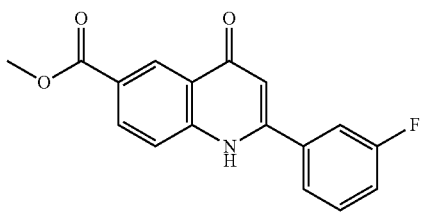 [SMILES: COC(=O)c1ccc2[nH]c(-c3cccc(F)c3)cc(=O)c2c1]

The title compound was prepared by the above general procedure A. Yield: 71%; Mp 370° C.; $^1$H NMR (500 MHz, DMSO-d$_6$) δ 11.98 (s, 1H), 8.71 (d, J=1.8 Hz, 1H), 8.19 (dd, J=8.6 Hz, J=1.9 Hz, 1H), 7.84 (d, J=8.8 Hz, 1H), 7.78-7.70 (m, 2H), 7.67-7.62 (m, 1H), 7.48-7.42 (m, 1H), 6.47 (s, 1H), 3.90 (s, 3H); $^{13}$C NMR (125 MHz, DMSO-d$_6$) δ 177.3, 166.2, 163.7, 161.7, 149.7, 143.9, 136.5, 132.1, 131.7, 131.6, 127.6, 124.7, 124.2, 119.9, 118.1, 117.9, 115.1, 114.9, 109.2, 52.7; $^{19}$F NMR (470 MHz, DMSO-d$_6$) δ -111.9; FAB-HRMS (m/z): Calcd for C$_{17}$H$_{13}$NO$_3$F [M+H]$^+$ 298.0879. found [M+H]$^+$ 298.0871.

Isopropyl 2-(3-fluorophenyl)-4-oxo-1,4-dihydroquinoline-6-carboxylate (RJ-LC-15-23)

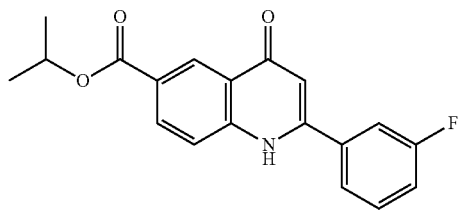 [SMILES: CC(C)OC(=O)c1ccc2[nH]c(-c3cccc(F)c3)cc(=O)c2c1]

The title compound was prepared by the above general procedure A. Yield: 68%; Mp 310° C.; $^1$H NMR (500 MHz, CDCl$_3$/CD$_3$OD) δ 8.95 (d, J=1.9 Hz, 1H), 8.21 (dd, J=8.7 Hz, J=2.3 Hz, 1H), 7.68 (d, J=8.8 Hz, 1H), 7.55-7.44 (m, 3H), 7.25-7.20 (m, 1H), 6.54 (s, 1H), 5.29-5.20 (m, 1H), 1.37 (d, J=6.3 Hz, 6H); $^{13}$C NMR (125 MHz, CDCl$_3$/CD$_3$OD) δ 179.7, 166.2, 164.2, 162.2, 151.0, 143.5, 136.3, 136.3, 132.8, 131.2, 131.2, 128.3, 126.6, 124.5, 123.5, 123.5, 118.9, 118.1, 117.9, 114.8, 114.6, 109.3, 69.4, 22.0; $^{19}$F NMR (470 MHz, CDCl$_3$/CD$_3$OD) δ -111.7; FAB-HRMS (m/z): Calcd for C$_{19}$H$_{17}$NO$_3$F [M+H]$^+$ 326.1192. found [M+H]$^+$ 326.1196.

Phenyl 2-(3-fluorophenyl)-4-oxo-1,4-dihydroquinoline-6-carboxylate (RJ-LC-15-24)

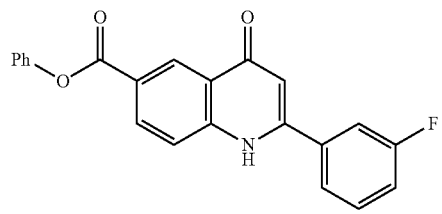 [SMILES: O=C(Oc1ccccc1)c1ccc2[nH]c(-c3cccc(F)c3)cc(=O)c2c1]

The title compound was prepared by the above general procedure A. Yield: 65%; Mp 322° C.; $^1$H NMR (500 MHz, DMSO-d$_6$) δ 12.06 (s, 1H), 8.88 (d, J=1.2 Hz, 1H), 8.33 (dd, J=8.9 Hz, J=2.1 Hz, 1H), 7.92 (d, J=8.8 Hz, 1H), 7.81-7.73 (m, 2H), 7.69-7.63 (m, 1H), 7.53-7.43 (m, 3H), 7.36-7.31 (m, 3H), 6.53 (s, 1H); $^{13}$C NMR (125 MHz, DMSO-d$_6$) δ 176.8, 164.1, 163.2, 161.2, 150.7, 149.4, 143.9, 136.0, 132.1, 131.2, 131.2, 129.6, 128.0, 126.0, 124.2, 123.8, 123.8, 123.5, 122.0, 119.8, 117.6, 117.5, 114.7, 114.5, 108.9; $^{19}$F NMR (470 MHz, CDCl$_3$/CD$_3$OD) δ -111.8; FAB-HRMS (m/z): Calcd for C$_{22}$H$_{15}$NO$_3$F [M+H]$^+$ 360.1036. found [M+H]$^+$ 360.1031.

Ethyl 2-(3-bromophenyl)-4-oxo-1,4-dihydroquinoline-6-carboxylate (RJ-LC-15-25)

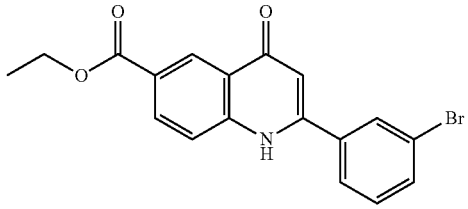 [SMILES: CCOC(=O)c1ccc2[nH]c(-c3cccc(Br)c3)cc(=O)c2c1]

The title compound was prepared by the above general procedure A. Yield: 88%; Mp 325° C.; $^1$H NMR (500 MHz, DMSO-$d_6$) δ 12.00 (s, 1H), 8.70 (d, J=2.1 Hz, 1H), 8.18 (dd, J=8.9 Hz, J=2.1 Hz, 1H), 8.07 (s, 1H), 7.88-7.78 (m, 3H), 7.54 (t, J=7.9 Hz, 1H), 6.45 (s, 1H), 4.36 (q, J=6.9 Hz, 2H), 1.36 (t, J=7.2 Hz, 3H); $^{13}$C NMR (125 MHz, DMSO-$d_6$) δ 176.8, 165.2, 149.1, 143.4, 136.1, 133.4, 131.6, 131.1, 130.0, 127.0, 126.8, 124.5, 124.1, 122.2, 119.4, 108.8, 60.9, 14.2; FAB-HRMS (m/z): Calcd for $C_{18}H_{15}NO_3Br$ [M+H]$^+$ 372.0235. found [M+H]$^+$ 372.0232.

2-(2-(2-(2-hydroxyethoxy)ethoxy)ethoxy)ethyl 4-oxo-2-phenyl-1,4-dihydro quinoline-6-carboxylate (RJ-LC-15-3)

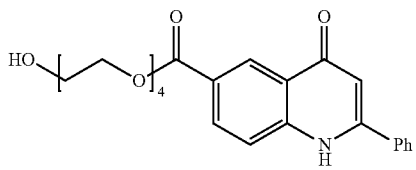

To a dry and N$_2$-flushed 10 mL Schlenk flask equipped with stir bar and septum was added SM (10 mg, 1 eq.) and CDI (6.4 mg, 1.05 eq.) in dry DMF (0.05 M, 0.8 mL) and stirred at rt. for 4 h. Added K$_2$CO$_3$ (7.8 μL, 1.5 eq.) and TEG (9.8 μL, 1.5 eq.), the reaction mixture was stirred at rt. for overnight. After completion of the reaction, the DMF was removed in vacuo and the crude solid was purified by column chromatography to give solid product (10 mg, 60%). $^1$H NMR (400 MHz, CDCl$_3$) δ 8.90 (s, 1H), 8.10 (d, J=7.1 Hz 1H), 7.82-7.60 (m, 3H), 7.39 (br, 3H), 6.36 (s, 1H), 4.43 (t, J=4.5 Hz, 2H), 3.79 (t, J=4.6 Hz, 2H), 3.73-3.59 (m, 10H), 3.55 (t, J=4.6 Hz, 2H); $^{13}$C NMR (100 MHz, CDCl$_3$) 178.7, 165.9, 151.3, 143.2, 133.9, 132.4, 130.7, 129.1, 128.4, 127.2, 125.2, 124.3, 118.8, 109.1, 72.5, 70.7, 70.6, 70.5, 70.3, 69.2, 64.3.

4-oxo-2-phenyl-1,4-dihydroquinoline-6-carboxylic Acid (2a)

To a test tube equipped with a stir bar and septum was added AS1712 (50 mg, 0.17 mmol), 1:9 EtOH/H$_2$O (1.9 ml) and NaOH (70 mg, 1.71 mmol). The resulting mixture was stirred at 40° C. for 4 h. After removal of EtOH in vacuo, the mixture was acidified with 10% HCl and collected the white precipitate. Yield: 99%. Mp 285-290° C.; $^1$H NMR (400 MHz, DMSO-$d_6$) δ 12.06 (s, 1H), 8.70 (s, 1H), 8.16 (d, J=8.7 Hz, 1H), 7.91-7.84 (m, 3H), 7.62-7.58 (m, 3H), 6.40 (s, 1H); $^{13}$C NMR (100 MHz, DMSO-$d_6$) δ 177.4, 167.3, 151.1, 143.7, 134.3, 132.3, 131.1, 129.5, 128.0, 127.7, 125.8, 124.6, 119.6, 108.7.

Sodium 4-oxo-2-phenyl-1,4-dihydroquinoline-6-carboxylate (RJ-LC-15-21)

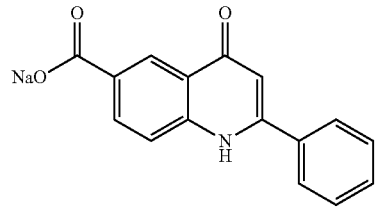

To a test tube equipped with a stir bar and septum was added 2a (20 mg, 0.075 mmol), 1:1 EtOH/H$_2$O (0.5 ml) and NaOH (3 mg, 0.075 mmol). The resulting mixture was stirred at rt for 10 min. Removal solvent in vacuo to get product. Yield: 93%; IR (neat): 3152, 1604, 1577, 1545, 1492, 1403, 765 cm$^{-1}$; $^1$H NMR (400 MHz, CD$_3$OD) 8.93 (d, J=1.8 Hz, 1H), 8.27 (dd, J=8.6 Hz, J=2.0 Hz, 1H), 7.83-7.78 (m, 2H), 7.71 (d, J=8.7 Hz, 1H), 7.60-7.55 (m, 3H), 6.54 (s, 1H); $^{13}$C NMR (150 MHz, CD$_3$OD) δ179.6, 172.8, 152.1, 141.8, 134.1, 133.9, 133.0, 130.5, 128.9, 127.1, 126.2, 123.8, 117.5, 107.4; HRMS (ESI) (m/z): calculated for $C_{16}H_{11}NO_3Na_2$ [M+Na]+310.0450. found for 310.0451.

2-(3-fluorophenyl)-4-oxo-1,4-dihydroquinoline-6-carboxylic Acid (RJ-LC-15-26)

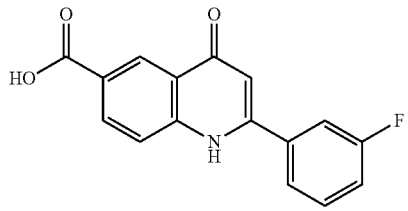 [SMILES: O=C(O)c1ccc2[nH]c(-c3cccc(F)c3)cc(=O)c2c1]

To a test tube equipped with a stir bar and septum was added RJ-LC-15-8 (200 mg, 0.64 mmol), 1:9 EtOH/H$_2$O (7.1 ml) and NaOH (256 mg, 0.64 mmol). The resulting mixture was stirred at 40° C. for 4 h. After removal of EtOH in vacuo, the mixture was acidified with 10% HCl and collected the white precipitate. Yield: 99%. Mp>400° C.; $^1$H NMR (500 MHz, DMSO-$d_6$) δ 12.15 (s, 1H), 12.04 (s, 1H), 8.70 (d, J=2.1 Hz, 1H), 8.17 (dd, J=8.7 Hz, J=2.0 Hz, 1H), 7.89 (d, J=8.8 Hz, 1H), 7.80-7.71 (m, 2H), 7.67-7.62 (m, 1H), 7.48-7.42 (m, 1H), 6.51 (s, 1H); $^{13}$C NMR (125 MHz, DMSO-$d_6$) δ 176.6, 166.8, 163.2, 161.2, 149.4, 143.3, 136.1, 131.9, 131.2, 131.1, 127.1, 125.6, 123.9, 123.8, 123.8, 119.4, 117.6, 117.4, 114.7, 114.5, 108.4; $^{19}$F NMR (470 MHz, DMSO-$d_6$) δ -111.9; FAB-HRMS (m/z): Calcd for $C_{16}H_{11}NO_3F$ [M+H]$^+$ 284.0723. found [M+H]$^+$ 284.0722.

2-ethylbutyl 2-(3-fluorophenyl)-4-oxo-1,4-dihydro-quinoline-6-carboxylate

N-ethyl-2-(3-fluorophenyl)-4-oxo-1,4-dihydroquinoline-6-carboxamide (RJ-LC-15-27)

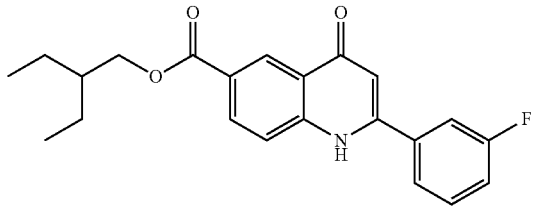 [SMILES: CCC(CC)COC(=O)c1ccc2[nH]c(-c3cccc(F)c3)cc(=O)c2c1]

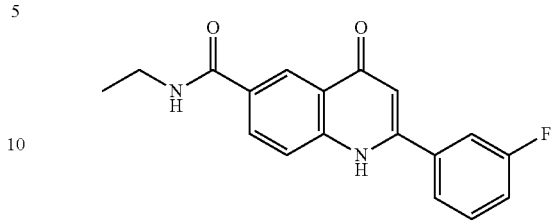

To a dry and $N_2$-flushed 10 mL Schlenk flask equipped with stir bar and septum was added RJ-LC-15-26 (50 mg, 0.18 mmol) and CDI (30 mg, 0.19 mmol) in anhydrous DMF (5 ml). The reaction mixture was stirred at room temperature for 1.5 h, then treated with $K_2CO_3$ (26 mg, 0.19 mmol), 2-ethylbutanol (19 mg, 0.19 mmol) and stirred for overnight. After completion of the reaction, the DMF was removed in vacuo and purified by column chromatography to give solid product. $^1$H NMR (500 MHz, $CDCl_3/CD_3OD$) δ 8.95 (d, J=2.1 Hz, 1H), 8.24 (dd, J=8.9 Hz, J=1.9 Hz, 1H), 7.75 (d, J=8.6 Hz, 1H), 7.59-7.49 (m, 3H), 7.30-7.25 (m, 1H), 6.56 (s, 1H), 4.29 (d, J=5.8 Hz, 2H), 1.74-1.65 (m, 1H), 1.54-1.44 (m, 4H), 0.96 (t, J=7.4 Hz, 6H); $^{13}$C NMR (125 MHz, $CDCl_3/CD_3OD$) δ 180.1, 167.1, 164.7, 162.7, 151.8, 144.1, 136.7, 136.7, 133.2, 131.7, 131.7, 128.6, 126.7, 124.9, 124.0, 123.9, 119.6, 118.5, 118.3, 115.2, 115.0, 109.6, 68.0, 41.3, 24.0, 11.3; $^{19}$F NMR (470 MHz, $CDCl_3/CD_3OD$) δ −112.3.

N-ethyl-4-oxo-2-phenyl-1,4-dihydroquinoline-6-carboxamide (2b)

To a dry and $N_2$-flushed 10 mL Schlenk flask equipped with stir bar and septum was added RJ-LC-15-01 (10 mg, 0.038 mmol) and CDI (6.4 mg, 0.04 mmol) in anhydrous DMF (0.8 ml). The reaction mixture was stirred at room temperature for 4 h, then treated with TEA (7.9 μL, 0.057 mmol), ethylamine hydrochloride (4.6 mg, 0.057 mmol) and stirred for overnight. After completion of the reaction, the DMF was removed in vacuo and purified by column chromatography to give solid product. Yield: 64%. Mp 330-340° C.; IR (neat): 3561, 3271, 3070, 2969, 1629, 1577, 1494, 1295, 1253, 1149, 1081, 1048, 969, 914, 836, 803, 765, 692, 681 cm$^{-1}$; $^1$H NMR (600 MHz, $CD_3OD/CDCl_3$) δ 8.59 (s, 1H), 8.15 (d, J=8.8 Hz 1H), 7.76-7.71 (m, 3H), 7.56-7.52 (m, 3H), 6.59 (s, 1H), 3.46 (q, J=7.4 Hz, 2H), 1.26 (t, J=7.4 Hz, 3H); $^{13}$C NMR (150 MHz, $CD_3OD/CDCl_3$) δ 179.4, 167.5, 152.4, 142.3, 133.9, 131.6, 130.9, 130.1, 129.1, 127.3, 123.9, 123.5, 118.9, 108.6, 35.0, 14.3. ESI-HRMS (m/z): Calcd for $C_{18}H_{17}N_2O_2$ [(M)−] 293.1290. found [(M)−] 293.1287.

To a dry and $N_2$-flushed 10 mL Schlenk flask equipped with stir bar and septum was added RJ-LC-15-26 (50 mg, 0.18 mmol) and CDI (30 mg, 0.18 mmol) in anhydrous DMF (3.5 ml). The reaction mixture was stirred at room temperature for 4 h, then treated with TEA (26 μL, 0.18 mmol), ethylamine hydrochloride (15 mg, 0.18 mmol) and stirred for overnight. After completion of the reaction, the DMF was removed in vacuo and purified by column chromatography to give solid product. Yield: 82%. Mp 358° C.; $^1$H NMR (500 MHz, DMSO-$d_6$) δ 11.87 (s, 1H), 8.70 (t, J=5.5 Hz, 1H), 8.64 (d, J=2.0 Hz, 1H), 8.13 (dd, J=8.7 Hz, J=2.1 Hz, 1H), 7.81-7.70 (m, 3H), 7.67-7.61 (m, 1H), 7.47-7.41 (m, 1H), 6.45 (s, 1H), 3.32 (m, 2H), 1.14 (t, J=7.4 Hz, 3H); $^{13}$C NMR (125 MHz, DMSO-$d_6$) δ 177.1, 165.2, 163.2, 161.2, 148.9, 142.0, 136.2, 131.2, 131.1, 130.7, 129.5, 124.0, 123.7, 118.8, 117.4, 117.3, 114.6, 114.4, 108.3, 34.1, 14.8; $^{19}$F NMR (470 MHz, DMSO-$d_6$) δ −112.0; FAB-HRMS (m/z): Calcd for $C_{18}H_{16}N_2O_2F$ [M+H]$^+$ 311.1196. found [M+H]$^+$ 311.1187.

6-(ethoxymethyl)-2-phenylquinolin-4(1H)-one (2m)

To a flask equipped with a stir bar and septum was added AS1712 (100 mg, 0.341 mmol) in anhydrous THF (0.7 ml), then dropwise DIBAL-H (0.85 ml, 1.2M in toluene) under ice bath and $N_2$ atmosphere. After stirred at 0° C. for 1 h, the solution was quenched with MeOH and evaporated to get crude. The crude was purified by flash column chromatography (MeOH/DCM) to afford primary alcohol. Next, the primary alcohol (80 mg, 0.318 mmol) was suspended on anhydrous $Et_2O$ (1.1 ml) and slowly treated with $PBr_3$ (30 μL, 0.318 mmol) on $N_2$ atmosphere. After refluxed 2h, the mixture was quenched with $H_2O$ and collected solid product by filtration. Finally, the benzylbromide (100 mg, 0.318 mmol) was suspended on EtOH (10.6 ml) and treated with DIPEA (498 μL, 2.86 mmol). After stirred at room temperature for overnight, the clear solution was evaporated the solvent and purified by flash column chromatography (MeOH/DCM) to afford RJ-LC-15-16. Yield: 46%; Mp 218-222° C.; IR (neat): 3059, 2966, 2925, 2853, 1649, 1594, 1577, 1543, 1500, 1252, 1097, 1084, 800, 773, 696, 684, 664, 560, 516 cm$^{-1}$; $^1$H NMR (600 MHz, $CDCl_3$) δ 10.08 (s, 1H), 8.24 (s, 1H), 7.69-7.64 (m, 4H), 7.46-7.43 (m, 3H), 6.43 (s, 1H), 4.57 (s, 2H), 3.54 (q, J=7.2 Hz, 2H), 1.23 (t, J=7.1 Hz, 3H); $^{13}$C NMR (150 MHz, $CDCl_3$) δ 178.9, 150.8, 140.1, 134.4, 132.0, 130.4, 129.0, 127.2, 124.9, 124.4, 118.9, 108.2, 72.3, 65.8, 15.2. EI-HRMS (m/z): Calcd for $C_{18}H_{17}NO_2$ [(M)−] 279.1259. found [(M)−] 279.1253.

Ethyl 3-oxo-3-(3-(pent-4-yn-1-yloxy)phenyl)propanoate (3)

The mixture of ethyl 3-(3-hydroxyphenyl)-3-oxopropanoate (30 mg, 0.144 mmol) and $Cs_2CO_3$ (47 mg, 0.144 mmol)

in acetonitrile (1 mL) was added a solution of pent-4-yn-1-yl 4-methylbenzenesulfonate (35 mg, 0.144 mmol) in acetonitrile at room temperature and heated to 50° C. for 26 h. The reaction mixture was cooled down, filtered through cotton, evaporated solvent, and extracted with EA. Combined organic layers were dried over $Na_2SO_4$ then filtered and concentrated under vacuo to obtain the crude, which then purified by column chromatography (50% $CH_2Cl_2$/n-Hexane) to afford ethyl 3-oxo-3-(3-(pent-4-yn-1-yloxy)phenyl) propanoate as a colorless liquid with keto-enol tautomers. Yield: 48%. $^1$H NMR (600 MHz, $CDCl_3$) δ 12.56 (s, 0.2H, enol form), 7.49 (m, 2H), 7.37 (t, J=7.9 Hz, 1H), 7.13 (dd, J=2.2, 8.2 Hz, 1H), 5.65 (s, 0.2H, enol form), 4.26 (q, J=7.0 Hz, 0.4H, enol form), 4.21 (q, J=7.2 Hz, 2H), 4.12 (t, J=6.0 Hz, 2.4H, keto+enol), 3.97 (s, 2H), 2.41 (td, J=2.4, 7.0 Hz, 2.4H, keto+enol), 2.02 (quin, J=6.5 Hz, 2.6H, keto+enol), 1.98 (t, J=2.5 Hz, 1H), 1.33 (t, J=7.1 Hz, 0.6H), 1.26 (t, J=7.1 Hz, 3H); $^{13}$C NMR (150 MHz, $CDCl_3$) δ 192.3, 173.2 (enol form), 171.3 (enol form), 167.5, 159.3, 159.0 (enol form), 137.4, 134.9 (enol form), 129.8, 129.6 (enol form), 121.2, 120.7, 118.5 (enol form), 117.8 (enol form), 113.3, 111.9 (enol form), 87.6 (enol form), 83.4 (enol form), 83.2, 69.1, 69.0 (enol form), 66.4, 66.3 (enol form), 61.5, 60.3 (enol form), 46.1, 28.1 (enol form), 28.0, 15.1, 14.3 (enol form), 14.1; HRMS (ESI+) calc. for $C_{16}H_{18}O_4$ [M+H]$^+$ 275.1283. found for 275.1283.

Ethyl 2-(3-(but-3-yn-1-yloxy)phenyl)-4-oxo-1,4-dihydroquinoline-6-carboxylate (4)

The title compound was prepared by the above general procedure A. Yield: 53%; Mp 223-229° C.; IR (neat): 3300, 3145, 3085, 2987, 1711, 1646, 1581, 1506, 1491, 1266, 1236, 1126, 1042, 841, 792, 758, 711 cm$^{-1}$; $^1$H NMR (600 MHz, DMSO-$d_6$) δ 11.93 (s, 1H), 8.72 (d, J=1.8 Hz, 1H), 8.19 (dd, J=1.8, 8.7 Hz, 1H), 7.86 (d, J=8.7 Hz, 1H), 7.51 (t, J=7.9 Hz, 1H), 7.42 (d, J=8.6 Hz, 2H), 7.18 (dd, J=1.9, 7.8 Hz, 1H), 6.45 (s, 1H), 4.37 (q, J=7.0 Hz, 2H), 4.17 (t, J=6.2 Hz, 2H), 2.84 (t, J=2.5 Hz, 1H), 2.38 (td, J=2.5, 7.2 Hz, 2H), 1.95 (quin, J=6.6 Hz, 2H), 1.38 (t, J=7.1 Hz, 3H); $^{13}$C NMR (125 MHz, DMSO-$d_6$) δ 177.1, 165.8, 159.2, 151.2, 144.1, 135.9, 131.9, 130.7, 127.5, 124.7, 124.6, 120.2, 117.1, 113.9, 108.8, 84.1, 72.2, 66.7, 61.3, 28.2, 15.0, 14.7; ESI-HRMS (m/z): calc. for $C_{23}H_{21}NO_4$ [M−H]$^-$ 374.1392. found for 374.1390.

1,1,1,2,2,3,3,4,4,5,5,6,6-tridecafluoro-8-(pent-4-yn-1-yloxy)octane

The perfluoro-1-octanol (48 μL, 0.218 mmol), pent-4-yn-1-yl 4-methylbenzenesulfonate (52 mg, 0.218 mmol), KOH (600 mg, 10.7 mmol) and TBAI (10 mg, 0.03 mmol) were dissolved in 9:1 THF/$H_2O$ (1 ml), then refluxed for overnight. After removal of THF in vacuo, the solution was extracted with DCM and purified by column chromatography to give liquid product (50 mg, 53%). $^1$H NMR (600 MHz, $CDCl_3$) δ 3.72 (t, J=6.9 Hz, 2H), 3.55 (t, J=6.2 Hz, 2H), 2.45-2.34 (m, 2H), 2.31-2.26 (m, 2H), 1.94 (t, J=2.6 Hz, 1H), 1.78 (quint, J=6.7 Hz, 2H), 3.54 (q, J=7.2 Hz, 2H), 1.23 (t, J=7.1 Hz, 3H); $^{13}$C NMR (150 MHz, $CDCl_3$) δ 83.6, 69.4, 68.5, 62.7, 31.7, 31.5, 31.4, 28.4, 15.1; $^{19}$F NMR (564 MHz, $CDCl_3$) δ −127.2, −124.7, −123.9, −122.9, −114.4, −81.9.

Azido-PEG12-MBs

Carboxylated magnetic beads (10 mg) were dispersed into MES (50 mM, pH 6.0, 300 μL). N-hydroxysuccinimide (NHS, 3.5 mg, 0.03 mmol) and 1-ethyl-3-(3-dimethylaminopropyl)carbodiimide hydrochloride (EDC·HCl, 5.7 mg, 0.03 mmol) were added to the solution and stirred for 1.5 h at room temperature. The resulting beads were washed with PBS (50 mM, pH 7.0, 300 μL×2) to remove excess NHS and EDC·HCl. 200 μL of 1 mM carboxylated-PEG$_{12}$-amine (pH 7.8 in 50 mM HEPES) was added to the beads and then stirred for 6 hr at room temperature. After separation with a magnet, the beads were washed with MES (50 mM, pH 6.0) to give carboxyl-PEG$_{12}$-MBs. Carboxyl-PEG$_{12}$-MBs (10 mg) were dispersed into IVIES (50 mM, pH 6.0, 300 μL). N-hydroxysuccinimide (NHS, 3.5 mg, 0.03 mmol) and 1-ethyl-3-(3 dimethylaminopropyl)carbodiimide hydrochloride (EDC·HCl, 5.7 mg, 0.03 mmol) were added to the solution and stirred for 1.5 h at room temperature. The resulting beads were washed with PBS (50 mM, pH 7.0, 300 μL×2) to remove excess NHS and EDC·HCl. 200 μL of 1 mM 3-azidopropan-1-amine (pH 7.0 in 50 mM PBS) was added to the beads and then stirred for 16 hr at room temperature. After separation with a magnet, the beads were washed with MES (50 mM, pH 6.0) to give Azido-PEG$_{12}$-MBs.

Mag-Beads-Control

To a solution of Azido-PEG$_{12}$-MBs (10 mg), 1,1,1,2,2,3,3,4,4,5,5,6,6-tridecafluoro-8-(pent-4-yn-1-yloxy)octane (1.72 mg, 4.0 μmol), $CuSO_4$ in 0.1 M dd-$H_2O$ (6.6 μL) and sodium ascorbate in 0.1 M dd-$H_2O$ (1.3 μL) was in t-Butanol/dd-H2O (0.3 mL, 1/1, v/v) and in Microwave condition: 100 W, 60° C. for 30 min. After separation with a magnet, the beads were washed with MES (50 mM, pH 6.0) to give Mag-beads-control.

Mag-Beads-AS1712

To a solution of Azido-PEG$_{12}$-MBs (10 mg), RJ-LC-15-12 (1.5 mg, 4.0 μmol), $CuSO_4$ in 0.1 M dd-$H_2O$ (6.6 μL) and sodium ascorbate in 0.1 M dd-$H_2O$ (1.3 μL) was in t-Butanol/dd-$H_2O$ (0.3 mL, 1/1, v/v) and in Microwave condition: 100 W, 60° C. for 30 min. After separation with a magnet, the beads were washed with MES (50 mM, pH 6.0) to give Mag-beads-AS1712.

General Procedure B for Synthesis of RJ-LC-15-17 and RJ-LC-15-18

A solution of ethyl 3-aminobenzoate (0.605 mmol), benzoylacetate (0.96 mmol), TsOH·$H_2O$ (0.15 mmol) and $Na_2SO_4$ (6.16 mmol) in DCM (3.3 ml) was stirred and refluxed for 72 h. The reaction mixture was concentrated in vacuo and washed with hexane. Next, filtrate was filtrate and evaporated to get imine. The imine was dissolved in diphenylether (1 ml) and heated to 250° C. for 10 mins. The reaction mixture was cooled to room temperature. After trituration with $Et_2O$, the product was collected by filtration, and purified by flash chromatography (DCM/ACN/MeOH) to isolate RJ-LC-15-17 and RJ-LC-15-18.

Ethyl 4-oxo-2-phenyl-1,4-dihydroquinoline-5-carboxylate (RJ-LC-15-17)

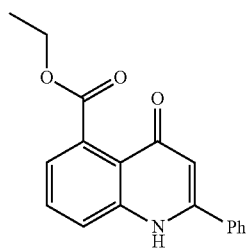 [SMILES: CCOC(=O)c1cccc2[nH]c(-c3ccccc3)cc(=O)c12]

The title compound was prepared by the above general procedure B. Yield: 16%; Mp 220° C.; IR (neat): 3067, 2396, 1718, 1627, 1577, 1507, 1500, 1277, 1147, 1124, 1089, 1028, 1028, 765, 697 cm$^{-1}$; $^1$H NMR (600 MHz, CD$_3$OD/CDCl$_3$) δ 7.75-7.55 (m, 4H), 7.50-7.42 (m, 3H), 7.20 (d, J=7.4 Hz, 3H), 6.42 (s, 1H), 4.42 (q, J=7.1 Hz, 2H), 1.37 (t, J=7.2 Hz, 3H); $^{13}$C NMR (150 MHz, CD$_3$OD/CDCl$_3$) δ 177.8, 171.5, 151.5, 140.8, 133.9, 133.2, 131.4, 130.6, 129.0, 127.2, 122.2, 121.5, 119.7, 108.2, 61.9, 13.7.

Ethyl 4-oxo-2-phenyl-1,4-dihydroquinoline-7-carboxylate (RJ-LC-15-18)

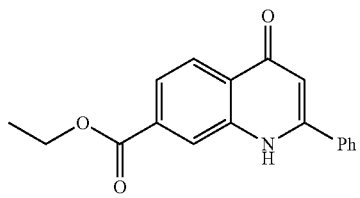 [SMILES: CCOC(=O)c1ccc2c(=O)cc(-c3ccccc3)[nH]c2c1]

The title compound was prepared by the above general procedure B. Yield: 14%%; Mp 271° C.; IR (neat): 2961, 1723, 1638, 1594, 1583, 1552, 1499, 1462, 1366, 1272, 1245, 1211, 1031, 760, 744, 687 cm$^{-1}$; $^1$H NMR (600 MHz, CD$_3$OD/CDCl$_3$) δ 7.39-7.29 (m, 2H), 7.92 (d, J=8.6 Hz, 1H), 7.77-7.69 (m, 2H), 7.55-7.49 (m, 3H), 6.58 (s, 1H), 4.41 (q, J=7.1 Hz, 2H), 1.41 (t, J=6.9 Hz, 3H); $^{13}$C NMR (150 MHz, CD$_3$OD/CDCl$_3$) δ 178.4, 165.6, 152.3, 139.6, 133.3, 133.1, 130.4, 128.6, 126.8, 126.7, 125.1, 123.3, 120.2, 108.1, 61.3, 13.4.

General Procedure C for Synthesis of RJ-LC-15-19 and RJ-LC-15-20

A solution of AS1712 or compound 2h (0.068 mmol) in MeOH/DCM (1:1) (1.4 ml) was treated with MsOH (0.068 mmol) and stirred at room temperature for 30 min. Next, the solution was concentrated in vacuo to get RJ-LC-15-19 or RJ-LC-15-20.

Ethyl 4-oxo-2-phenyl-1,4-dihydroquinoline-6-carboxylate Methane Sulfonate (RJ-LC-15-19)

The title compound was prepared by the above general procedure C. Yield: 99%; Mp 245° C.; IR (neat): 3093, 2497, 1714, 1645, 1231, 1085, 1037, 1027, 917, 771, 762 cm$^{-1}$; $^1$H NMR (600 MHz, CD$_3$OD/CDCl$_3$) 9.08 (d, J=1.5 Hz, 1H), 8.56 (dd, J=9.0 Hz, J=2.0 Hz, 1H), 8.22 (d, J=8.8 Hz, 1H), 7.98-7.93 (m, 2H), 7.77-7.66 (m, 3H), 4.48 (q, J=7.3 Hz, 2H), 2.71 (s, 3H), 1.46 (t, J=7.1 Hz, 3H); $^{13}$C NMR (150 MHz, DMSO-d$_6$) δ 171.5, 164.9, 157.4, 142.2, 134.3, 132.9, 131.5, 129.7, 129.4, 128.3, 126.3, 120.2, 119.6, 105.0, 61.9, 38.5, 13.6.

Ethyl 2-(3-fluorophenyl)-4-oxo-1,4-dihydroquinoline-6-carboxylate Methanesulfonate (RJ-LC-15-20)

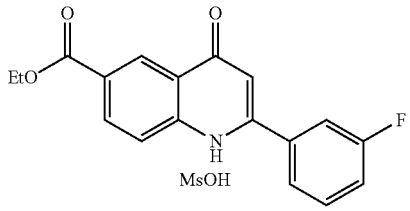 [SMILES: "MsOH" ; CCOC(=O)c1ccc2[nH]c(-c3cccc(F)c3)cc(=O)c2c1]

The title compound was prepared by the above general procedure C. Yield: 99%; Mp 258° C.; IR (neat): 3088, 2499, 1715, 1586, 1228, 1136, 1040, 878, 794, 774, 763 cm$^{-1}$; $^1$H NMR (600 MHz, CD$_3$OD/CDCl$_3$) 9.06 (d, J=1.6 Hz, 1H), 8.55 (dd, J=9.0 Hz, J=2.0 Hz, 1H), 8.24 (d, J=8.9 Hz, 1H), 7.81-7.63 (m, 3H), 7.48-7.41 (m, 1H), 4.47 (q, J=7.3 Hz, 2H), 2.73 (s, 3H), 1.46 (t, J=7.0 Hz, 3H); $^{13}$C NMR (150 MHz, DMSO-d$_6$) δ 171.8, 164.8, 164.3, 161.8, 155.7, 142.2, 134.5, 133.5, 131.7, 129.5, 126.4, 124.4, 120.3, 119.8, 119.6, 115.5, 115.3, 105.3, 61.9, 38.6, 13.7.

TABLE 8

| IC$_{50}$ of Exemplary Compounds | |
|---|---|
| Compound | IC$_{50}$(μM) |
| RJ-LC-15 (AS1712) | 0.033 ± 0.004 |
| RJ-LC-15-1 (2a) | >5 |

TABLE 8-continued
IC$_{50}$ of Exemplary Compounds
| Compound | IC$_{50}$(μM) |
|---|---|
| 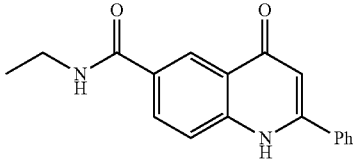 [SMILES: CCNC(=O)c1ccc2[nH]c(-c3ccccc3)cc(=O)c2c1] RJ-LC-15-2 (2b) | 3.7 ± 0.73 |
| 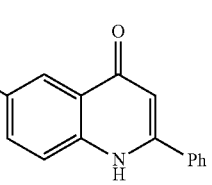 RJ-LC-15-3 | 3.3 ± 0.99 |
| 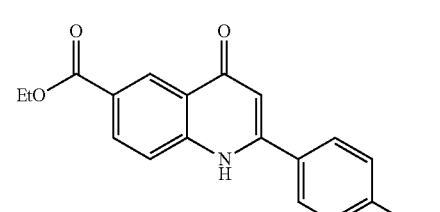 RJ-LC-15-4 (2c) | 2.2 ± 0.2 |
| 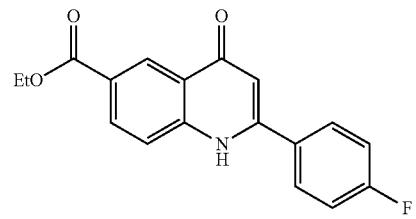 [SMILES: CCOC(=O)c1ccc2[nH]c(-c3ccc(F)cc3)cc(=O)c2c1] RJ-LC-15-5 (2d) | 2.1 ± 0.21 |
| 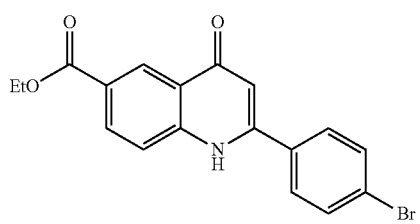 [SMILES: CCOC(=O)c1ccc2[nH]c(-c3ccc(Br)cc3)cc(=O)c2c1] RJ-LC-15-6 (2e) | 4.5 ± 0.9 |
| 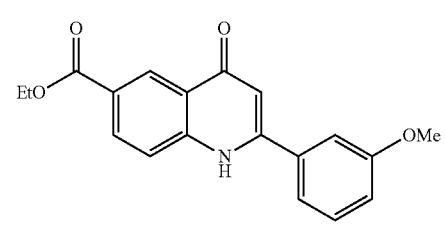 [SMILES: CCOC(=O)c1ccc2[nH]c(-c3cccc(OC)c3)cc(=O)c2c1] RJ-LC-15-7 (2g) | 0.044 ± 0.001 |

TABLE 8-continued
IC$_{50}$ of Exemplary Compounds
| Compound | IC$_{50}$(μM) |
|---|---|
| 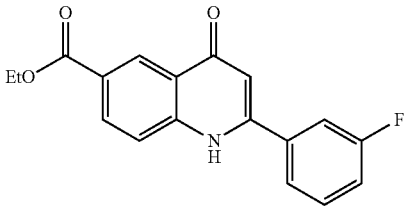 [SMILES: CCOC(=O)c1ccc2[nH]c(-c3cccc(F)c3)cc(=O)c2c1]<br>RJ-LC-15-8 (2h) | 0.024 ± 0.001 |
| 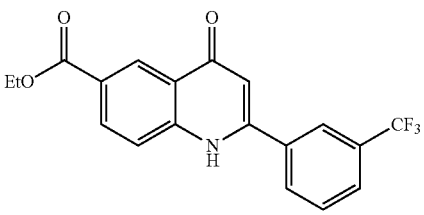<br>RJ-LC-15-9 (2i) | 0.78 ± 0.012 |
| 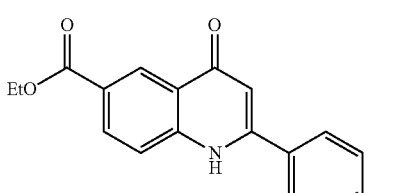<br>RJ-LC-15-10 (2f) | 0.475 ± 0.031 |
| 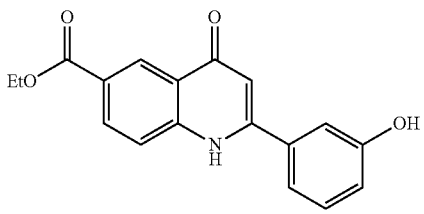 [SMILES: CCOC(=O)c1ccc2[nH]c(-c3cccc(C(F)(F)F)c3)cc(=O)c2c1]<br>RJ-LC-15-11 (2j) | 1.95 ± 0.2 |
| 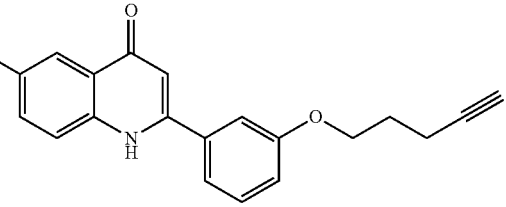<br>RJ-LC-15-12 (4) | 0.267 ± 0.021 |
| 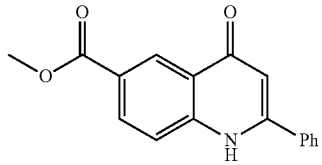 [SMILES: COC(=O)c1ccc2[nH]c(-c3ccccc3)cc(=O)c2c1]<br>RJ-LC-15-14 (2k) | 0.207 ± 0.039 |

TABLE 8-continued
IC$_{50}$ of Exemplary Compounds
| Compound | IC$_{50}$(μM) |
|---|---|
| 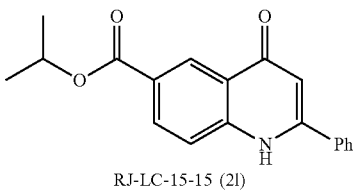<br>RJ-LC-15-15 (2l) | 0.048 ± 0.005 |
| 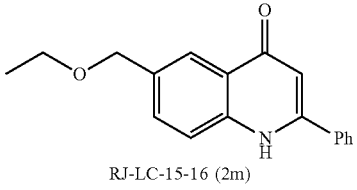<br>RJ-LC-15-16 (2m) | 0.81 ± 0.12 |
| 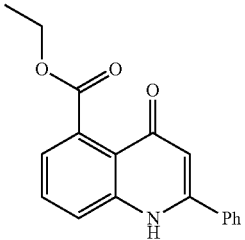 [SMILES: CCOC(=O)c1cccc2[nH]c(-c3ccccc3)cc(=O)c12]<br>RJ-LC-15-17 | >10 μM |
| 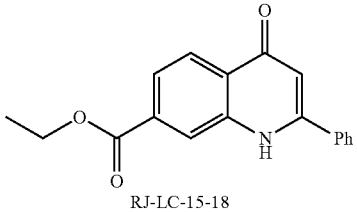<br>RJ-LC-15-18 | 0.097 ± 0.003 |
| 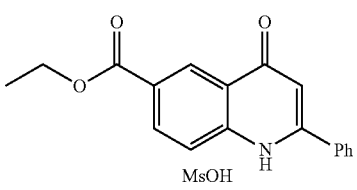 [SMILES: "MsOH" ; CCOC(=O)c1ccc2[nH]c(-c3ccccc3)cc(=O)c2c1]<br>MsOH<br>RJ-LC-15-19 (MsOH salt of RJ-LC-15) | 0.069 ± 0.004 |
| 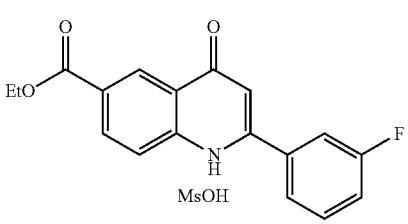 [SMILES: "MsOH" ; CCOC(=O)c1ccc2[nH]c(-c3cccc(F)c3)cc(=O)c2c1]<br>MsOH<br>RJ-LC-15-20 (MsOH salt of RJ-LC-15-8) | 0.042 ± 0.004 |
| 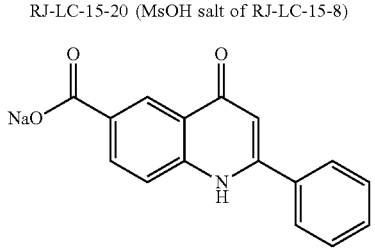<br>RJ-LC-15-21 | >10 μM |

TABLE 8-continued
IC$_{50}$ of Exemplary Compounds
| Compound | IC$_{50}$(μM) |
|---|---|
| 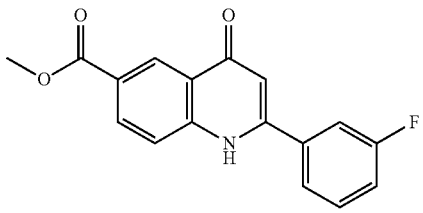 [SMILES: COC(=O)c1ccc2[nH]c(-c3cccc(F)c3)cc(=O)c2c1] RJ-LC-15-22 | 0.027 ± 0.006 |
| 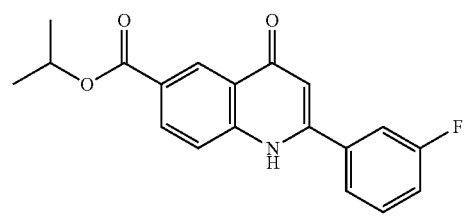 [SMILES: CC(C)OC(=O)c1ccc2[nH]c(-c3cccc(F)c3)cc(=O)c2c1] RJ-LC-15-23 | 0.006 ± 0.002 |
| 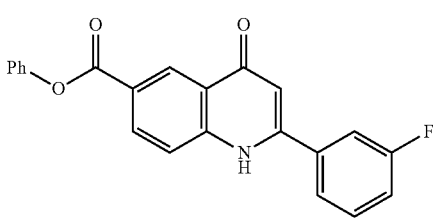 [SMILES: O=C(Oc1ccccc1)c1ccc2[nH]c(-c3cccc(F)c3)cc(=O)c2c1] RJ-LC-15-24 | 0.3 ± 0.008 |
| 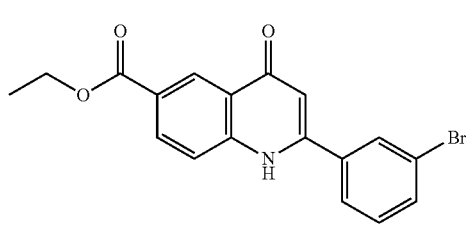 [SMILES: CCOC(=O)c1ccc2[nH]c(-c3cccc(Br)c3)cc(=O)c2c1] RJ-LC-15-25 | 0.07 ± 0.019 |
| 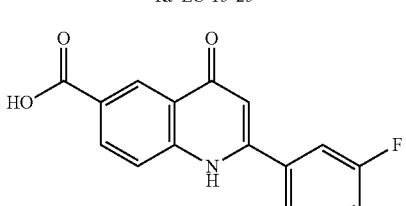 RJ-LC-15-26 | >10 |
| 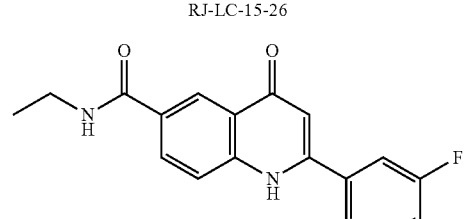 RJ-LC-15-27 | 5.6 ± 0.39 |
The analog RJ-LC-15-23 showed superior anti-proliferative potency than AS1712 and RJ-LC-15-8 in H1975 and MDA-MB-231. RJ-LC-15-23 was also relatively non-toxic against the human fibroblast (HFB) (IC$_{50}$>10 μM). This data suggest that RJ-LC-15-23 may have great potential for cancer therapy.

TABLE 9

| IC$_{50}$ of RJ-LC-15-23 | | | |
|---|---|---|---|
| IC$_{50}$ (nM) | AS1712 | RJ-LC-15-8 | RJ-LC-15-23 |
| H1975 | 33 ± 4.86 | 24 ± 1.12 | 6 ± 2.16 |
| MDA-MB-231 | 55 ± 6.83 | 35 ± 1.45 | 10 ± 0.5 |
| HFB | >10 μM | >10 μM | >10 μM |

Discussion

Cancer is the second leading cause of death worldwide and afflicts ~40% of the global population. Lung, breast, colorectal, and prostate cancers are the most common types and account for ~46% of all cancer deaths, with lung cancer being responsible for the highest number of deaths. MTAs are widely used to treat advanced cancers, but prolonged treatment with MTAs reduces their clinical efficacy owing to the development of drug resistance by the cancers. Thus, the development of new agents that improve drug efficacy and overcome drug resistance is an ongoing effort. For the study reported herein, it was shown that exemplary compound AS1712 has the potential to treat various types of cancers and the ability to overcome MDR caused by MTAs with good efficacy and a good therapeutic window Cancer cells rely on microtubules to advance through mitosis and rapidly divide, which has made microtubules an important therapeutic target in cancer treatments for >50 years. When MTAs alter microtubule dynamics, they cause mitotic arrest and trigger mitochondria-mediated intrinsic apoptosis. It was demonstrated that exemplary compound AS1712 inhibited microtubule polymerization and nucleation and disrupted mitotic spindle organization. AS1712 also induced mitotic arrest and then triggered release of cytochrome c and cleavage of caspase-9 to activate intrinsic apoptosis in several cancer cell lines. AS1712 also had good in vivo activity against tumor growth with no noticeable toxicity. The anti-cancer activities of exemplary compound AS1712 are similar to those of MTAs currently used clinically, although AS1712 has a different tubulin-binding site.

There are at least four binding sites on tubulin with a stabilizing or destabilizing function. The colchicine-binding site is located on β-tubulin at its interface with α-tubulin. Colchicine-binding site inhibitors (CBSIs) destabilize microtubule assembly and exhibit anti-angiogenesis and vascular-disruption activities, which are not found for inhibitors of the other functional sites. Unlike taxanes and vinca alkaloids, CBSIs can counteract the effects of overexpression of β-tubulin isoforms, and MDR mechanisms have little effect on CBSI activity. The results showed that AS1712 directly interacts with the colchicine-binding pocket of β-tubulin, indicating that AS1712 should be classified as a CBSI and suggested that, because of its binding site, AS1712 may not be susceptible to resistance induced by conformational changes in β-tubulin caused by mutations.

Currently, no CBSIs are approved for cancer therapy because colchicine and its derivatives are toxic to humans. However, exemplary compound AS1712 showed a >100-fold therapeutic window for the cell lines analyzed here and did not inhibit microtubule polymerization, cell-cycle arrest, or apoptosis in HFB cells at the highest treatment dosage that was used for the cancer cells. AS1712 also showed no notable toxicity in the animal model. Thus AS1712 may be a CBSI with low toxicity and has the potential to act as a lead compound for further development of anti-cancer agents.

MDR is a major cause of treatment failure in various cancer therapies. Overexpression of P-gp is the main MDR mechanism involved in MTA-induced resistance because most MTAs, including paclitaxel, vincristine, vinblastine, and docetaxel, are exported from cells by P-gp. P-gp pumps many different types of cytotoxic drugs out of cancer cells, thereby decreasing intracellular drug concentrations and resulting in treatment failure. AS1712 inhibited the proliferation of KBtax, KBvin, and CEM/VBL cells that overexpressed P-gp with IC$_{50}$ values comparable to those of their respective parental control cell lines. The results suggested that AS1712 either directly inhibited P-gp activity or did not function as a P-gp substrate, thereby against P-gp overexpressing cancer cells. The rhodamine efflux assay and immunoblotting study ruled out the possibility that AS1712 directly inhibits P-gp pump activity or P-gp expression, which supports the hypothesis that AS1712 is not a P-gp substrate. Although other P-gp inhibitors, such as verapamil, cyclosporine, and valspodar, can reverse the MDR phenotype of cancer cells, clinical trials involving these inhibitors showed toxic side effects and failed to improve clinical outcomes. With its inability to act as a P-gp substrate, AS1712 provides a different treatment strategy for MDR cancers. Ixabepilone is a second-line MTA used for treatment of advanced breast cancers that no longer respond to currently available chemotherapies; however, it was found that some MDR cell lines resist treatment by ixabepilone, which thereby restricts its clinical use. In contrast, AS1712 has the potential to treat various types of cancers, including those of the lung, breast, ovary, prostate, and head and neck and leukemia that were first clinically subjected to taxanes or vinca alkaloids. The results suggest that exemplary compound AS1712 or exemplary derivatives, for example, RJ-LC-15-8 may counteract multidrug resistance in various types of cancers.

CONCLUSIONS

For the study reported herein, it was shown that exemplary compound AS1712 directly targets the colchicine-binding site of β-tubulin to disassemble microtubules, which subsequently induces mitotic arrest and activates apoptosis. Exemplary compound AS1712 can overcome the MTAs-induced acquired resistance, including β-tubulin alterations and P-gp mediated multidrug resistance. Exemplary compound AS1712 and exemplary derivatives, for example, RJ-LC-15-8 may have great potential for cancer therapy.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method of treating one or more cancers of breast cancer, ovarian cancer, prostate cancer, colon cancer, head cancer, neck cancer, and head and neck cancer in a subject in need thereof, the method comprising administering to the subject a therapeutically effective amount of a compound of formula (I):

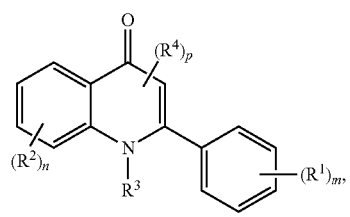

(I)

or a pharmaceutically acceptable salt, co-crystal, tautomer, or stereoisomer thereof, wherein:
each instance of $R^1$ is independently halogen, —C(=O)(unsubstituted alkyl), unsubstituted or substituted alkyl by halogen, unsubstituted or substituted alkenyl by halogen, unsubstituted or substituted alkynyl by halogen, unsubstituted or substituted carbocyclyl by halogen, unsubstituted heterocyclyl, unsubstituted aryl, unsubstituted heteroaryl, —CN, —$OR^{D1}$, —$N(R^{D1a})_2$, or —$SR^{D1}$;
each instance of $R^2$ is independently halogen, —C(=O)$R^{aa}$, —CHO, —$CO_2R^{aa}$, —C(=O)N($R^{bb}$)$_2$, —C(=O)(OCH$_2$CH$_2$)$_z$OR$^{2c}$, —(CH$_2$)$_x$OR$^{aa}$, —C(=S)N($R^{bb}$)$_2$, —C(=O)SR$^{aa}$, —C(=S)SR$^{aa}$, —C(=NR$^{bb}$)R$^{aa}$, —C(=NR$^{bb}$)OR$^{aa}$, —C(=NR$^{bb}$)N($R^{bb}$)$_2$, —C(=O)NR$^{bb}$SO$_2$R$^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, —CN, —$OR^{D1}$, —$N(R^{D1a})_2$, or —$SR^{D1}$; and at least one $R^2$ is —C(=O)$R^{aa}$, —CHO, —$CO_2R^{aa}$, —C(=O)N($R^{bb}$)$_2$, —C(=O)(OCH$_2$CH$_2$)$_z$OR$^{2c}$, —(CH$_2$)$_x$OR$^{aa}$, —C(=S)N($R^{bb}$)$_2$, —C(=O)SR$^{aa}$, —C(=S)SR$^{aa}$, —C(=NR$^{bb}$)R$^{aa}$, —C(=NR$^{bb}$)OR$^{aa}$, —C(=NR$^{bb}$)N($R^{bb}$)$_2$, —C(=O)NR$^{bb}$SO$_2$R$^{aa}$ or —CN;
$R^3$ is hydrogen, unsubstituted alkyl, or a nitrogen protecting group;
each instance of $R^4$ is independently halogen, —C(=O)$R^{aa}$, —CHO, —$CO_2R^{aa}$, —C(=O)N($R^{bb}$)$_2$, —C(=NR$^{bb}$)R$^{aa}$, —C(=NR$^{bb}$)OR$^{aa}$, —C(=NR$^{bb}$)N($R^{bb}$)$_2$, —C(=O)NR$^{bb}$SO$_2$R$^{aa}$, —C(=S)N($R^{bb}$)$_2$, —C(=O)SR$^{aa}$, —C(=S)SR$^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, —CN, —$OR^{D1}$, —$N(R^{D1a})_2$, or —$SR^{D1}$;
$R^{D1}$ is hydrogen, —C(=O)$R^{aa}$, —CHO, —$CO_2R^{aa}$, —C(=O)N($R^{bb}$)$_2$, —C(=NR$^{bb}$)R$^{aa}$, —C(=NR$^{bb}$)OR$^{aa}$, —C(=NR$^{bb}$)N($R^{bb}$)$_2$, —C(=O)NR$^{bb}$SO$_2$R$^{aa}$, —C(=S)N($R^{bb}$)$_2$, —C(=O)SR$^{aa}$, —C(=S)SR$^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, an oxygen protecting group when attached to an oxygen atom, or a sulfur protecting group when attached to a sulfur atom;
each occurrence of $R^{D1a}$ is hydrogen, —C(=O)$R^{aa}$—CHO, —$CO_2R^{aa}$, —C(=O)N($R^{bb}$)$_2$, —C(=NR$^{bb}$)$R^{aa}$, —C(=NR$^{bb}$)OR$^{aa}$, —C(=NR$^{bb}$)N($R^{bb}$)$_2$, —C(=O)NR$^{bb}$SO$_2$R$^{aa}$, —C(=S)N($R^{bb}$)$_2$, —C(=O)SR$^{aa}$, —C(=S)SR$^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group; or optionally-two instances of $R^{D1a}$ are taken together with their intervening atoms to form an unsubstituted heterocyclic or unsubstituted heteroaryl ring;
$R^{aa}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or an oxygen protecting group when attached to an oxygen atom;
each occurrence of $R^{bb}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group when attached to a nitrogen atom;
$R^{2c}$ is hydrogen;
m is 0, 1, 2, 3, 4, or 5;
n is 1, 2, 3, or 4;
x is 1, 2, 3, 4, 5, or 6;

z is 1, 2, 3, 4, 5, or 6; and p is 0 or 1.

2. The method of claim 1, wherein m is 0.

3. The method of claim 1, wherein m is 1.

4. The method of claim 1, wherein at least one instance of $R^1$ is halogen.

5. The method of claim 1, wherein at least one instance of $R^1$ is fluoro or bromo.

6. The method of claim 1, wherein at least one instance of $R^1$ is alkyl substituted with halogen.

7. The method of claim 6, wherein at least one instance of $R^1$ is $-CF_3$.

8. The method of claim 1, wherein at least one instance of $R^1$ is $-OR^{D1}$, and $R^{D1}$ is hydrogen or unsubstituted alkyl, unsubstituted alkenyl or unsubstituted alkynyl.

9. The method of claim 8, wherein at least one instance of $R^1$ is $-OH$, $-OMe$, or of formula:

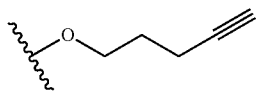

.

10. The method of claim 1, wherein $R^3$ is hydrogen.

11. The method of claim 1, wherein n is 1.

12. A method of treating one or more cancers of lung cancer, breast cancer, ovarian cancer, prostate cancer, colon cancer, head cancer, neck cancer, head and neck cancer and leukemia in a subject in need thereof, the method comprising administering to the subject a therapeutically effective amount of a compound of Formulae (IA), (IB), or (IC):

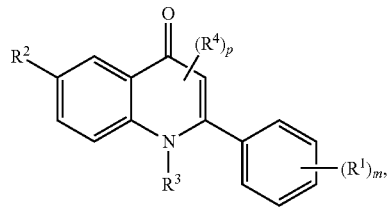
(IA)

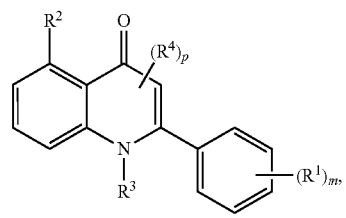
(IB)

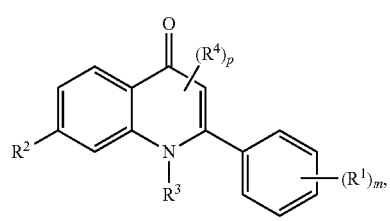
(IC)

or a pharmaceutically acceptable salt, co-crystal, tautomer, or stereoisomer thereof, wherein:

each instance of $R^1$ is independently halogen, $-C(=O)$(-unsubstituted alkyl), unsubstituted or substituted alkyl by halogen, unsubstituted or substituted alkenyl by halogen, unsubstituted or substituted alkynyl by halogen, unsubstituted or substituted carbocyclyl by halogen, unsubstituted heterocyclyl, unsubstituted aryl, unsubstituted heteroaryl, $-CN$, $-OR^{D1}$, $-N(R^{D1a})_2$, or $-SR^{D1}$;

$R^2$ of the formula (IA) is independently $-C(=O)R^{aa}$, $-CHO$, $-CO_2R^{aa}$, $-C(=O)N(R^{bb})_2$, $-C(=O)(OCH_2CH_2)_zOR^{2c}$, $-(CH_2)_xOR^{aa}$, $-C(=S)N(R^{bb})_2$, $-C(=O)SR^{aa}$, $-C(=S)SR^{aa}$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, $-CN$, or $-N(R^{D1a})_2$; $R^2$ of the formula (IB) is independently halogen, $-C(=O)R^{aa}$ $-CHO$, $-CO_2R^{aa}$, $-C(=O)N(R^{bb})_2$, $-C(=O)(OCH_2CH_2)_zOR^{2c}$, $-(CH_2)_xOR^{aa}$, $-C(=S)N(R^{bb})_2$, $-C(=O)SR^{aa}$, $-C(=S)SR^{aa}$, $-C(=NRbb)R^{aa}$ $-C(=NR^{bb})OR^{aa}$, $-C(=NR^{bb})N(R^{bb})_2$, $-C(=O)NR^{bb}SO_2R^{aa}$ unsubstituted alkyl, unsubstituted alkenyl, unsubstituted alkynyl, unsubstituted carbocyclyl, unsubstituted heterocyclyl, unsubstituted aryl, -unsubstituted heteroaryl, $-CN$, $-OR^{D1}$, $-N(R^{D1a})_2$, or $-SR^{D1}$; and $R^2$ of the formula (IC) is independently halogen, $-C(=O)OR^{2a}$, $-C(=O)N(R^{bb})_2$, $-C(=O)(OCH_2CH_2)_zOR^{2c}$, $-C(=S)N(R^{bb})_2$, $-C(=O)SR^{aa}$, $-C(=S)SR^{aa}$, $-(CH_2)_xOR^{aa}$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, $-CN$, $-OR^{D1}$, $-N(R^{D1a})_2$, or $-SR^{D1}$;

$R^3$ is hydrogen, unsubstituted alkyl, or a nitrogen protecting group;

each instance of $R^4$ is independently halogen, $-C(=O)R^{aa}$ $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $-C(=S)SR^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, $-CN$, $-OR^{D1}$, $-N(R^{D1a})_2$, or $-SR^{D1}$;

$R^{D1}$ is hydrogen, $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $C(=S)SR^{aa}$, unsubstituted alkyl, unsubstituted alkenyl, -unsubstituted alkynyl, unsubstituted carbocyclyl, unsubstituted heterocyclyl, unsubstituted aryl, unsubstituted heteroaryl, an oxygen protecting group when attached to an oxygen atom, or a sulfur protecting group when attached to a sulfur atom;

each occurrence of $R^{D1a}$ is hydrogen, $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $-C(=S)SR^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group; or two instances of $R^{D1a}$ are taken together with their intervening atoms to form an unsubstituted heterocyclic or unsubstituted heteroaryl ring;

$R^{2a}$ is unsubstituted alkyl, unsubstituted alkenyl, unsubstituted alkynyl, unsubstituted carbocyclyl, unsubstituted heterocyclyl, unsubstituted aryl, unsubstituted heteroaryl, or an oxygen protecting group when attached to an oxygen atom;

$R^{aa}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or an oxygen protecting group when attached to an oxygen atom;

each occurrence of $R^{bb}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group when attached to a nitrogen atom;

$R^{2c}$ is hydrogen;

m is 0, 1, 2, 3, 4, or 5;

x is 1, 2, 3, 4, 5, or 6;

z is 1, 2, 3, 4, 5, or 6; and p is 0 or 1.

13. The method of claim 12, wherein $R^2$ of the formula (IA) is is —$CO_2R^{aa}$, —C(═O)N($R^{bb}$)$_2$, or —$(CH_2)_xOR^{aa}$ or —C(═O)(OCH$_2$CH$_2$)$_z$O($R^{2c}$), $R^2$ of the formula (IB) is is —$CO_2R^{aa}$, —C(═O)N($R^{bb}$)$_2$, or —$(CH_2)_xOR^{aa}$ or —C(═O)(OCH$_2$CH$_2$)$_z$O($R^{2c}$), and $R^2$ of the formula (IC) is —C(═O)$OR^{2a}$, —C(═O)N($R^{bb}$)$_2$, or —$(CH_2)_xOR^{aa}$ or —C(═O)(OCH$_2$CH$_2$)$_z$O($R^{2c}$).

14. The method of claim 13, wherein $R^2$ of the formula (IA) is —$CO_2R^{aa}$ or —C(═O)(OCH$_2$CH$_2$)$_z$O($R^{2c}$), $R^2$ of the formula (IB) is —$CO_2R^{aa}$ or —C(═O)(OCH$_2$CH$_2$)$_z$O($R^{2c}$), and $R^2$ of the formula (IC) is —C(═O)$OR^{2a}$ or —C(═O)(OCH$_2$CH$_2$)$_z$O($R^{2c}$), and $R^{2a}$ is unsubstituted $C_{1-6}$ alkyl, $R^{aa}$ is hydrogen or unsubstituted $C_{1-6}$ alkyl, $R^{2c}$ is hydrogen, and z is 1, 2, 3, 4, 5, or 6.

15. The method of claim 14, wherein —$CO_2R^{aa}$ is —C(═O)OH, —C(═O)OMe, —C(═O)OEt, or —C(═O)O($^i$Pr), —C(═O)$OR^{2a}$ is —C(═O)OMe, —C(═O)OEt or —C(═O)O($^i$Pr), and —C(═O)(OCH$_2$CH$_2$)$_z$O($R^{2c}$) is —C(═O)(OCH$_2$CH$_2$)$_3$OH, or —C(═O)(OCH$_2$CH$_2$)$_4$OH.

16. The method of claim 13, wherein $R^2$ of the formulas (IA), (IB) and (IC) is —C(═O)NH($R^{bb}$), and $R^{bb}$ is unsubstituted $C_{1-6}$ alkyl.

17. The method of claim 16, wherein $R^2$ of the formulas (IA), (IB) and (IC) is —C(═O)NH(Et).

18. The method of claim 13, wherein $R^2$ of the formulas (IA), (IB) and (IC) is —$(CH_2)_xOR^{aa}$, x is 1, 2, 3, 4, or 5, and $R^{aa}$ is unsubstituted $C_{1-6}$ alkyl.

19. The method of claim 18, wherein $R^2$ of the formulas (IA), (IB) and (IC) is —(CH$_2$)OEt.

20. The method of claim 1, wherein p is 0.

21. The method of claim 13, wherein the compound is of formula:

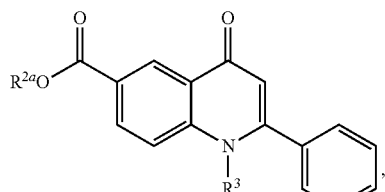

,

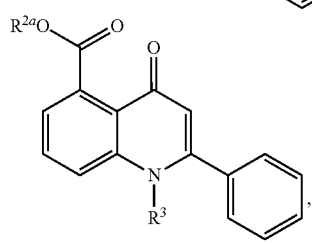

,

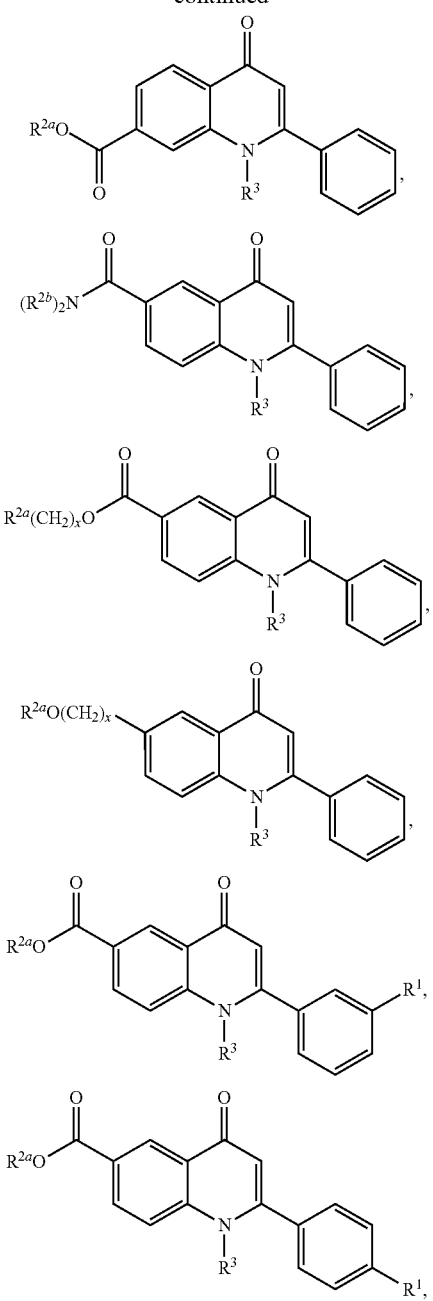

or a pharmaceutically acceptable salt, co-crystal, tautomer, or stereoisomer thereof.

22. The method of claim 12, wherein the compound is of formula:

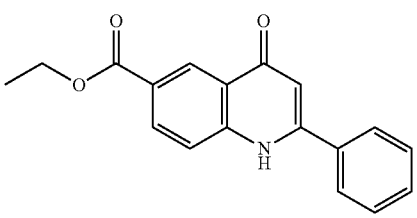

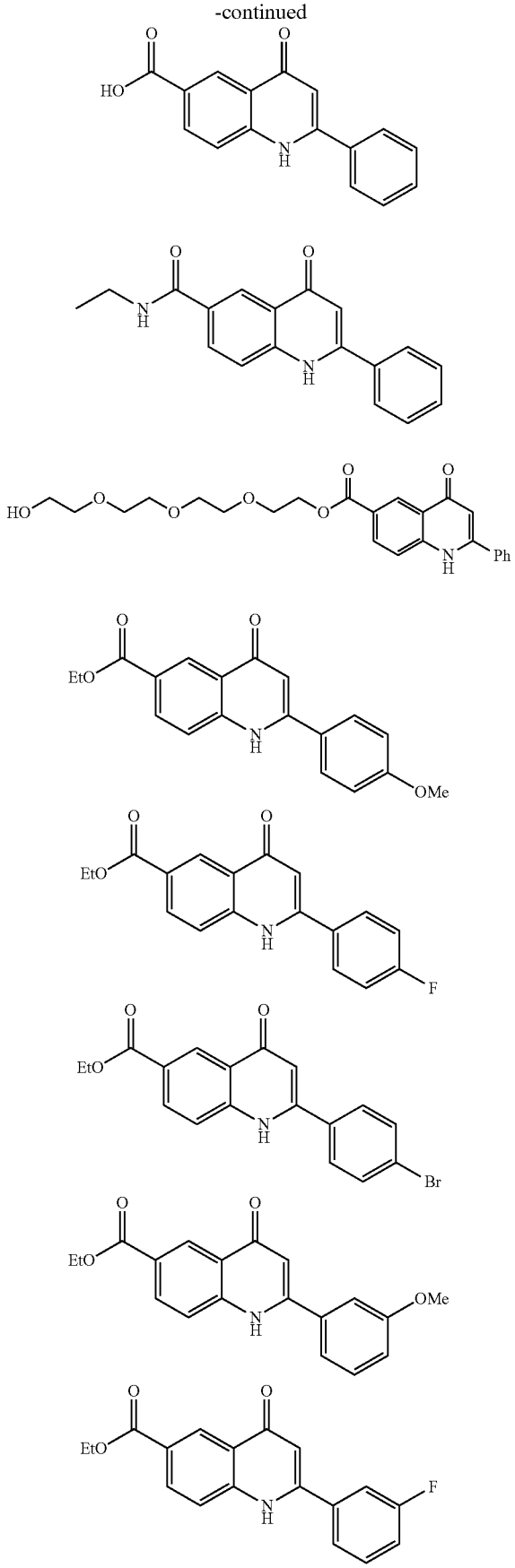
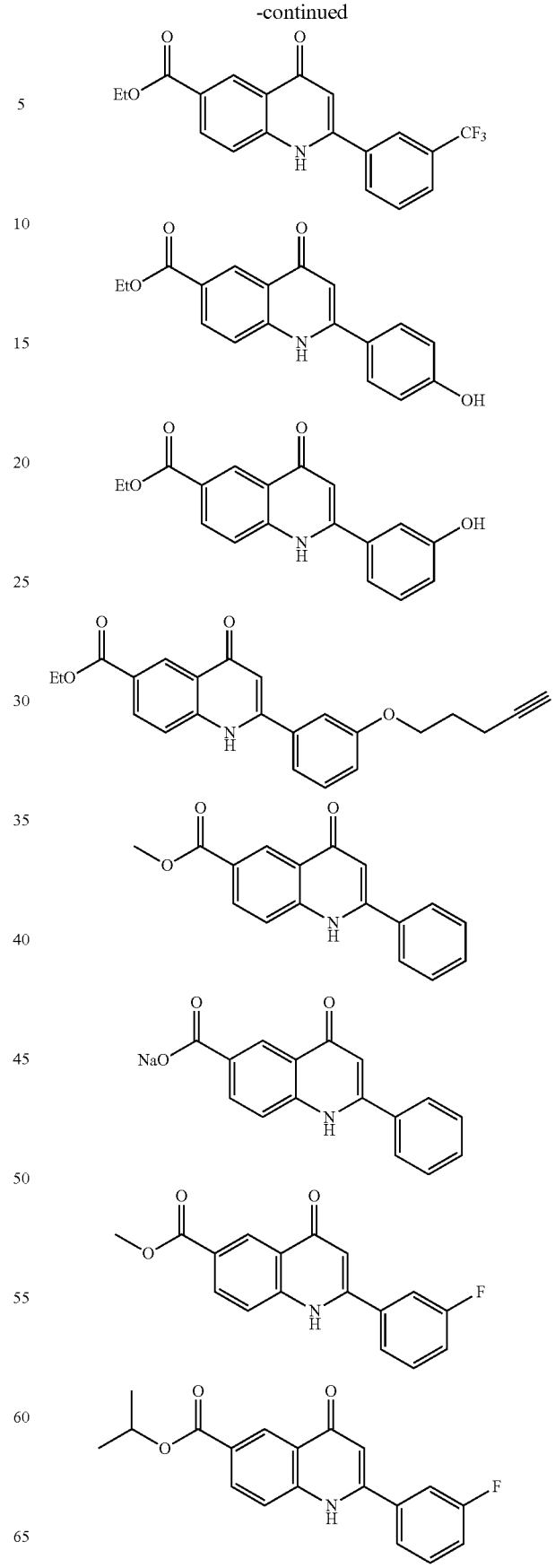

-continued

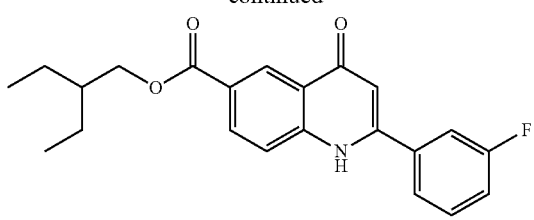
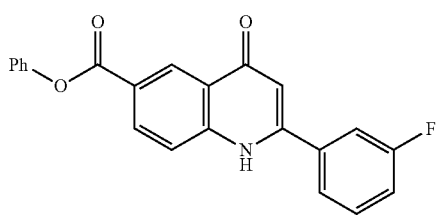
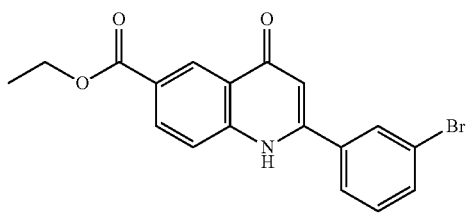
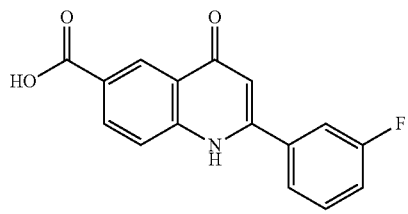 [SMILES: O=C(O)c1ccc2[nH]c(-c3cccc(F)c3)cc(=O)c2c1]
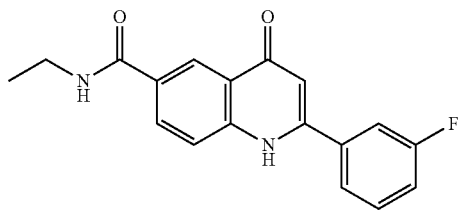 [SMILES: CCNC(=O)c1ccc2[nH]c(-c3cccc(F)c3)cc(=O)c2c1]
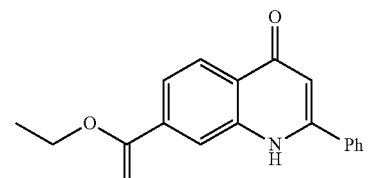
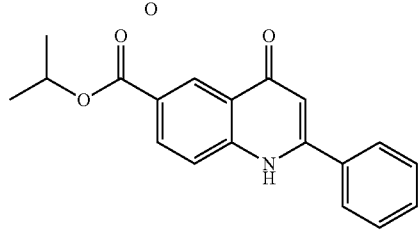
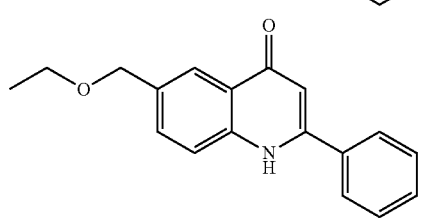

-continued

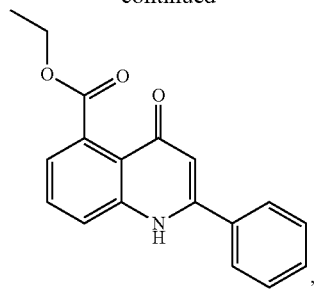

or a pharmaceutically acceptable salt, co-crystal, tautomer, or stereoisomer thereof.

23. The method of claim 22, wherein the compound is of formula:

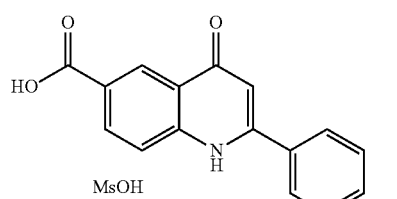
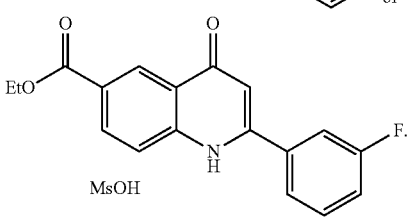

24. A method of treating leukemia in a subject in need thereof, the method comprising administering to the subject a therapeutically effective amount of a compound of formula (IA)

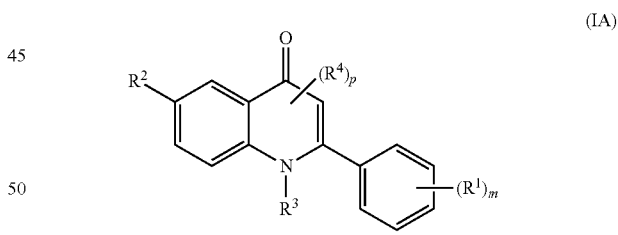

(IA)

or a pharmaceutically acceptable salt, co-crystal, tautomer, or stereoisomer thereof, wherein:
each instance of $R^1$ is independently halogen, —C(=O)(-unsubstituted alkyl), unsubstituted or substituted alkyl by halogen, unsubstituted or substituted alkenyl by halogen, unsubstituted or substituted alkynyl by halogen, unsubstituted or substituted carbocyclyl by halogen, unsubstituted heterocyclyl, unsubstituted aryl, unsubstituted heteroaryl, —CN, —$OR^{D1}$, —$N(R^{D1a})_2$, or —$SR^{D1}$;
$R^2$ is independently halogen, —C(=O)$R^{aa}$, —CHO, —$CO_2R^{aa}$, —C(=O)N($R^{bb}$)$_2$, —C(=O)(OCH$_2$CH$_2$)$_z$$OR^{2c}$, —(CH$_2$)$_x$$OR^{aa}$, —C(=S)N($R^{bb}$)$_2$, —C(=O)S$R^{aa}$, —C(=S)S$R^{aa}$, —C(=N$R^{bb}$)$R^{aa}$, —C(=N$R^{bb}$)

$OR^{aa}$, $-C(=NR^{bb})N(R^{bb})_2$, $-C(=O)NR^{bb}SO_2R^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, $-CN$, $-OR^{D1}$, $-N(R^{D1a})_2$, or $-SR^{D1}$;

$R^3$ is hydrogen, unsubstituted alkyl, or a nitrogen protecting group;

each instance of $R^4$ is independently halogen, $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $-C(=S)SR^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, $-CN$, $-OR^{D1}$, $-N(R^{D1a})_2$, or $-SR^{D1}$;

$R^{D1}$ is hydrogen, $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $-C(=S)SR^{aa}$, unsubstituted alkyl, unsubstituted alkenyl, unsubstituted alkynyl, unsubstituted carbocyclyl, unsubstituted heterocyclyl, unsubstituted aryl, unsubstituted heteroaryl, an oxygen protecting group when attached to an oxygen atom, or a sulfur protecting group when attached to a sulfur atom;

each instance of $R^{D1a}$ is hydrogen, $-C(=O)R^{aa}$, $-CHO$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-C(=O)NR^{bb}SO_2R^{aa}$, $-C(=S)N(R^{bb})_2$, $-C(=O)SR^{aa}$, $-C(=S)SR^{aa}$ unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group; or two instances of $R^{D1a}$ are taken together with their intervening atoms to form an unsubstituted heterocyclic or unsubstituted heteroaryl ring;

$R^{aa}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or an oxygen protecting group when attached to an oxygen atom;

each occurrence of $R^{bb}$ is hydrogen, unsubstituted alkyl, unsubstituted alkenyl, unsubstituted alkynyl, unsubstituted carbocyclyl, unsubstituted heterocyclyl, unsubstituted aryl, unsubstituted heteroaryl, or a nitrogen protecting group when attached to a nitrogen atom;

$R^{2c}$ is hydrogen;

m is 0, 1, 2, 3, 4, or 5;

x is 1, 2, 3, 4, 5, or 6;

z is 1, 2, 3, 4, 5, or 6; and p is 0 or 1.

25. The method of claim 12, wherein the lung cancer is non-small cell lung cancer.

26. The method of claim 12, wherein the breast cancer is triple-negative breast cancer.

27. The method of claim 12, wherein the one or more cancers are resistant to treatment by one or more microtubule-targeting agents.

28. The method of claim 27, wherein the one or more microtubule-targeting agents comprise a taxane or a vinca alkaloid.

29. The method of claim 28, wherein the taxane is paclitaxel or ixabepilone.

30. The method of claim 28, wherein the *vinca* alkaloid is vincristine or vinblastine.

31. The method of claim 27, wherein the one or more microtubule-targeting agents comprise paclitaxel and vincristine.

32. The method of claim 12, wherein the one or more cancers are resistant to multiple drugs.

33. The method of claim 32, wherein the one or more cancers resistant to multiple drugs are associated with P-glycoprotein (P-gp) overexpression.

34. The method of claim 32, wherein the one or more cancers resistant to multiple drugs are associated with β-tubulin mutations.

\* \* \* \* \*